(12) United States Patent
Jameson et al.

(10) Patent No.: US 9,155,774 B2
(45) Date of Patent: Oct. 13, 2015

(54) SCAFFOLD-KINASE INTERACTION BLOCKADES AND USES THEREOF IN TREATING CANCER

(75) Inventors: Katherine LaRoque Jameson, Nashville, TN (US); Paul A. Khavari, Palo Alto, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 4 days.

(21) Appl. No.: 14/123,953

(22) PCT Filed: Apr. 5, 2012

(86) PCT No.: PCT/US2012/032375
§ 371 (c)(1),
(2), (4) Date: Feb. 18, 2014

(87) PCT Pub. No.: WO2012/170113
PCT Pub. Date: Dec. 13, 2012

(65) Prior Publication Data
US 2014/0162960 A1    Jun. 12, 2014

Related U.S. Application Data

(60) Provisional application No. 61/494,774, filed on Jun. 8, 2011.

(51) Int. Cl.
*A61K 38/00* (2006.01)
*A61K 38/17* (2006.01)
*C07K 14/47* (2006.01)

(52) U.S. Cl.
CPC ........... *A61K 38/005* (2013.01); *A61K 38/1709* (2013.01); *C07K 14/4703* (2013.01); *A61K 38/00* (2013.01)

(58) Field of Classification Search
CPC ........ A61K 38/16; A61L 38/00; A61L 38/02; A61L 38/03; A61L 38/04
See application file for complete search history.

(56) References Cited

U.S. PATENT DOCUMENTS

| 7,067,642 | B1 | 6/2006 | Kato et al. |
| 2005/0004026 | A1 | 1/2005 | Kasibhatla et al. |
| 2007/0020687 | A1 | 1/2007 | Cheng et al. |
| 2007/0037165 | A1 | 2/2007 | Venter et al. |
| 2008/0107668 | A1 | 5/2008 | Philip et al. |
| 2010/0003257 | A1 | 1/2010 | Juan et al. |
| 2010/0215645 | A1 | 8/2010 | Cargill et al. |

FOREIGN PATENT DOCUMENTS

WO    WO 2012/166579    6/2012

OTHER PUBLICATIONS

Roy et al. (Molecular and Cellular Biology, Sep. 2005, p. 7940-7952).*
Dong; et al., "Silencing of IQGAP1 by shRNA inhibits the invasion of ovarian carcinoma HO-8910PM cells in vitro", Journal of Experimental & Clinical Cancer Research (Nov. 2008), 27:77, 8 pgs.
Fernandez; et al., "Actin-Capping Protein and the Hippo pathway regulate Factin and tissue growth in Drosophila", Development (Jun. 2011), 138(11):2337-2346.
Hayashi; et al., "Overexpression of IQGAP1 in advanced colorectal cancer correlates with poor prognosis-critical role in tumor invasion", International Journal of Cancer (Jun. 2010), 126(11):2563-2574.
Liu; et al., "IQGAP1 Plays an Important Role in the Invasiveness of Thyroid Cancer", Clinical Cancer Research (Dec. 2010), 16(24):6009-6018.
Roy; et al., "IQGAP1 Binds ERK2 and Modulates Its Activity", The Journal of Biological Chemistry (Apr. 2004), 279 (19):17329-17337.
Instituto Gulbenkian De Cienia, "Scientists Uncover Role for Cell Scaffold in Tumor Formation: Fruit Fly Reveals Surprising Link", ScienceDaily (Jun. 2011), 2 pgs.
Wang; et al., "IQGAP1 Regulates Cell Proliferation Through a Novel CDC42-mTOR Pathway", Journal of Cell Science (Jun. 2009), 122(Pt 12):2024-2033.
White; et al., "IQGAPs in Cancer: A Family of Scaffold Proteins Underlying Tumorigensis", FEBS Lett (Jun. 2009), 583(12):1817-1824.
Tang, Mei-Chuan et al., Thymosin beta 4 induces colon cancer cell migration and clinical metastasis via enhancing ILK/IQGAP1/Rac1 signal transduction pathway, Cancer Letters, pp. 162-171, vol. 308, No. 2, May 2, 2011, New York, New York, US.
Jameson Katherine et al., "IQGAP1 scaffold-kinase interaction blockade selectively targets RAS-MAP kinase-driven tumors.", National Institute of Health, May 2013, pp. 626-630, vol. 19, NR. 5, Nature Medicine.
Jadeski Lorraine et al: "IQGAP1 stimulates proliferation and enhances tumorigenesis of human breast epithelial cells.", Jan. 11, 2008, THE Journal of Biological Chemistry, Jan. 11, 2008, pp. 1008-1017, vol. 283, NR. 2.
Chen Feng et al: "IQGAP1 is overexpressed in hepatocellular carcinoma and promotes cell proliferation by Akt activation.", Experimental & Molecular Medicine Jul. 31, 2010, pp. 477-483, vol. 42, No. 7.

\* cited by examiner

*Primary Examiner* — James H Alstrum Acevedo
*Assistant Examiner* — Tara Martinez
(74) *Attorney, Agent, or Firm* — Bozicevic, Field & Francis LLP; Pamela J. Sherwood

(57) ABSTRACT

Aspects of the invention include compositions and methods for inhibiting the interaction between scaffold proteins and kinases. These compositions and methods find a number of uses including, for example, suppressing tumor growth and metastasis and reducing tumor size and number in a mammal with cancer.

4 Claims, 43 Drawing Sheets

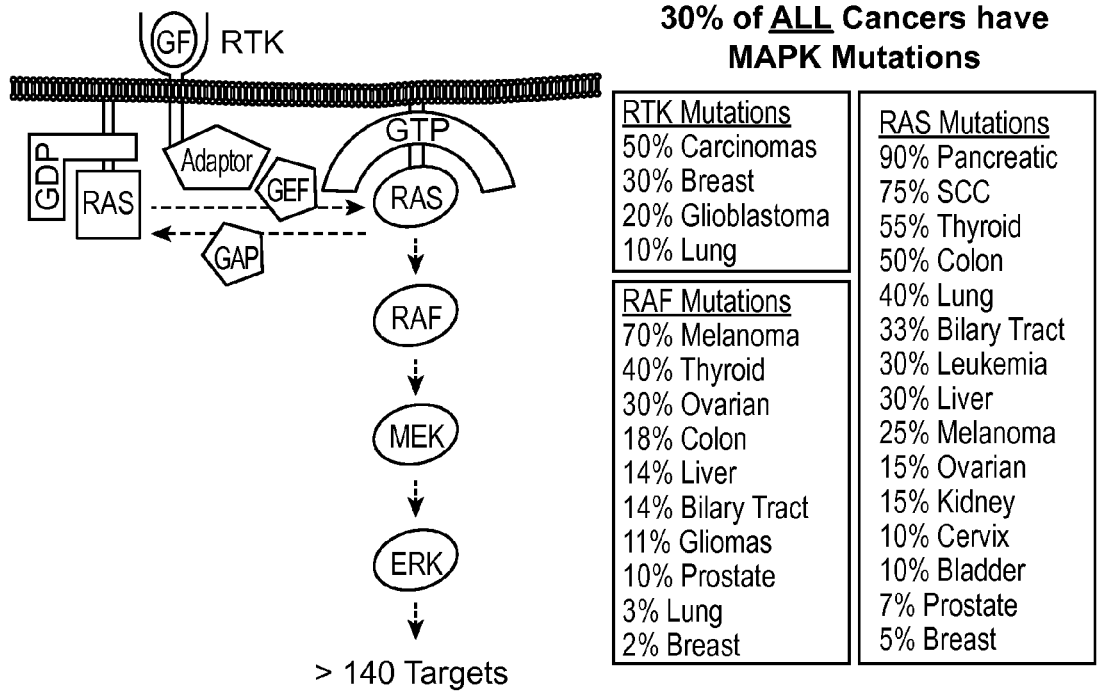
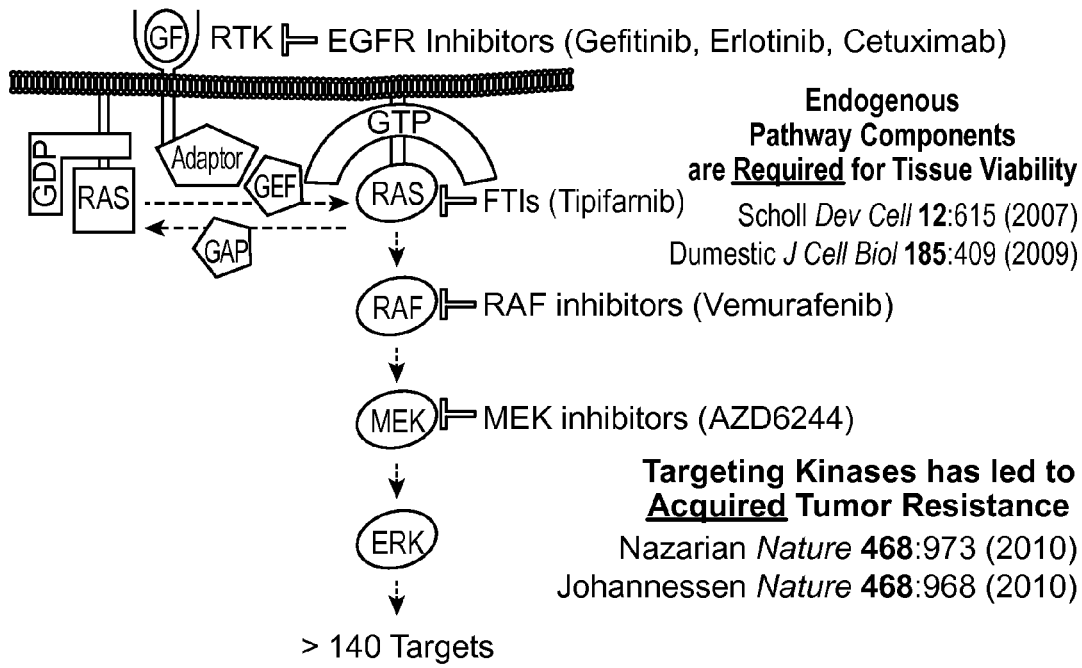
FIG. 1

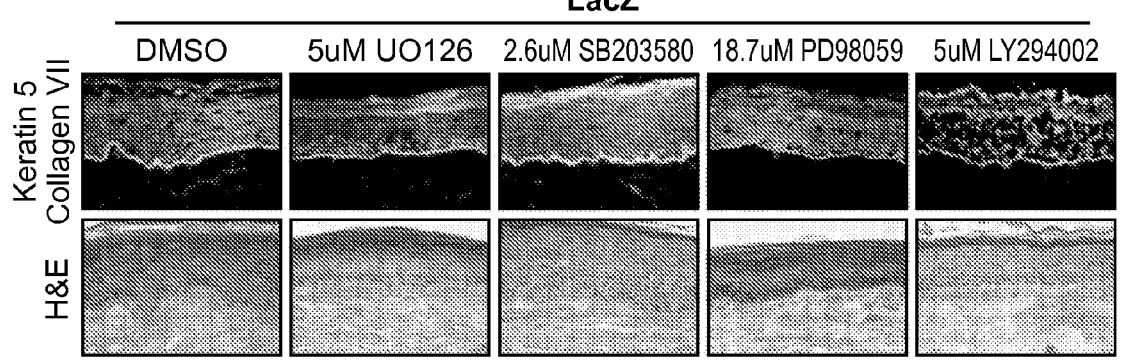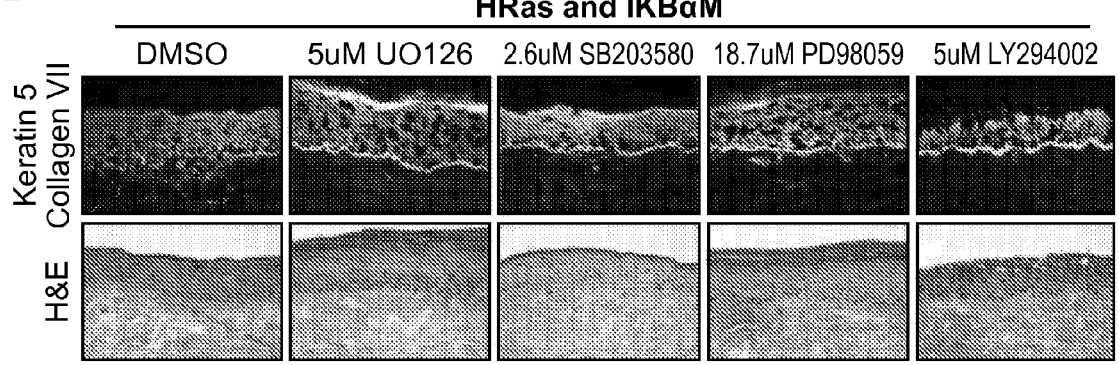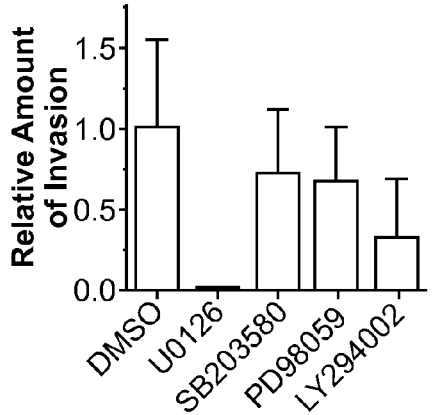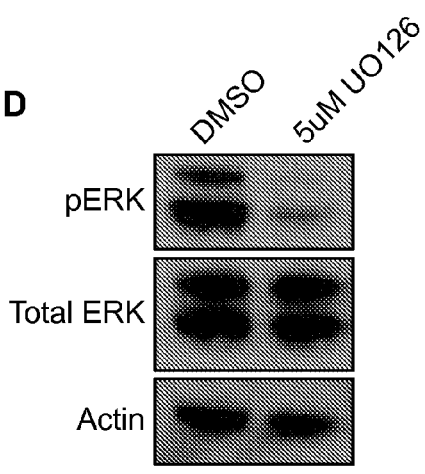
FIG. 2

| Scaffold | IQGAP1 | MEKK1 | KSR1 | MORG1 | ARB1 | ARB2 | MP1 |
|---|---|---|---|---|---|---|---|
| Full Name | IQ Motif Containing, GTPase activating protein 1 | MAPK/ERK kinase kinase 1 | Kinase suppressor of ras 1 | MAPK organizer 1 | Arestin beta 1 | Arestin beta 2 | Mek partner 1 |
| Identified | 1994 | 1993 | 1995 | 2004 | 1990 | 1992 | 1998 |
| Size | 190 kDa | 196 kDa | 140 kDa | 34 kDa | 47 kDa | 46 kDa | 14 kDa |
| ERK/MAPK Binding Partners | EGFR, RAF, MEK, and ERK | RAS and ERK | RAF, MEK, and ERK | RAF, MEK, and ERK | RAF, MEK, and ERK | RAF, MEK, and ERK | ERK and MEK |
| Additional Binding Partners | Cdc42, Rac1, actin, β-catenin, E-cadherin, and many others | Jnk, Cdc42, Rac1, 14-3-3, p53, and others | 14-3-3, C-TAK1 | p14, MP1, PHD3 | PI3K, AKT, Ral-GDS, and others | PI3K, AKT, Ral-GDS, and others | p14, MORG1, PAK1 |
| Localization | Plasma MB | Plasma MB | Plasma MB | Endosome | Plasma MB | Plasma MB | Late endomes and lysosomes |
| Possible Importance in Cancer | Overexpressed in many cancers | LOF results in diminished chemical-induced apoptosis | Overexpressed in some cancers | N/A | Required for colorecal carcinoma cell migration | Knockout leads to increased Lewis lung cancer tumor growth | Required for motility of DU145 prostate cancer cells |
| KO Mice | Overtly normal with late stage gastric hyperplasia, neuron migratory defects, and stimulated cardiac hypertrophy | Failure of embryonic eyelid closure at birth, slower wound healing | Develop tumors at a slower rate than WT | Embryonic lethal | Overtly normal with altered cardiac response following adrenergic stimulation | Desensitization of opiod receptors | N/A |
| References | 51, 52, 67, 74, 123 | 63, 64, 65, 66 | 39, 40, 154, 155, 156, 157 | 158, 159, 160 | 165, 166, 168, 170, 171 | 165, 167, 169, 170, 172 | 161, 162, 163, 164 |

FIG. 4

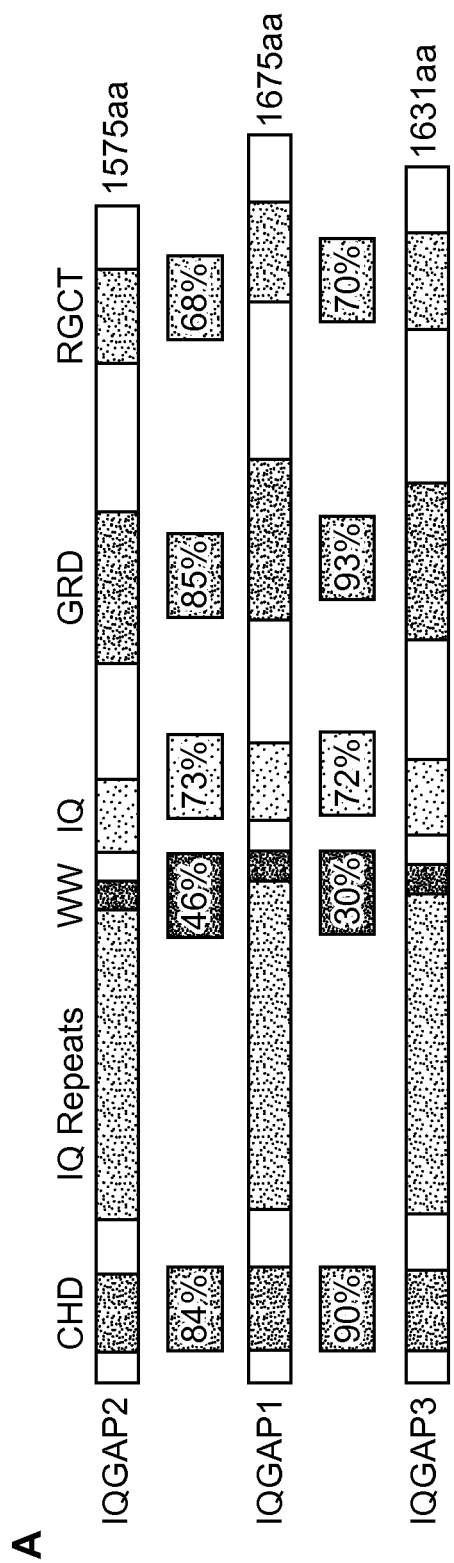
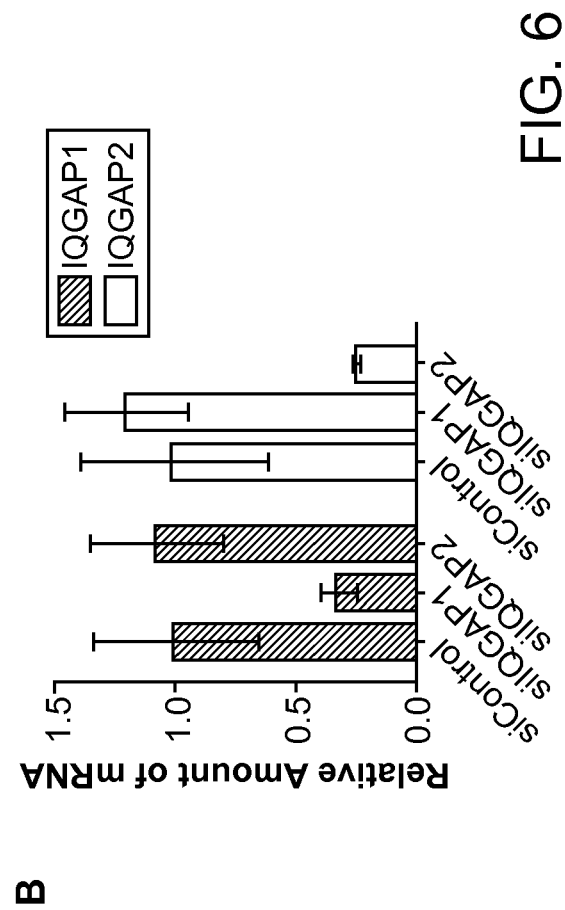
FIG. 6

B
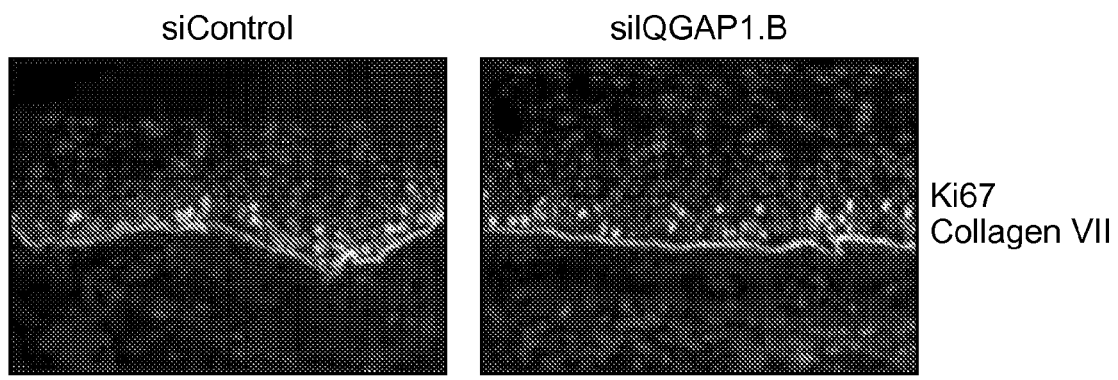
siControl     siIQGAP1.B
Ki67
Collagen VII
C
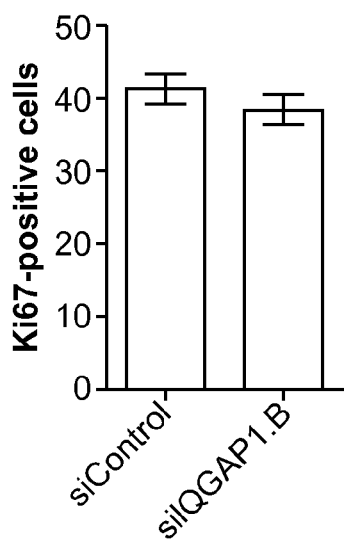
FIG. 8 (Cont.)

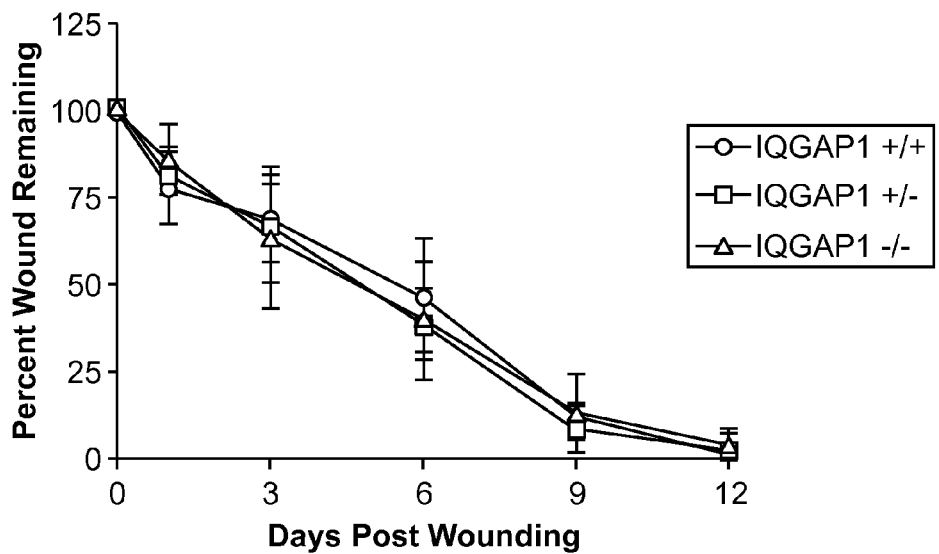
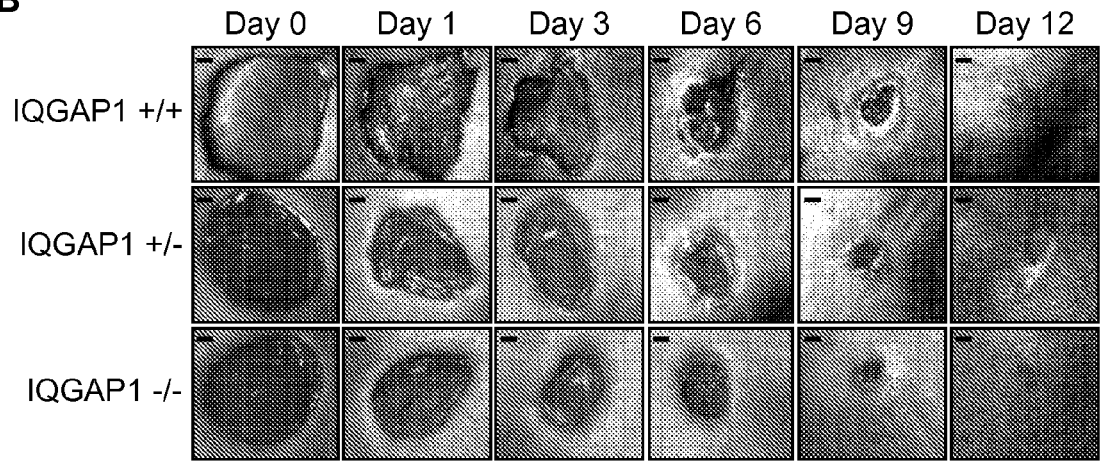
FIG. 10

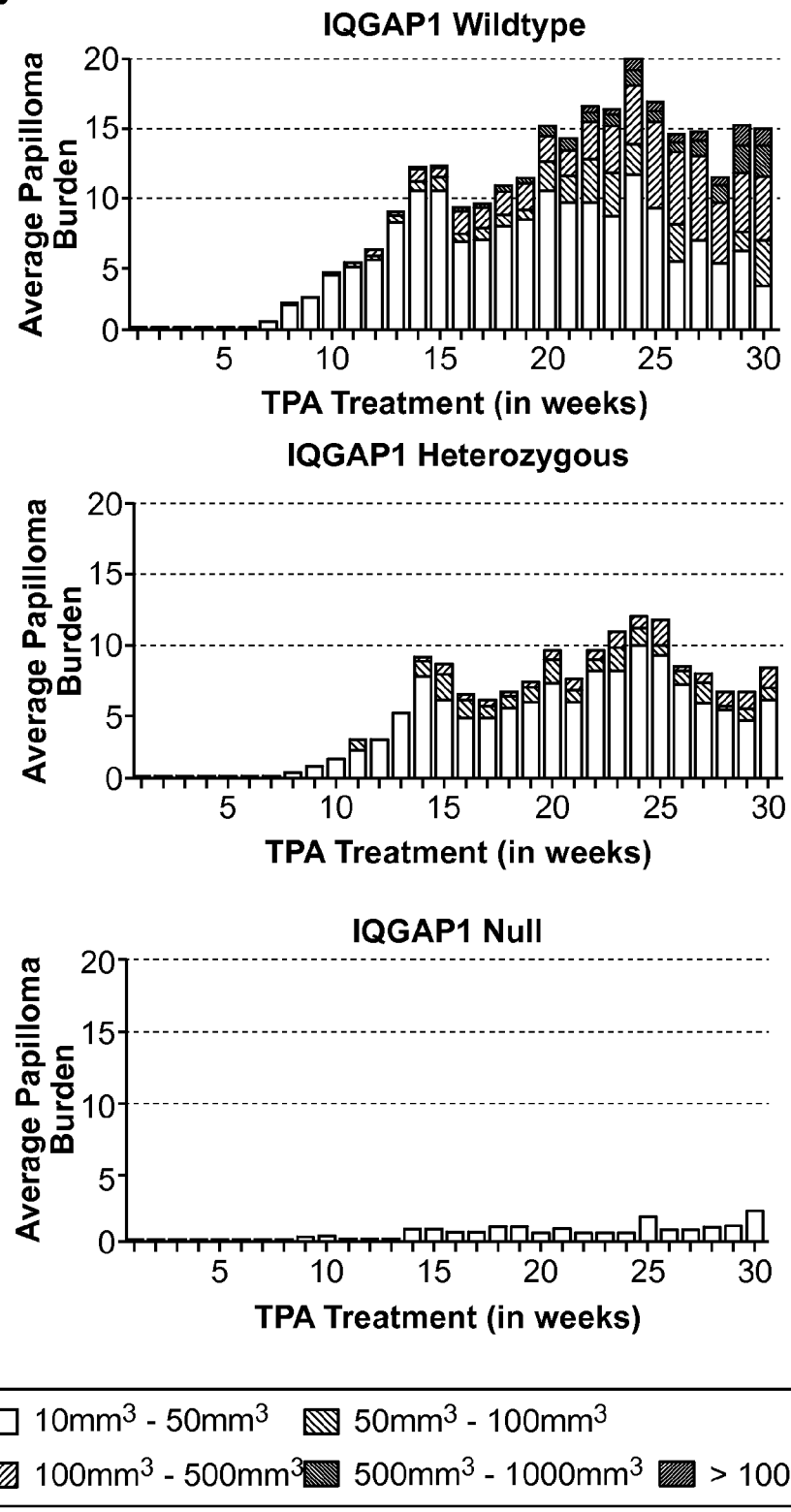
FIG. 12 (Cont. 1)

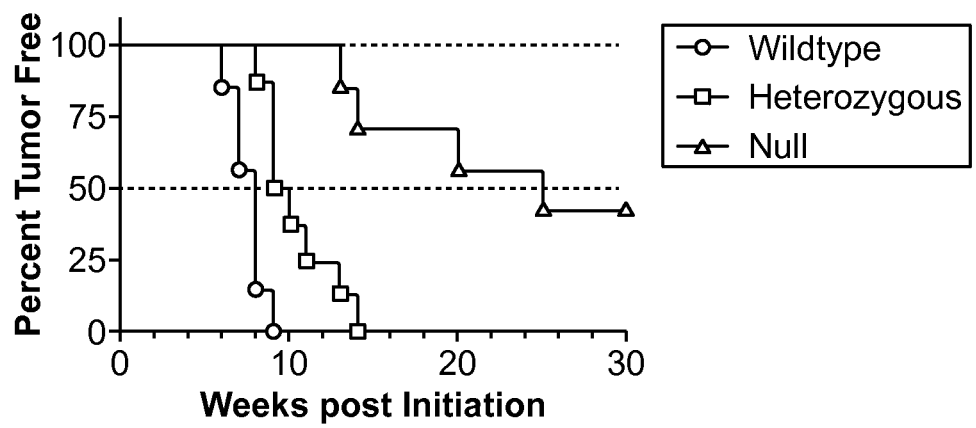
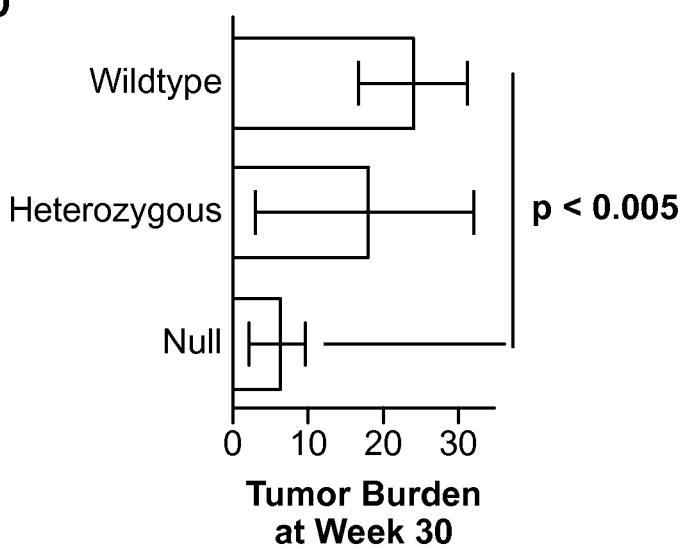
FIG. 12 (Cont. 2)

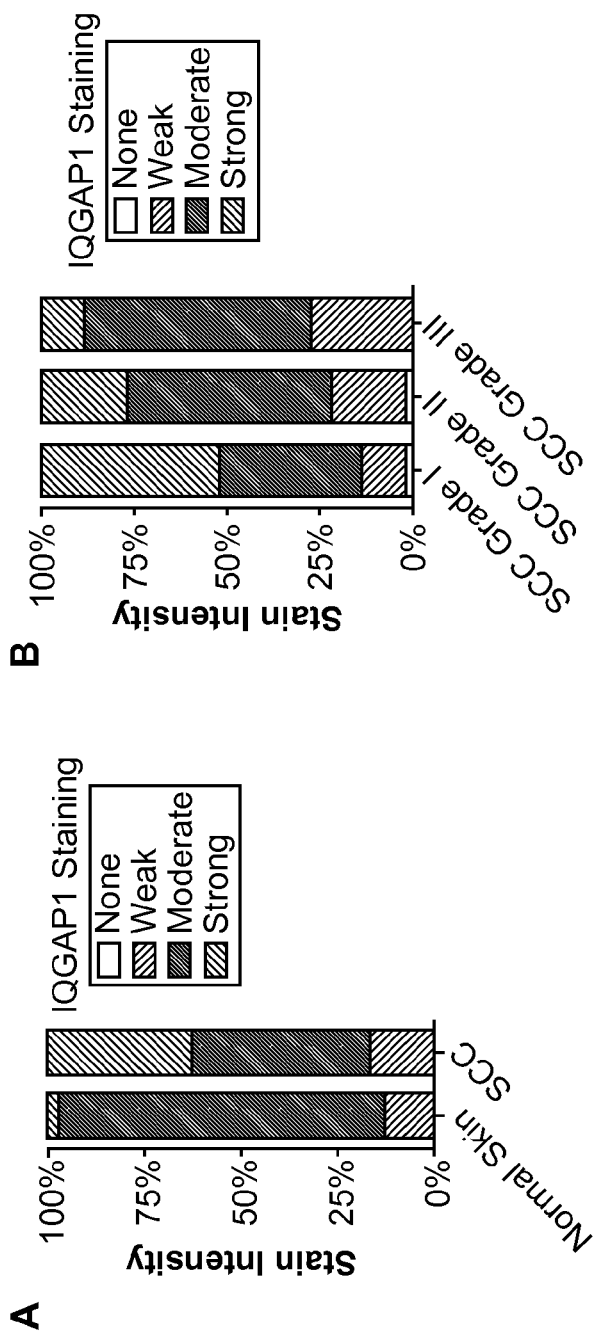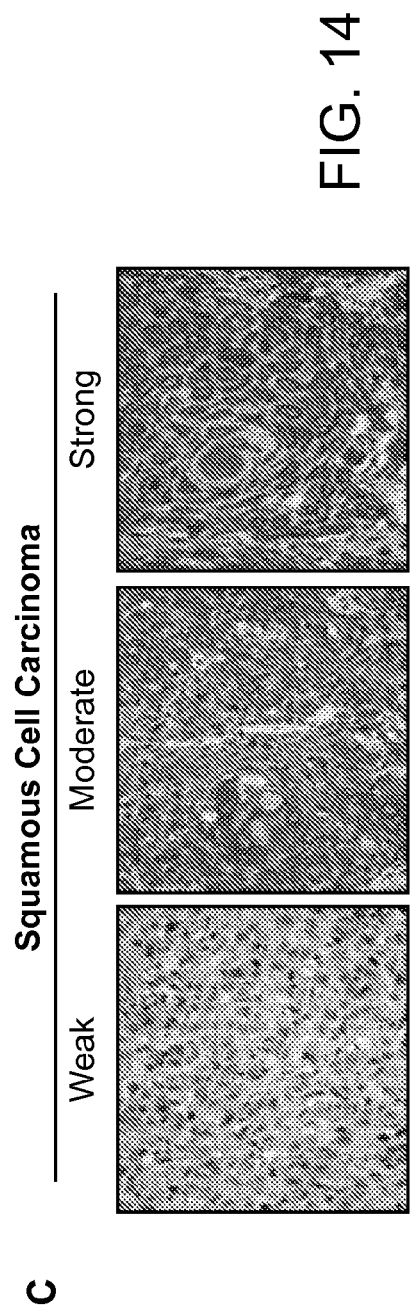
FIG. 14

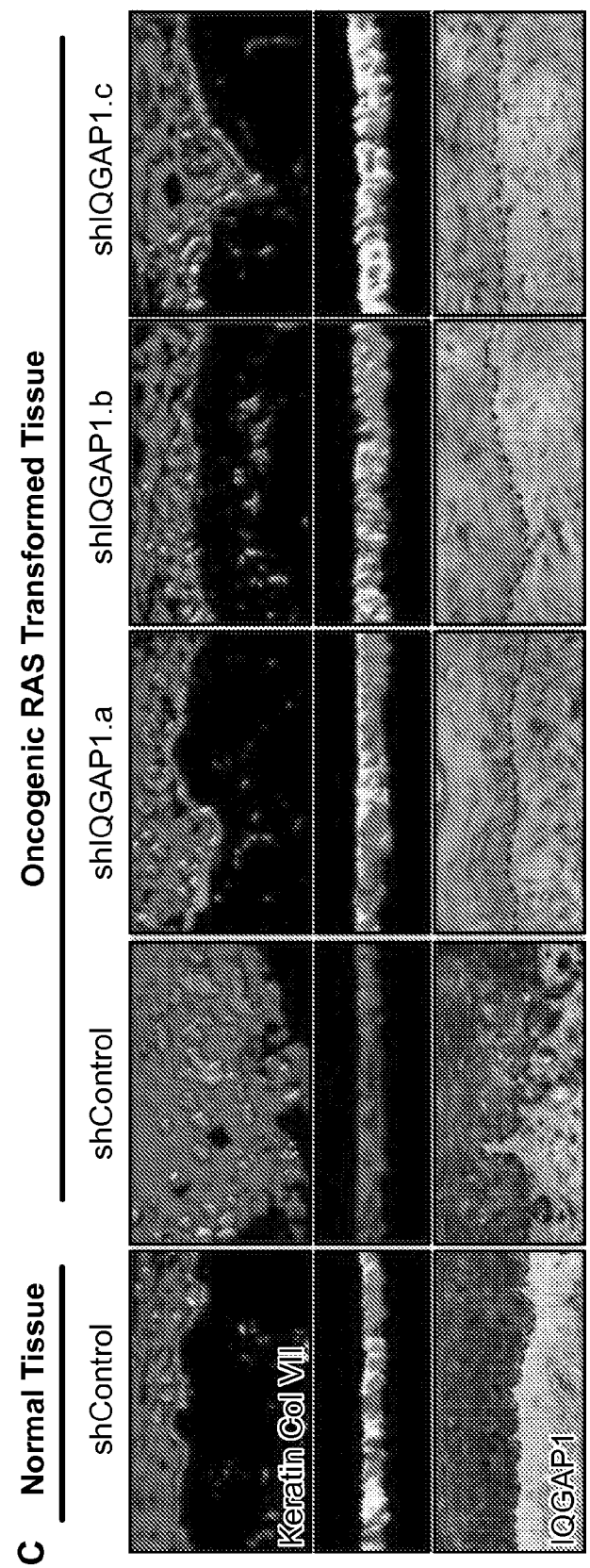
FIG. 15 (Cont. 1)

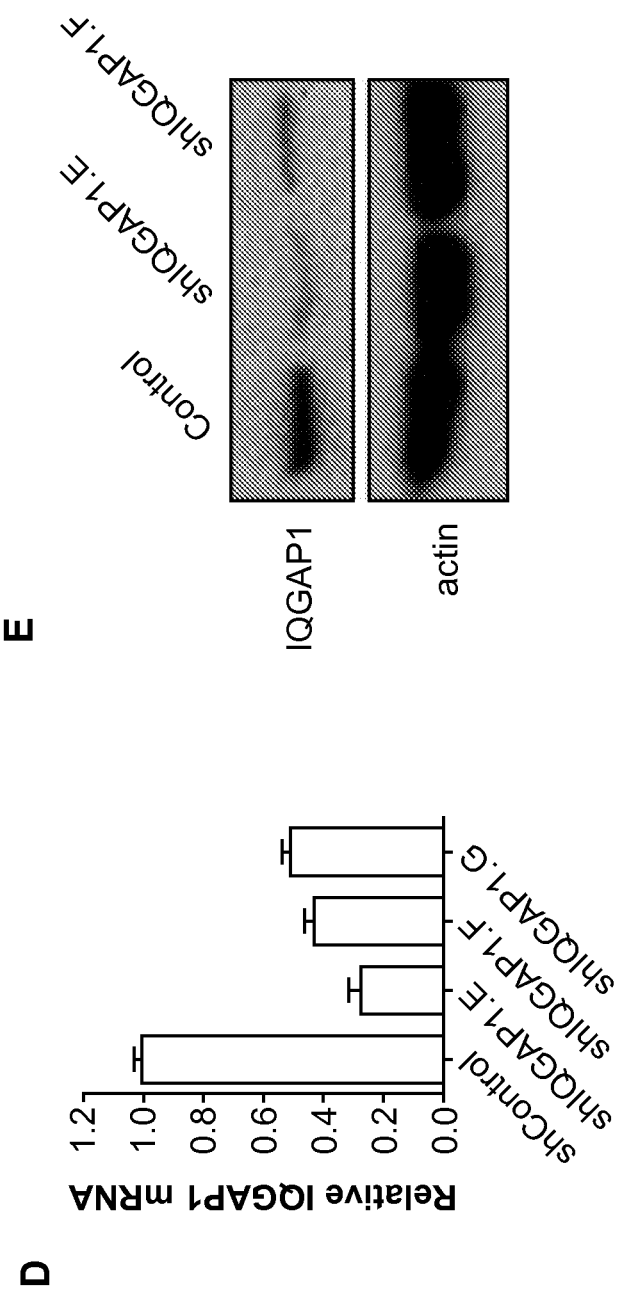
FIG. 15 (Cont. 2)

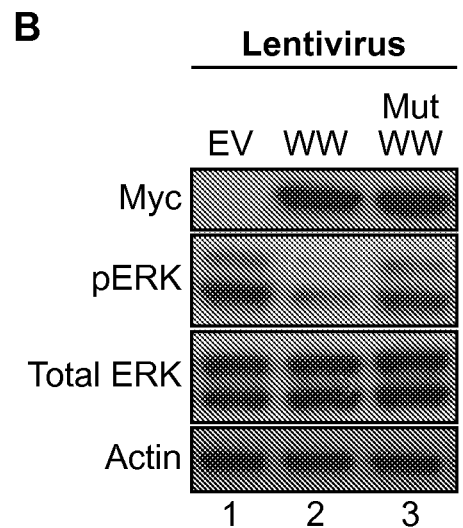
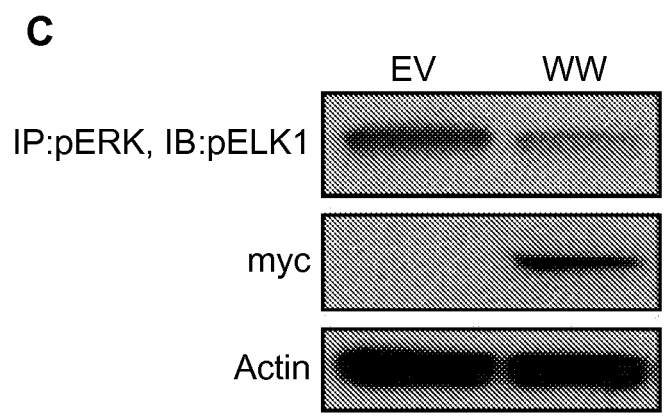
FIG. 20 (Cont.)

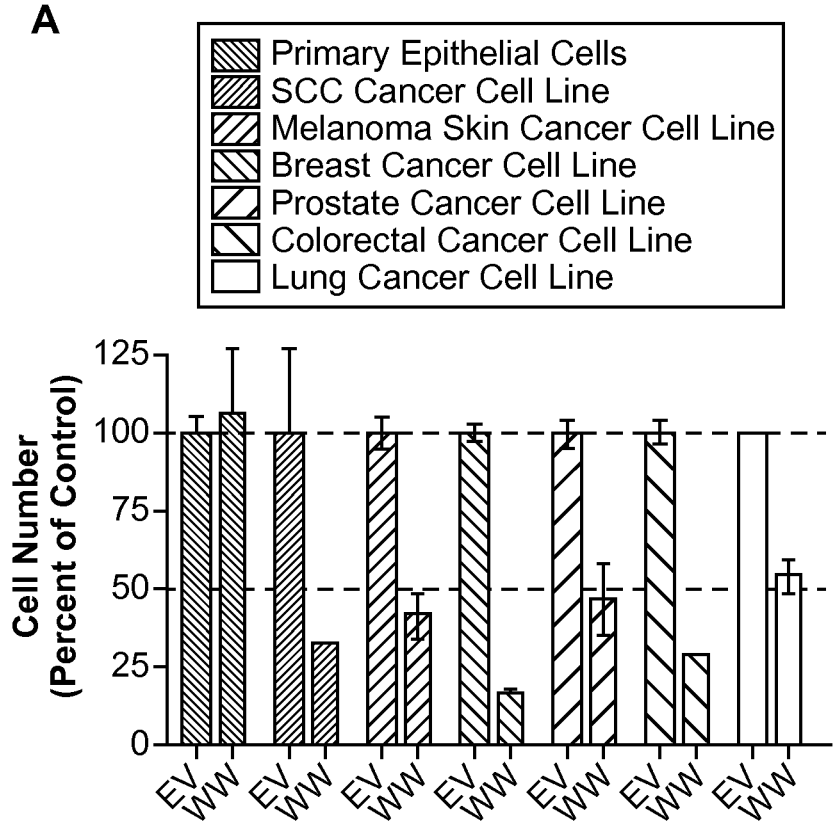
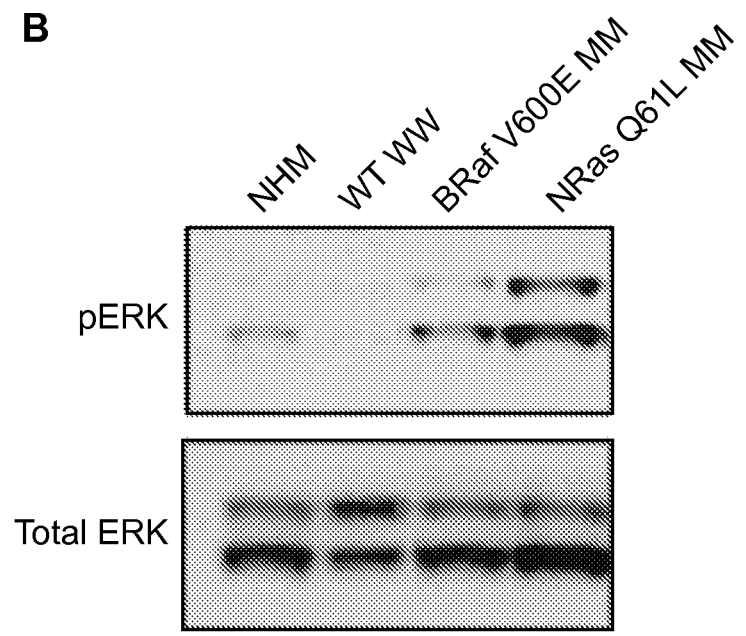
FIG. 21

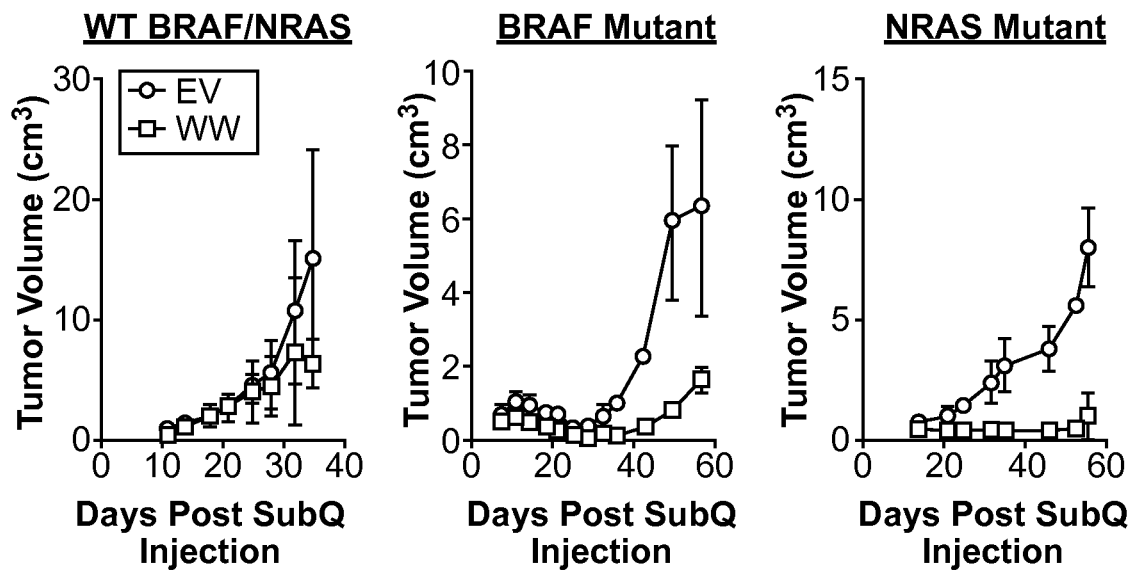
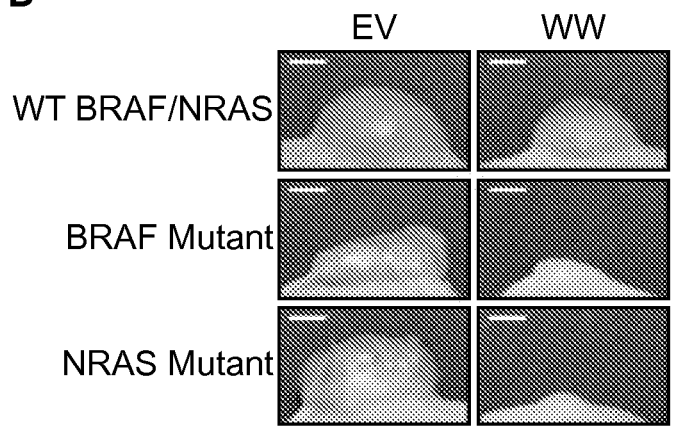
FIG. 21 (Cont. 1)

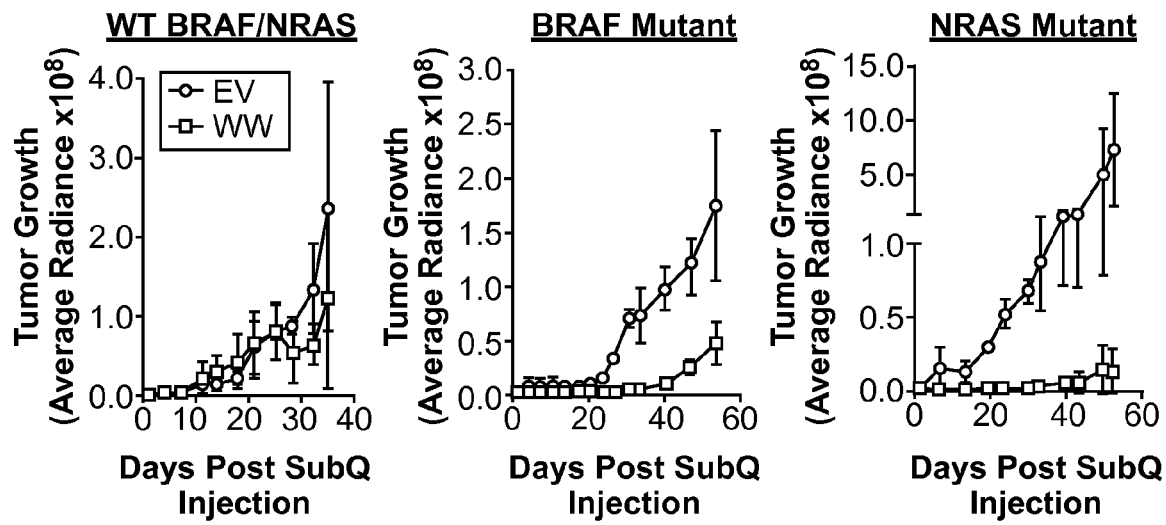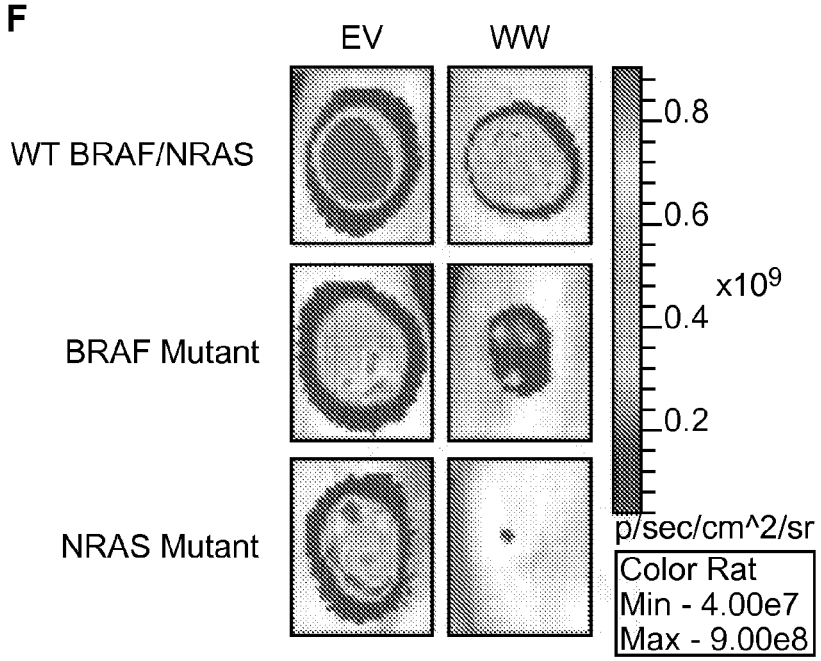
FIG. 21 (Cont. 2)

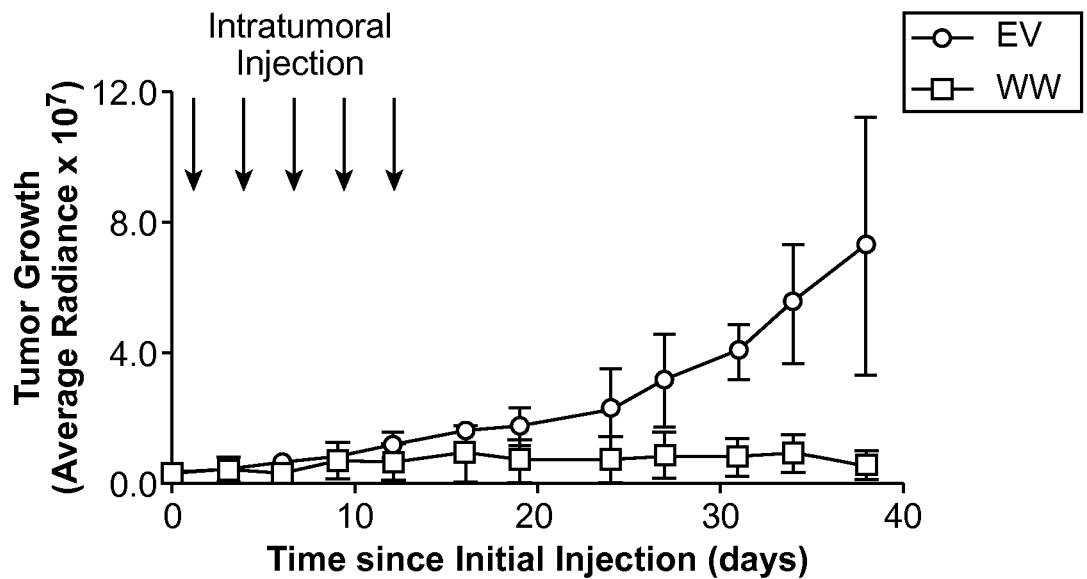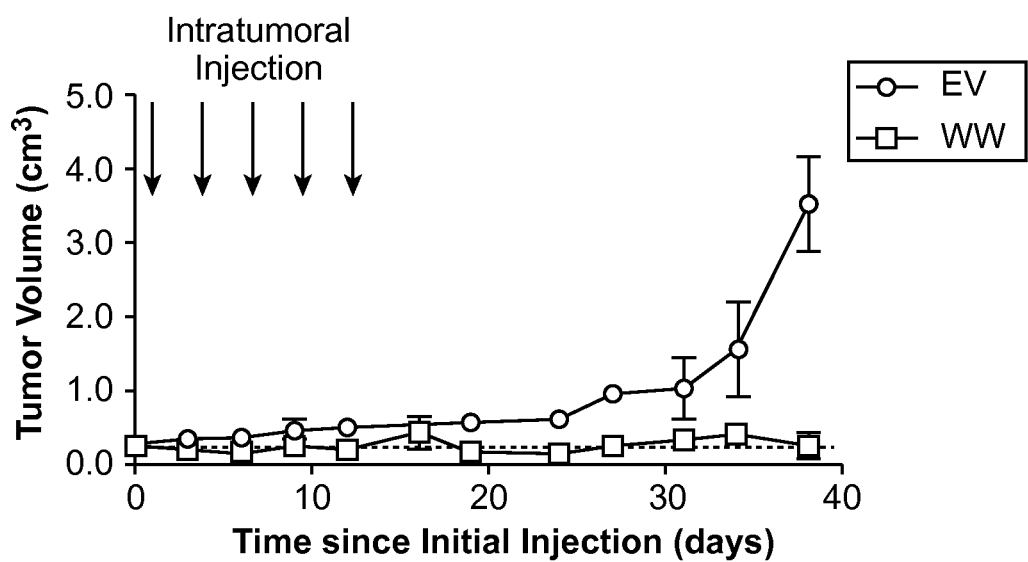
FIG. 22

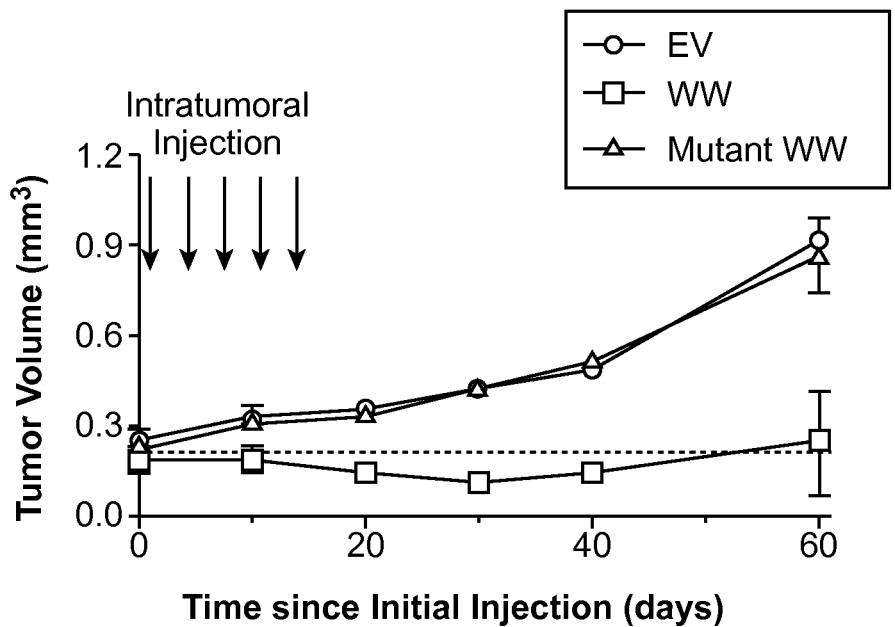
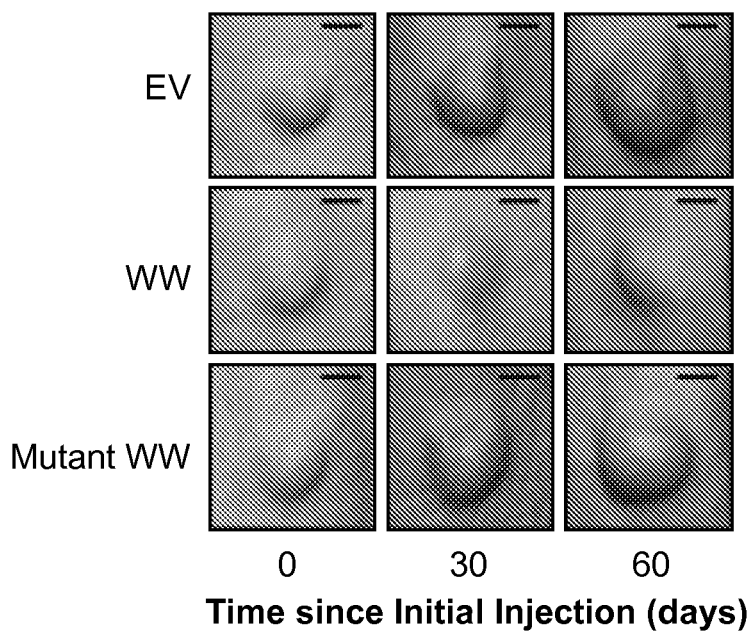
FIG. 23

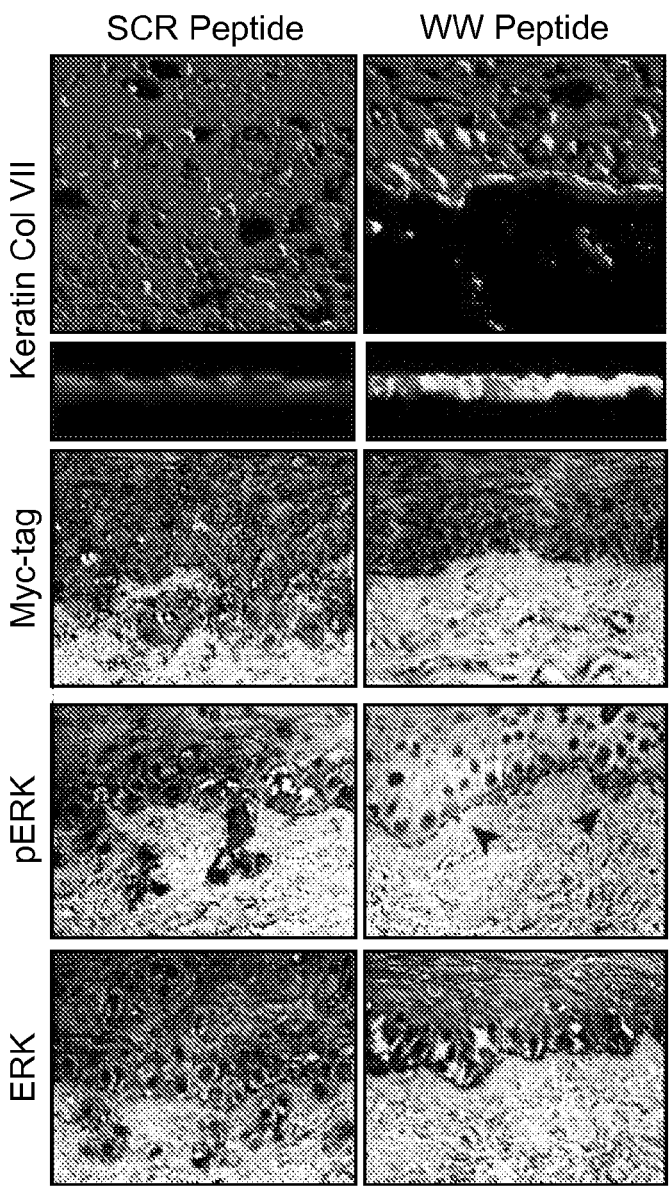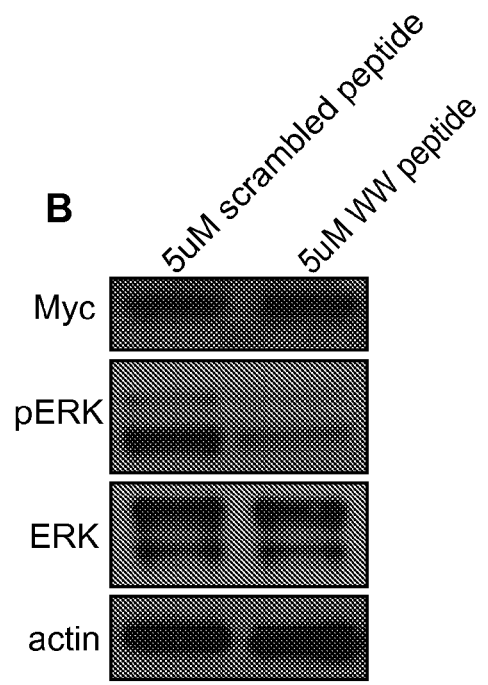
FIG. 24

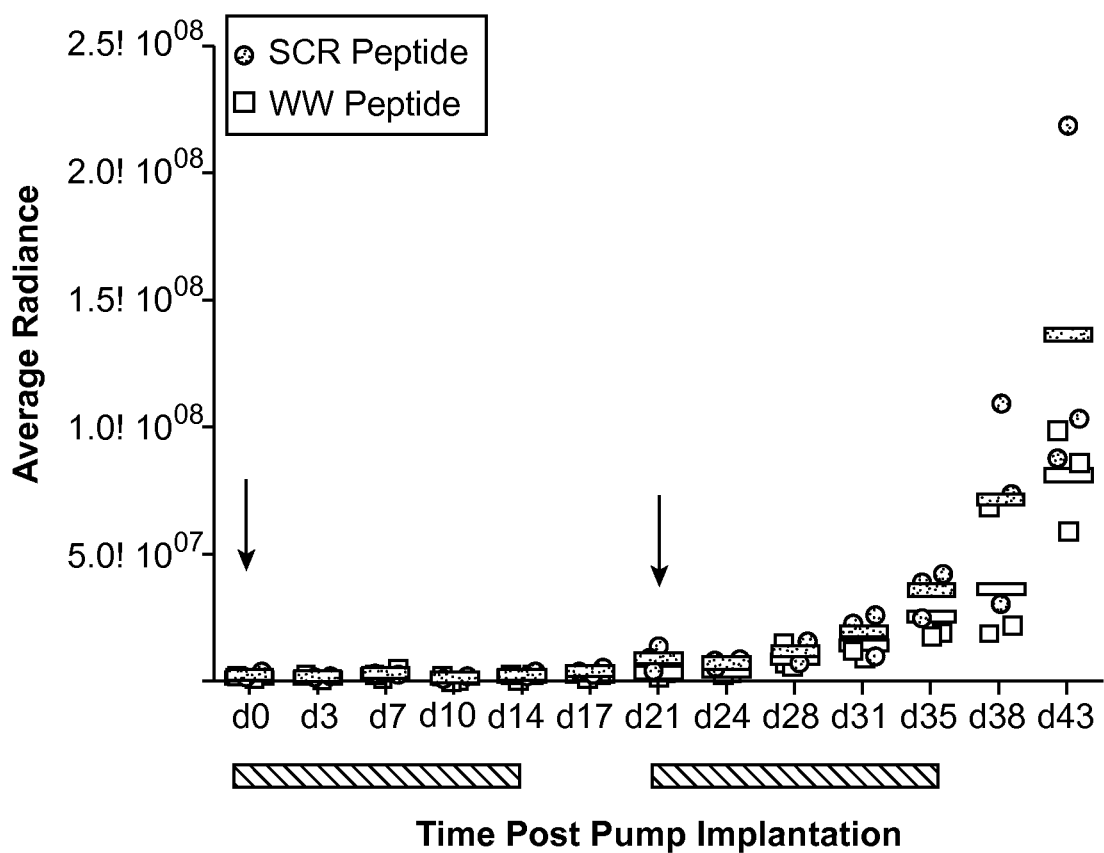
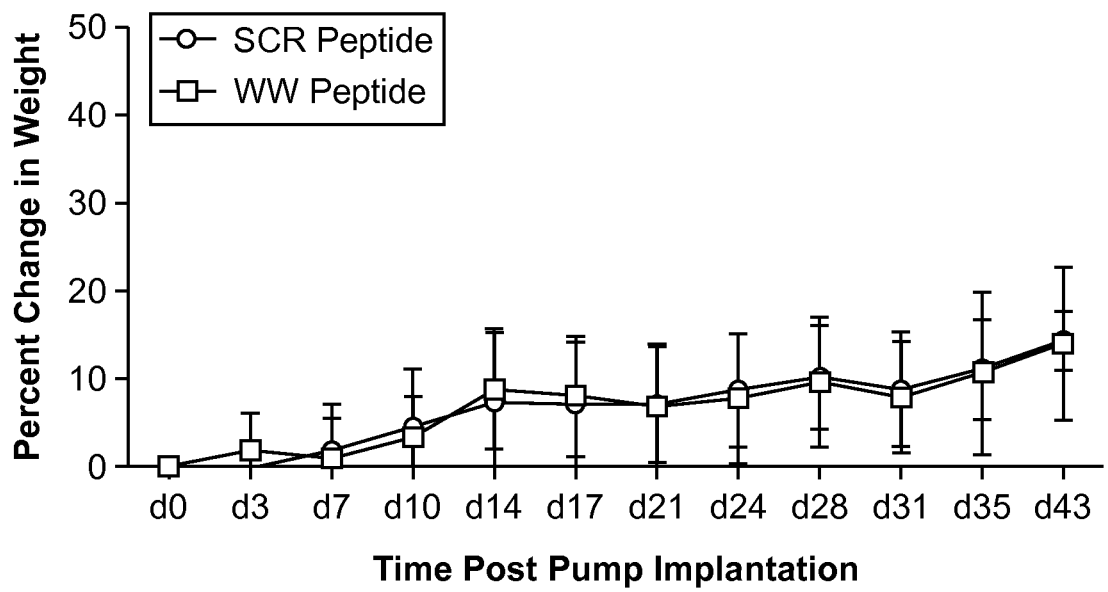
FIG. 27

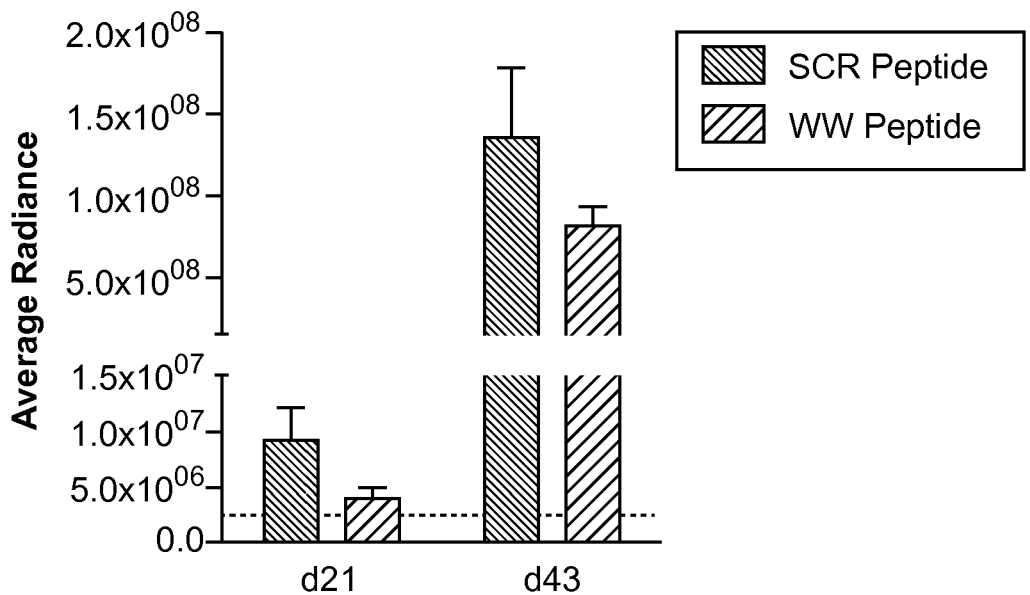
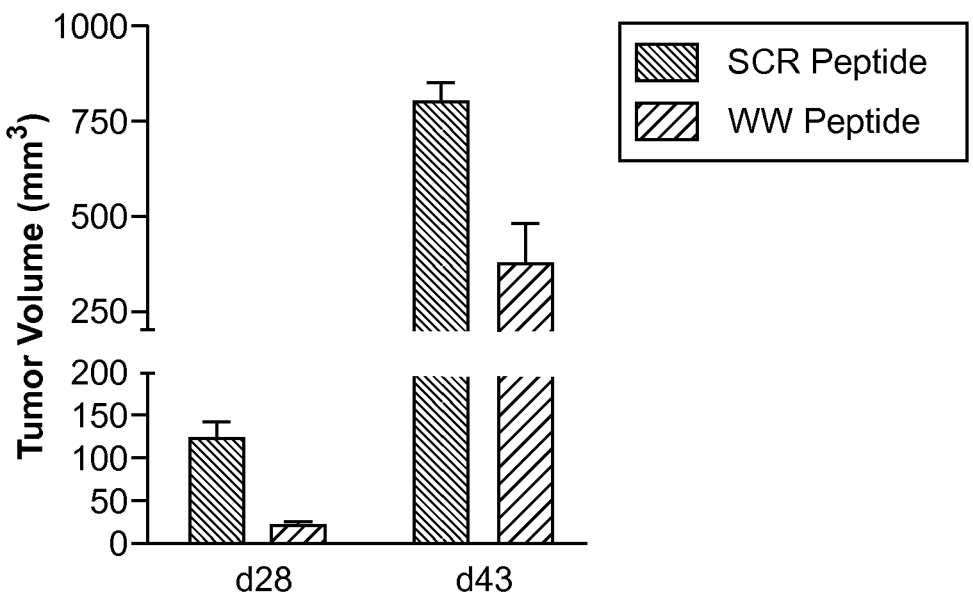
FIG. 27 (Cont.)

SEQUENCE LISTING

<160> NUMBER OF SEQ ID NOS: 62

<210> SEQ ID NO 1
<211> LENGTH: 32
<212> TYPE: PRT
<213> ORGANISM: Homo sapiens

<400> SEQUENCE: 1

Asp Asn Asn Ser Lys Trp Val Lys His Trp Val Lys Gly Gly Tyr Tyr
1               5                   10                  15

Tyr Tyr His Asn Leu Glu Thr Gln Glu Gly Gly Trp Asp Glu Pro Pro
            20                  25                  30

<210> SEQ ID NO 2
<211> LENGTH: 32
<212> TYPE: PRT
<213> ORGANISM: Chimp

<400> SEQUENCE: 2

Asp Asn Asn Ser Lys Trp Val Lys His Trp Val Lys Gly Gly Tyr Tyr
1               5                   10                  15

Tyr Tyr His Asn Leu Glu Thr Gln Glu Gly Gly Trp Asp Glu Pro Pro
            20                  25                  30

<210> SEQ ID NO 3
<211> LENGTH: 32
<212> TYPE: PRT
<213> ORGANISM: Rhesus

<400> SEQUENCE: 3

Asp Asn Asn Ser Lys Trp Val Lys His Trp Val Lys Gly Gly Tyr Tyr
1               5                   10                  15

Tyr Tyr His Asn Leu Glu Thr Gln Glu Gly Gly Trp Asp Glu Pro Pro
            20                  25                  30

<210> SEQ ID NO 4
<211> LENGTH: 32
<212> TYPE: PRT
<213> ORGANISM: Mouse

<400> SEQUENCE: 4

Asp Asn Asn Ser Lys Trp Val Lys His Trp Val Lys Gly Gly Tyr Tyr
1               5                   10                  15

His Tyr His Asn Leu Glu Thr Gln Ala Gly Gly Trp Ala Glu Pro Pro
            20                  25                  30

<210> SEQ ID NO 5
<211> LENGTH: 32
<212> TYPE: PRT
<213> ORGANISM: Rat

<400> SEQUENCE: 5

Asp Asn Asn Ser Lys Trp Val Lys His Trp Val Lys Gly Gly Tyr Tyr
1               5                   10                  15

His Tyr His Asn Leu Glu Thr Gln Ala Gly Gly Trp Ala Glu Pro Pro
            20                  25                  30

<210> SEQ ID NO 6
<211> LENGTH: 32
<212> TYPE: PRT
<213> ORGANISM: Cow

<400> SEQUENCE: 6

Asp Asn Asn Ser Lys Trp Val Lys His Trp Val Lys Gly Gly Tyr Tyr
1               5                   10                  15

His Tyr His Asn Leu Glu Thr Gln Glu Gly Gly Trp Asp Glu Pro Ser
            20                  25                  30

<210> SEQ ID NO 7
<211> LENGTH: 32
<212> TYPE: PRT
<213> ORGANISM: Opossum

<400> SEQUENCE: 7

Asp Asn Asn Ser Lys Trp Val Lys His Trp Val Lys Gly Gly Tyr Tyr
1               5                   10                  15

His Tyr His Asn Leu Glu Thr Gln Glu Gly Gly Trp Asp Glu Pro Ser
            20                  25                  30

<210> SEQ ID NO 8
<211> LENGTH: 32
<212> TYPE: PRT
<213> ORGANISM: Zebra Finch

<400> SEQUENCE: 8

Gly Asn Gly Ser Asp Trp Val Lys His Trp Val Arg Gly Gly Tyr Tyr
1               5                   10                  15

His Tyr His Asn Leu Arg Thr Lys Asp Gly Gly Trp Asp Glu Pro Ala
            20                  25                  30

<210> SEQ ID NO 9
<211> LENGTH: 32
<212> TYPE: PRT
<213> ORGANISM: Xenopus

<400> SEQUENCE: 9

Asp Asn Gly Ser Glu Trp Val Gln His Trp Val Lys Gly Gly Tyr Leu
1               5                   10                  15

Tyr Tyr Phe Asn Leu Ser Thr Asn Glu Gly Arg Trp Val Glu Pro Gln
            20                  25                  30

<210> SEQ ID NO 10
<211> LENGTH: 32
<212> TYPE: PRT
<213> ORGANISM: Zebra fish

<400> SEQUENCE: 10

Asp Asn Gly Ser Glu Trp Met Glu His Trp Val Lys Gly Gly His Asn
1               5                   10                  15

Tyr Tyr Tyr Asn Leu Lys Thr Gly Gln Gly Thr Trp Asp Lys Pro Ala
            20                  25                  30

<210> SEQ ID NO 11
<211> LENGTH: 21
<212> TYPE: RNA
<213> ORGANISM: Artificial Sequence
<220> FEATURE:
<223> OTHER INFORMATION: Synthetic Ribonucleotide

<400> SEQUENCE: 11
gaacguggcu uaugaguacu u                                           21

<210> SEQ ID NO 12
<211> LENGTH: 21
<212> TYPE: RNA

<213> ORGANISM: Artificial Sequence
<220> FEATURE:
<223> OTHER INFORMATION: Synthetic Ribonucleotide

<400> SEQUENCE: 12
guacucauaa gccacguucu u                                    21

<210> SEQ ID NO 13
<211> LENGTH: 25
<212> TYPE: RNA
<213> ORGANISM: Artificial Sequence
<220> FEATURE:
<223> OTHER INFORMATION: Synthetic Ribonucleotide

<400> SEQUENCE: 13
ccucucgcuc ugaugggaca uuugu                                25

<210> SEQ ID NO 14
<211> LENGTH: 25
<212> TYPE: RNA
<213> ORGANISM: Artificial Sequence
<220> FEATURE:
<223> OTHER INFORMATION: Synthetic Ribonucleotide

<400> SEQUENCE: 14
acaaaugucc caucagagcg agagg                                25

<210> SEQ ID NO 15
<211> LENGTH: 25
<212> TYPE: RNA
<213> ORGANISM: Artificial Sequence
<220> FEATURE:
<223> OTHER INFORMATION: Synthetic Ribonucleotide

<400> SEQUENCE: 15
cagccaucau gacauuuacc augaa                                25

<210> SEQ ID NO 16
<211> LENGTH: 25
<212> TYPE: RNA
<213> ORGANISM: Artificial Sequence
<220> FEATURE:
<223> OTHER INFORMATION: Synthetic Ribonucleotide

<400> SEQUENCE: 16
uucaugguaa augucaugau ggcug                                25

<210> SEQ ID NO 17
<211> LENGTH: 21
<212> TYPE: RNA
<213> ORGANISM: Artificial Sequence
<220> FEATURE:
<223> OTHER INFORMATION: Synthetic Ribonucleotide

<400> SEQUENCE: 17
gauuagaugu caauacagau u                                    21

<210> SEQ ID NO 18
<211> LENGTH: 21
<212> TYPE: RNA
<213> ORGANISM: Artificial Sequence
<220> FEATURE:
<223> OTHER INFORMATION: Synthetic Ribonucleotide

<400> SEQUENCE: 18
ucuguauuga caucuaaucu u                                    21

<210> SEQ ID NO 19
<211> LENGTH: 21
<212> TYPE: RNA
<213> ORGANISM: Artificial Sequence
<220> FEATURE:
<223> OTHER INFORMATION: Synthetic Ribonucleotide

<400> SEQUENCE: 19
agaaagaggu gaugaacuau u                                              21

<210> SEQ ID NO 20
<211> LENGTH: 21
<212> TYPE: RNA
<213> ORGANISM: Artificial Sequence
<220> FEATURE:
<223> OTHER INFORMATION: Synthetic Ribonucleotide

<400> SEQUENCE: 20
uaguucauca ccucuuucuu u                                              21

<210> SEQ ID NO 21
<211> LENGTH: 21
<212> TYPE: RNA
<213> ORGANISM: Artificial Sequence
<220> FEATURE:
<223> OTHER INFORMATION: Synthetic Ribonucleotide

<400> SEQUENCE: 21
ugaacacggu gcaguuuaau u                                              21

<210> SEQ ID NO 22
<211> LENGTH: 21
<212> TYPE: RNA
<213> ORGANISM: Artificial Sequence
<220> FEATURE:
<223> OTHER INFORMATION: Synthetic Ribonucleotide

<400> SEQUENCE: 22
uuaaacugca ccguguucau u                                              21

<210> SEQ ID NO 23
<211> LENGTH: 21
<212> TYPE: RNA
<213> ORGANISM: Artificial Sequence
<220> FEATURE:
<223> OTHER INFORMATION: Synthetic Ribonucleotide

<400> SEQUENCE: 23
gaacugcccu ucacccuaau u                                              21

<210> SEQ ID NO 24
<211> LENGTH: 21
<212> TYPE: RNA
<213> ORGANISM: Artificial Sequence
<220> FEATURE:
<223> OTHER INFORMATION: Synthetic Ribonucleotide

<400> SEQUENCE: 24
uuagggugaa gggcaguucu u                                              21

<210> SEQ ID NO 25
<211> LENGTH: 21
<212> TYPE: RNA
<213> ORGANISM: Artificial Sequence
<220> FEATURE:

<223> OTHER INFORMATION: Synthetic Ribonucleotide

<400> SEQUENCE: 25
cggcguagac uuugagauuu u                                              21

<210> SEQ ID NO 26
<211> LENGTH: 21
<212> TYPE: RNA
<213> ORGANISM: Artificial Sequence
<220> FEATURE:
<223> OTHER INFORMATION: Synthetic Ribonucleotide

<400> SEQUENCE: 26
aaucucaaag ucuacgcggu u                                              21

<210> SEQ ID NO 27
<211> LENGTH: 21
<212> TYPE: RNA
<213> ORGANISM: Artificial Sequence
<220> FEATURE:
<223> OTHER INFORMATION: Synthetic Ribonucleotide

<400> SEQUENCE: 27
cggaugaccu aaagcgauuu u                                              21

<210> SEQ ID NO 28
<211> LENGTH: 21
<212> TYPE: RNA
<213> ORGANISM: Artificial Sequence
<220> FEATURE:
<223> OTHER INFORMATION: Synthetic Ribonucleotide

<400> SEQUENCE: 28
aaucguuuua ggucauccgu u                                              21

<210> SEQ ID NO 29
<211> LENGTH: 21
<212> TYPE: RNA
<213> ORGANISM: Artificial Sequence
<220> FEATURE:
<223> OTHER INFORMATION: Synthetic Ribonucleotide

<400> SEQUENCE: 29
gaccggaugu uaaccuuuau u                                              21

<210> SEQ ID NO 30
<211> LENGTH: 21
<212> TYPE: RNA
<213> ORGANISM: Artificial Sequence
<220> FEATURE:
<223> OTHER INFORMATION: Synthetic Ribonucleotide

<400> SEQUENCE: 30
uaaagguuaa cauccggucu u                                              21

<210> SEQ ID NO 31
<211> LENGTH: 21
<212> TYPE: RNA
<213> ORGANISM: Artificial Sequence
<220> FEATURE:
<223> OTHER INFORMATION: Synthetic Ribonucleotide

<400> SEQUENCE: 31
guacagggcu ccagaaauuu u                                              21

```
<210> SEQ ID NO 32
<211> LENGTH: 21
<212> TYPE: RNA
<213> ORGANISM: Artificial Sequence
<220> FEATURE:
<223> OTHER INFORMATION: Synthetic Ribonucleotide

<400> SEQUENCE: 32
aauuucugga gcccuguacu u                                              21

<210> SEQ ID NO 33
<211> LENGTH: 24
<212> TYPE: DNA
<213> ORGANISM: Artificial Sequence
<220> FEATURE:
<223> OTHER INFORMATION: Synthetic Oglionucleotide

<400> SEQUENCE: 33
ttcgccacta cccagacctt gttt                                           24

<210> SEQ ID NO 34
<211> LENGTH: 23
<212> TYPE: DNA
<213> ORGANISM: Artificial Sequence
<220> FEATURE:
<223> OTHER INFORMATION: Synthetic Oglionucleotide

<400> SEQUENCE: 34
cctgtcttgg atgtggcctt tgg                                            23

<210> SEQ ID NO 35
<211> LENGTH: 24
<212> TYPE: DNA
<213> ORGANISM: Artificial Sequence
<220> FEATURE:
<223> OTHER INFORMATION: Synthetic Oglionucleotide

<400> SEQUENCE: 35
ttcaacctca ggacagacct ccat                                           24

<210> SEQ ID NO 36
<211> LENGTH: 24
<212> TYPE: DNA
<213> ORGANISM: Artificial Sequence
<220> FEATURE:
<223> OTHER INFORMATION: Synthetic Oglionucleotide

<400> SEQUENCE: 36
actggcctcg ttcatagctg ttca                                           24

<210> SEQ ID NO 37
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 37
agcaagtccc atgagtctca                                                20

<210> SEQ ID NO 38
<211> LENGTH: 20
<212> TYPE: DNA
<213> ORGANISM: Artificial Sequence
<220> FEATURE:
<223> OTHER INFORMATION: Synthetic Oglionucleotide
```

```
<400> SEQUENCE: 38
caacctgcaa tgcttgcact                                              20

<210> SEQ ID NO 39
<211> LENGTH: 24
<212> TYPE: DNA
<213> ORGANISM: Artificial Sequence
<220> FEATURE:
<223> OTHER INFORMATION: Synthetic Oglionucleotide

<400> SEQUENCE: 39
cagaccgatt taaggctgca agca                                         24

<210> SEQ ID NO 40
<211> LENGTH: 24
<212> TYPE: DNA
<213> ORGANISM: Artificial Sequence
<220> FEATURE:
<223> OTHER INFORMATION: Synthetic Oglionucleotide

<400> SEQUENCE: 40
tccacattaa atcgtacggc tcgc                                         24

<210> SEQ ID NO 41
<211> LENGTH: 24
<212> TYPE: DNA
<213> ORGANISM: Artificial Sequence
<220> FEATURE:
<223> OTHER INFORMATION: Synthetic Oglionucleotide

<400> SEQUENCE: 41
aggcatgaag gatgacaagg agga                                         24

<210> SEQ ID NO 42
<211> LENGTH: 24
<212> TYPE: DNA
<213> ORGANISM: Artificial Sequence
<220> FEATURE:
<223> OTHER INFORMATION: Synthetic Oglionucleotide

<400> SEQUENCE: 42
aatcctgagg ccagaggttc atca                                         24

<210> SEQ ID NO 43
<211> LENGTH: 24
<212> TYPE: DNA
<213> ORGANISM: Artificial Sequence
<220> FEATURE:
<223> OTHER INFORMATION: Synthetic Oglionucleotide

<400> SEQUENCE: 43
ggagaggtga gggcaggatt aaga                                         24

<210> SEQ ID NO 44
<211> LENGTH: 23
<212> TYPE: DNA
<213> ORGANISM: Artificial Sequence
<220> FEATURE:
<223> OTHER INFORMATION: Synthetic Oglionucleotide

<400> SEQUENCE: 44
gtatgaacac agcttgccac cca                                          23

<210> SEQ ID NO 45
<211> LENGTH: 24
```

```
<212> TYPE: DNA
<213> ORGANISM: Artificial Sequence
<220> FEATURE:
<223> OTHER INFORMATION: Synthetic Oglionucleotide

<400> SEQUENCE: 45
gcatgctttg cgacctggtt tctt                                        24

<210> SEQ ID NO 46
<211> LENGTH: 24
<212> TYPE: DNA
<213> ORGANISM: Artificial Sequence
<220> FEATURE:
<223> OTHER INFORMATION: Synthetic Oglionucleotide

<400> SEQUENCE: 46
tagtcctgta ttggcactgc tgct                                        24

<210> SEQ ID NO 47
<211> LENGTH: 23
<212> TYPE: DNA
<213> ORGANISM: Artificial Sequence
<220> FEATURE:
<223> OTHER INFORMATION: Synthetic Oglionucleotide

<400> SEQUENCE: 47
gaagagagag accctcactg ctg                                         23

<210> SEQ ID NO 48
<211> LENGTH: 23
<212> TYPE: DNA
<213> ORGANISM: Artificial Sequence
<220> FEATURE:
<223> OTHER INFORMATION: Synthetic Oglionucleotide

<400> SEQUENCE: 48
actgtgagga ggggagattc agt                                         23

<210> SEQ ID NO 49
<211> LENGTH: 21
<212> TYPE: DNA
<213> ORGANISM: Artificial Sequence
<220> FEATURE:
<223> OTHER INFORMATION: Synthetic Oglionucleotide

<400> SEQUENCE: 49
tgaccctgaa gttcatctgc a                                           21

<210> SEQ ID NO 50
<211> LENGTH: 21
<212> TYPE: DNA
<213> ORGANISM: Artificial Sequence
<220> FEATURE:
<223> OTHER INFORMATION: Synthetic Oglionucleotide

<400> SEQUENCE: 50
tcttgtagtt gccgtcgtcc t                                           21

<210> SEQ ID NO 51
<211> LENGTH: 19
<212> TYPE: DNA
<213> ORGANISM: Artificial Sequence
<220> FEATURE:
<223> OTHER INFORMATION: Synthetic Oglionucleotide

<400> SEQUENCE: 51
```

```
ttgcagtctg tggcatgtg                                              19
```

<210> SEQ ID NO 52
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 52

```
cctgctgaca ggtcaatgat                                             20
```

<210> SEQ ID NO 53
<211> LENGTH: 19
<212> TYPE: DNA
<213> ORGANISM: Artificial Sequence
<220> FEATURE:
<223> OTHER INFORMATION: Synthetic Oglionucleotide

<400> SEQUENCE: 53

```
ttgcagtctg tggcatgtg                                              19
```

<210> SEQ ID NO 54
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 54

```
cctgctcttt actgaaggct                                             20
```

<210> SEQ ID NO 55
<211> LENGTH: 26
<212> TYPE: DNA
<213> ORGANISM: Artificial Sequence
<220> FEATURE:
<223> OTHER INFORMATION: Synthetic Oglionucleotide

<400> SEQUENCE: 55

```
caccaccagc tccacttcag cacatt                                      26
```

<210> SEQ ID NO 56
<211> LENGTH: 26
<212> TYPE: DNA
<213> ORGANISM: Artificial Sequence
<220> FEATURE:
<223> OTHER INFORMATION: Synthetic Oglionucleotide

<400> SEQUENCE: 56

```
cgcaccaacg tgtagaaggc atcctc                                      26
```

<210> SEQ ID NO 57
<211> LENGTH: 75
<212> TYPE: DNA
<213> ORGANISM: Artificial Sequence
<220> FEATURE:
<223> OTHER INFORMATION: Synthetic Oglionucleotide

<400> SEQUENCE: 57

```
gctcgcggat ccaccatgga acaaaaactt atttctgaag aagatctgga taataacagc   60
aagtgggtga agcac                                                  75
```

<210> SEQ ID NO 58
<211> LENGTH: 44

<212> TYPE: DNA
<213> ORGANISM: Artificial Sequence
<220> FEATURE:
<223> OTHER INFORMATION: Synthetic Oglionucleotide

<400> SEQUENCE: 58
ataagtgcgg ccgcttatgg gggttcatcc catcctcctt cctg                44

<210> SEQ ID NO 59
<211> LENGTH: 52
<212> TYPE: DNA
<213> ORGANISM: Artificial Sequence
<220> FEATURE:
<223> OTHER INFORMATION: Synthetic Oglionucleotide

<400> SEQUENCE: 59
ggtgaagcac tgggtaaaag gtggatatta tgctgcccac aatctggaga cc          52

<210> SEQ ID NO 60
<211> LENGTH: 52
<212> TYPE: DNA
<213> ORGANISM: Artificial Sequence
<220> FEATURE:
<223> OTHER INFORMATION: Synthetic Oglionucleotide

<400> SEQUENCE: 60
ggtctccaga ttgtgggcag cataatatcc acctttacc cagtgcttca cc           52

<210> SEQ ID NO 61
<211> LENGTH: 7219
<212> TYPE: DNA
<213> ORGANISM: Homo sapiens

<400> SEQUENCE: 61
ggaccccggc aagcccgcgc acttggcagg agctgtagct accgccgtcc gcgcctccaa    60
ggtttcacgg cttcctcagc agagactcgg gctcgtccgc catgtccgcc gcagacgagg   120
ttgacgggct gggcgtggcc cggccgcact atggctctgt cctggataat gaaagactta   180
ctgcagagga gatggatgaa aggagacgtc agaacgtggc ttatgagtac ctttgtcatt   240
tggaagaagc gaagaggtgg atggaagcat gcctagggga agatctgcct cccaccacag   300
aactggagga ggggcttagg aatggggtct accttgccaa actggggaac ttcttctctc   360
ccaaagtagt gtccctgaaa aaatctatg atcgagaaca gaccagatac aaggcgactg    420
gcctccactt tagacacact gataatgtga ttcagtggtt gaatgccatg gatgagattg   480
gattgcctaa gatttttttac ccagaaacta cagatatcta tgatcgaaag aacatgccaa   540
gatgtatcta ctgtatccat gcactcagtt tgtacctgtt caagctaggc ctggcccctc   600
agattcaaga cctatatgga aaggttgact tcacagaaga gaaatcaac aacatgaaga   660 ctgagttgga gaagtatggc atccagatgc ctgcctttag caagattggg gcatcttgg    720 ctaatgaact gtcagtggat gaagccgcat tacatgctgc tgttattgct attaatgaag   780
ctattgaccg tagaattcca gccgacacat ttgcagcttt gaaaaatccg aatgccatgc   840
ttgtaaatct tgaagagccc ttggcatcca cttaccagga tatactttac caggctaagc   900
aggacaaaat gacaaatgct aaaaacagga cagaaaactc agagagagaa agatgtgttt    960
atgaggagct gctcacgcaa gctgaaattc aaggcaatat aaacaaagtc aatacatttt    1020
ctgcattagc aaatatcgac ctggctttag aacaaggaga tgcactggcc ttgttcaggg   1080
ctctgcagtc accagcccctg ggcttcgag gactgcagca acagaatagc gactggtact   1140

```
tgaagcagct cctgagtgat aaacagcaga agagacagag tggtcagact gacccctgc     1200 agaaggagga gctgcagtct ggagtggatg ctgcaaacag tgctgcccag caatatcaga    1260
gaagattggc agcagtagca ctgattaatg ctgcaatcca aagggtgtt gctgagaaga     1320 ctgttttgga actgatgaat cccgaagccc agctgcccca ggtgtatcca tttgccgccg    1380
atctctatca aaggagctg ctaccctgc agcgacaaag tcctgaacat aatctcaccc      1440
acccagagct ctctgtcgca gtggagatgt tgtcatcggt ggccctgatc aacagggcat    1500
tggaatcagg agatgtgaat acagtgtgga agcaattgag cagttcagtt actggtctta    1560
ccaatattga ggaagaaaac tgtcagaggt atctcgatga gttgatgaaa ctgaaggctc    1620
aggcacatgc agagaataat gaattcatta catggaatga tatccaagct tgcgtggacc    1680
atgtgaacct ggtggtgcaa aggaacatg agaggatttt agccattggt ttaattaatg     1740
aagccctgga tgaaggtgat gcccaaaaga ctctgcaggc cctacagatt cctgcagcta    1800
aacttgaggg agtccttgca gaagtggccc agcattacca agacacgctg attagagcga    1860
agagagagaa agcccaggaa atccaggatg agtcagctgt gttatggttg gatgaaattc    1920
aaggtggaat ctgcagtcc aacaaagaca cccaagaagc acagaagttt gccttaggaa      1980
tctttgccat taatgaggca gtagaaagtg gtgatgttgg caaaacactg agtgcccttc    2040
gctcccctga tgttggcttg tatggagtca tccctgagtg tggtgaaaact taccacagtg    2100 atcttgctga agccaagaag aaaaaactgg cagtaggaga taataacagc aagtgggtga     2160 agcactggt aaaaggtgga tattattatt accacaatct ggagacccag gaaggaggat      2220
gggatgaacc tccaaatttt gtgcaaaatt ctatgcagct ttctcgggag gagatccaga    2280
gttctatctc tggggtgact gccgcatata accgagaaca gctgtggctg ccaatgaag      2340 gcctgatcac caggctgcag gctcgctgcc gtggatactt agttcgacag gaattccgat    2400
ccaggatgaa tttcctgaag aaacaaatcc ctgccatcac ctgcattcag tcacagtgga    2460
gaggatacaa gcagaagaag gcatatcaag atcggttagc ttacctgcgc tcccacaaag    2520
atgaagttgt aaagattcag tccctggcaa ggatgcacca agctcgaaag cgctatcgag    2580
atcgcctgca gtacttccgg gaccatataa atgacattat caaaatccag gcttttattc    2640
gggcaaacaa agctcgggat gactacaaga ctctcatcaa tgctgaggat cctcctatgg    2700
ttgtggtccg aaaatttgtc cacctgctgg accaaagtga ccaggatttt caggaggagc    2760
ttgaccttat gaagatgcgg gaagaggtta tcaccctcat tcgttctaac cagcagctgg    2820
agaatgacct caatctcatg gatatcaaaa ttggactgct agtgaaaaat aagattacgt    2880
tgcaggatgt ggtttcccac agtaaaaaac ttaccaaaaa aataaggaa cagttgtctg      2940 atatgatgat gataaataaa cagaagggag gtctcaaggc tttgagcaag gagaagagag    3000
agaagttgga agcttaccag cacctgtttt atttattgca aaccaatccc acctatctgg    3060
ccaagctcat ttttcagatg ccccagaaca agtccaccaa gttcatggac tctgtaatct    3120
tcacactcta caactacgcg tccaaccagc gagaggagta cctgctcctg cggctctttta    3180 agacagcact ccaagaggaa atcaagtcga aggtagatca gattcaagag attgtgacag    3240
gaaatcctac ggttattaaa atggttgtaa gtttcaaccg tggtgcccgt ggccagaatg    3300
ccctgagaca gatcttggcc ccagtcgtga aggaaattat ggatgacaaa tctctcaaca    3360
tcaaaactga ccctgtggat atttacaaat cttgggttaa tcagatggag tctcagacag    3420
gagaggcaag caaactgccc tatgatgtga ccctgagcac ggcgctagct catgaagaag    3480
tgaagacacg gctagacagc tccatcagga acatgcgggc tgtgacagac aagtttctct    3540
```

```
cagccattgt cagctctgtg gacaaaatcc cttatgggat gcgcttcatt gccaaagtgc    3600
tgaaggactc gttgcatgag aagttccctg atgctggtga ggatgagctg ctgaagatta    3660
ttggtaactt gctttattat cgatacatga atccagccat tgttgctcct gatgcctttg    3720
acatcattga cctgtcagca ggaggccagc ttaccacaga ccaacgccga aatctgggct    3780
ccattgcaaa aatgcttcag catgctgctt ccaataagat gtttctggga gataatgccc    3840
acttaagcat cattaatgaa tatctttccc agtcctacca gaaattcaga cggttttcc     3900 aaactgcttg tgatgtccca gagcttcagg ataaatttaa tgtggatgag tactctgatt    3960
tagtaaccct caccaaacca gtaatctaca tttccattgg tgaaatcatc aacacccaca    4020
ctctcctgtt ggatcaccag gatgccattg ctccggagca caatgatcca atccacgaac    4080
tgctggacga cctcggcgag gtgcccacca tcgagtccct gatagggggaa agctctggca    4140 atttaaatga cccaaataag gaggcactgg ctaagacgga agtgtctctc accctgacca    4200
acaagttcga cgtgcctgga gatgagaatg cagaaatgga tgctcgaacc atcttactga    4260
atacaaaacg tttaattgtg gatgtcatcc ggttccagcc aggagagacc ttgactgaaa    4320
tcctagaaac accagccacc agtgaacagg aagcagaaca tcagagagcc atgcagagac    4380
gtgctatccg tgatgccaaa acacctgaca agatgaaaaa gtcaaaatct gtaaaggaag    4440
acagcaacct cactcttcaa gagaagaaag agaagatcca gacaggttta agaagctaa     4500 cagagcttgg aaccgtggac ccaaagaaca ataccagga actgatcaac gacattgcca    4560
gggatattcg gaatcagcgg aggtaccgac agaggagaaa ggccgaacta gtgaaactgc    4620
aacagacata cgctgctctg aactctaagg ccacctttta tgggagcag gtggattact     4680 ataaaagcta tcaaaaacc tgcttggata acttagccag caaggggcaaa gtctccaaaa    4740 agcctaggga aatgaaagga aagaaaagca aaagatttc tctgaaatat acagcagcaa    4800
gactacatga aaaaggagtt cttctggaaa ttgaggacct gcaagtgaat cagtttaaaa    4860
atgttatatt tgaaatcagt ccaacagaag aagttggaga cttcgaagtg aaagccaaat    4920
tcatgggagt tcaaatggag acttttatgt tacattatca ggacctgctg cagctacagt    4980
atgaaggagt tgcagtcatg aaattatttg atagagctaa agtaaatgtc aacctcctga    5040
tcttccttct caacaaaaag ttctacggga gtaattgat cgtttgctgc agcccagaa      5100 ggatgaagga aagaagcacc tcacagctcc tttctaggtc cttctttcct cattggaagc    5160
aaagacctag ccaacaacag cacctcaatc tgatacactc ccgatgccac atttttaact    5220
cctctcgctc tgatgggaca tttgttaccc tttttcata gtgaaattgt gtttcaggct     5280
tagtctgacc tttctggttt cttcattttc ttccattact taggaaagag tggaaactcc    5340
actaaaattt ctctgtgttg ttacagtctt agaggttgca gtactatatt gtaagctttg    5400
gtgtttgttt aattagcaat agggatggta ggattcaaat gtgtgtcatt tagaagtgga    5460
agctattagc accaatgaca taaatacata caagacacac aactaaaatg tcatgttatt    5520
aacagttatt aggttgtcat ttaaaaataa agttccttta tatttctgtc ccatcaggaa    5580
aactgaagga tatggggaat cattggttat cttccattgt gttttctctt atggacagga    5640
gctaatggaa gtgacagtca tgttcaaagg aagcatttct agaaaaaagg agataatgtt    5700
tttaaatttc attatcaaac ttgggcaatt ctgtttgtgt aactccccga ctagtggatg    5760
ggagagtccc attgctaaaa ttcagctact cagataaatt cagaatgggt caaggcacct    5820
gcctgttttt gttggtgcac agagattgac ttgattcaga gagacaattc actccatccc    5880
```

| | |
|---|---|
| tatggcagag gaatgggtta gccctaatgt agaatgtcat tgttttaaa actgttttat | 5940 |
| atcttaagag tgccttatta aagtatagat gtatgtctta aaatgtgggt gataggaatt | 6000 |
| ttaaagattt atataatgca tcaaaagcct tagaataaga aaagcttttt ttaaattgct | 6060 |
| ttatctgtat atctgaactc ttgaaactta tagctaaaac actaggattt atctgcagtg | 6120 |
| ttcagggaga taattctgcc tttaattgtc taaaacaaaa acaaaaccag ccaacctatg | 6180 |
| ttacacgtga gattaaaacc aattttttcc ccatttttc tccttttttc tcttgctgcc | 6240 |
| cacattgtgc ctttatttta tgagcccag ttttctgggc ttagtttaaa aaaaaaatca | 6300 |
| agtctaaaca ttgcatttag aaagcttttg ttcttggata aaaagtcata cactttaaaa | 6360 |
| aaaaaaaaaa cttttccag gaaatatat tgaaatcatg ctgctgagcc tctatttct | 6420 |
| ttctttgatg ttttgattca gtattctttt atcataaatt tttagcattt aaaaattcac | 6480 |
| tgatgtacat taagccaata aactgcttta atgaataaca aactatgtag tgtgtcccta | 6540 |
| ttataaatgc attggagaag tattttatg agactcttta ctcaggtgca tggttacagc | 6600 |
| ccacagggag gcatggagtg ccatggaagg attcgccact acccagacct tgttttttgt | 6660 |
| tgtattttgg aagacaggtt ttttaaagaa acatttttcct cagattaaaa gatgatgcta | 6720 |
| ttacaactag cattgcctca aaaactggga ccaaccaaag tgtgtcaacc ctgtttcctt | 6780 |
| aaaagaggct atgaatccca aaggccacat ccaagacagg caataatgag cagagtttac | 6840 |
| agctcctttta ataaaatgtg tcagtaattt taaggtttat agttccctca acacaattgc | 6900 |
| taatgcagaa tagtgtaaaa tgcgcttcaa gaatgttgat gatgatgata tagaattgtg | 6960 |
| gctttagtag cacagaggat gccccaacaa actcatggcg ttgaaaccac acagttctca | 7020 |
| ttactgttat ttattagctg tagcattctc tgtctcctct ctctcctcct ttgaccttct | 7080 |
| cctcgaccag ccatcatgac atttaccatg aatttacttc ctcccaagag tttggactgc | 7140 |
| ccgtcagatt gttgctgcac atagttgcct ttgtatctct gtatgaaata aaaggtcatt | 7200 |
| tgttcatgtt aaaaaaaaa | 7219 |

<210> SEQ ID NO 62
<211> LENGTH: 1657
<212> TYPE: PRT
<213> ORGANISM: Homo sapiens

<400> SEQUENCE: 62

Met Ser Ala Ala Asp Glu Val Asp Gly Leu Gly Val Ala Arg Pro His
1               5                   10                  15

Tyr Gly Ser Val Leu Asp Asn Glu Arg Leu Thr Ala Glu Glu Met Asp
            20                  25                  30

Glu Arg Arg Arg Gln Asn Val Ala Tyr Glu Tyr Leu Cys His Leu Glu
        35                  40                  45

Glu Ala Lys Arg Trp Met Glu Ala Cys Leu Gly Glu Asp Leu Pro Pro
    50                  55                  60

Thr Thr Glu Leu Glu Glu Gly Leu Arg Asn Gly Val Tyr Leu Ala Lys
65                  70                  75                  80

Leu Gly Asn Phe Phe Ser Pro Lys Val Val Ser Leu Lys Lys Ile Tyr
                85                  90                  95

Asp Arg Glu Gln Thr Arg Tyr Lys Ala Thr Gly Leu His Phe Arg His
            100                 105                 110

Thr Asp Asn Val Ile Gln Trp Leu Asn Ala Met Asp Glu Ile Gly Leu
        115                 120                 125

Pro Lys Ile Phe Tyr Pro Glu Thr Thr Asp Ile Tyr Asp Arg Lys Asn

```
              130                 135                 140
Met Pro Arg Cys Ile Tyr Cys Ile His Ala Leu Ser Leu Tyr Leu Phe
145                 150                 155                 160

Lys Leu Gly Leu Ala Pro Gln Ile Gln Asp Leu Tyr Gly Lys Val Asp
                    165                 170                 175

Phe Thr Glu Glu Glu Ile Asn Asn Met Lys Thr Glu Leu Glu Lys Tyr
                180                 185                 190

Gly Ile Gln Met Pro Ala Phe Ser Lys Ile Gly Gly Ile Leu Ala Asn
            195                 200                 205

Glu Leu Ser Val Asp Glu Ala Leu His Ala Ala Val Ile Ala Ile
        210                 215                 220

Asn Glu Ala Ile Asp Arg Arg Ile Pro Ala Asp Thr Phe Ala Ala Leu
225                 230                 235                 240

Lys Asn Pro Asn Ala Met Leu Val Asn Leu Glu Glu Pro Leu Ala Ser
                    245                 250                 255

Thr Tyr Gln Asp Ile Leu Tyr Gln Ala Lys Gln Asp Lys Met Thr Asn
                260                 265                 270

Ala Lys Asn Arg Thr Glu Asn Ser Glu Arg Glu Arg Asp Val Tyr Glu
            275                 280                 285

Glu Leu Leu Thr Gln Ala Glu Ile Gln Gly Asn Ile Asn Lys Val Asn
        290                 295                 300

Thr Phe Ser Ala Leu Ala Asn Ile Asp Leu Ala Leu Glu Gln Gly Asp
305                 310                 315                 320

Ala Leu Ala Leu Phe Arg Ala Leu Gln Ser Pro Ala Leu Gly Leu Arg
                    325                 330                 335

Gly Leu Gln Gln Gln Asn Ser Asp Trp Tyr Leu Lys Gln Leu Leu Ser
                340                 345                 350

Asp Lys Gln Gln Lys Arg Gln Ser Gly Gln Thr Asp Pro Leu Gln Lys
            355                 360                 365

Glu Glu Leu Gln Ser Gly Val Asp Ala Ala Asn Ser Ala Ala Gln Gln
        370                 375                 380

Tyr Gln Arg Arg Leu Ala Ala Val Ala Leu Ile Asn Ala Ala Ile Gln
385                 390                 395                 400

Lys Gly Val Ala Glu Lys Thr Val Leu Glu Leu Met Asn Pro Glu Ala
                    405                 410                 415

Gln Leu Pro Gln Val Tyr Pro Phe Ala Ala Asp Leu Tyr Gln Lys Glu
                420                 425                 430

Leu Ala Thr Leu Gln Arg Gln Ser Pro Glu His Asn Leu Thr His Pro
            435                 440                 445

Glu Leu Ser Val Ala Val Glu Met Leu Ser Ser Val Ala Leu Ile Asn
        450                 455                 460

Arg Ala Leu Glu Ser Gly Asp Val Asn Thr Val Trp Lys Gln Leu Ser
465                 470                 475                 480

Ser Ser Val Thr Gly Leu Thr Asn Ile Glu Glu Glu Asn Cys Gln Arg
                    485                 490                 495

Tyr Leu Asp Glu Leu Met Lys Leu Lys Ala Gln Ala His Ala Glu Asn
                500                 505                 510

Asn Glu Phe Ile Thr Trp Asn Asp Ile Gln Ala Cys Val Asp His Val
            515                 520                 525

Asn Leu Val Val Gln Glu Glu His Glu Arg Ile Leu Ala Ile Gly Leu
        530                 535                 540

Ile Asn Glu Ala Leu Asp Glu Gly Asp Ala Gln Lys Thr Leu Gln Ala
545                 550                 555                 560
```

```
Leu Gln Ile Pro Ala Ala Lys Leu Glu Gly Val Leu Ala Glu Val Ala
                565                 570                 575

Gln His Tyr Gln Asp Thr Leu Ile Arg Ala Lys Arg Glu Lys Ala Gln
            580                 585                 590

Glu Ile Gln Asp Glu Ser Ala Val Leu Trp Leu Asp Gly Ile Gln Gly
        595                 600                 605

Gly Ile Trp Gln Ser Asn Lys Asp Thr Gln Glu Ala Gln Lys Phe Ala
    610                 615                 620

Leu Gly Ile Phe Ala Ile Asn Glu Ala Val Glu Ser Gly Asp Val Gly
625                 630                 635                 640

Lys Thr Leu Ser Ala Leu Arg Ser Pro Asp Val Gly Leu Tyr Gly Val
                645                 650                 655

Ile Pro Glu Cys Gly Glu Thr Tyr His Ser Asp Leu Ala Glu Ala Lys
                660                 665                 670

Lys Lys Lys Leu Ala Val Gly Asp Asn Asn Ser Lys Trp Val Lys His
            675                 680                 685

Trp Val Lys Gly Gly Tyr Tyr Tyr His Asn Leu Glu Thr Gln Glu
        690                 695                 700

Gly Gly Trp Asp Glu Pro Pro Asn Phe Val Gln Asn Ser Met Gln Leu
705                 710                 715                 720

Ser Arg Glu Glu Ile Gln Ser Ser Ile Ser Gly Val Thr Ala Ala Tyr
                725                 730                 735

Asn Arg Glu Gln Leu Trp Leu Ala Asn Glu Gly Leu Ile Thr Arg Leu
                740                 745                 750

Gln Ala Arg Cys Arg Gly Tyr Leu Val Arg Gln Glu Phe Arg Ser Arg
            755                 760                 765

Met Asn Phe Leu Lys Lys Gln Ile Pro Ala Ile Thr Cys Ile Gln Ser
770                 775                 780

Gln Trp Arg Gly Tyr Lys Gln Lys Lys Ala Tyr Gln Asp Arg Leu Ala
785                 790                 795                 800

Tyr Leu Arg Ser His Lys Asp Glu Val Val Lys Ile Gln Ser Leu Ala
                805                 810                 815

Arg Met His Gln Ala Arg Lys Arg Tyr Arg Asp Arg Leu Gln Tyr Phe
            820                 825                 830

Arg Asp His Ile Asn Asp Ile Ile Lys Ile Gln Ala Phe Ile Arg Ala
            835                 840                 845

Asn Lys Ala Arg Asp Asp Tyr Lys Thr Leu Ile Asn Ala Glu Asp Pro
850                 855                 860

Pro Met Val Val Arg Lys Phe Val His Leu Leu Asp Gln Ser Asp
865                 870                 875                 880

Gln Asp Phe Gln Glu Glu Leu Asp Leu Met Lys Met Arg Glu Glu Val
            885                 890                 895

Ile Thr Leu Ile Arg Ser Asn Gln Gln Leu Glu Asn Asp Leu Asn Leu
                900                 905                 910

Met Asp Ile Lys Ile Gly Leu Leu Val Lys Asn Lys Ile Thr Leu Gln
            915                 920                 925

Asp Val Val Ser His Ser Lys Lys Leu Thr Lys Lys Asn Lys Glu Gln
            930                 935                 940

Leu Ser Asp Met Met Met Ile Asn Lys Gln Lys Gly Gly Leu Lys Ala
945                 950                 955                 960

Leu Ser Lys Glu Lys Arg Glu Lys Leu Glu Ala Tyr Gln His Leu Phe
                965                 970                 975
```

```
Tyr Leu Leu Gln Thr Asn Pro Thr Tyr Leu Ala Lys Leu Ile Phe Gln
            980                 985                 990

Met Pro Gln Asn Lys Ser Thr Lys Phe Met Asp Ser Val Ile Phe Thr
        995                1000                1005

Leu Tyr Asn Tyr Ala Ser Asn Gln Arg Glu Tyr Leu Leu Leu
    1010                1015                1020

Arg Leu Phe Lys Thr Ala Leu Gln Glu Glu Ile Lys Ser Lys Val
    1025                1030                1035

Asp Gln Ile Gln Glu Ile Val Thr Gly Asn Pro Thr Val Ile Lys
    1040                1045                1050

Met Val Val Ser Phe Asn Arg Gly Ala Arg Gly Gln Asn Ala Leu
    1055                1060                1065

Arg Gln Ile Leu Ala Pro Val Lys Glu Ile Met Asp Asp Lys
    1070                1075                1080

Ser Leu Asn Ile Lys Thr Asp Pro Val Asp Ile Tyr Lys Ser Trp
    1085                1090                1095

Val Asn Gln Met Glu Ser Gln Thr Gly Glu Ala Ser Lys Leu Pro
    1100                1105                1110

Tyr Asp Val Thr Pro Glu Gln Ala Leu Ala His Glu Glu Val Lys
    1115                1120                1125

Thr Arg Leu Asp Ser Ser Ile Arg Asn Met Arg Ala Val Thr Asp
    1130                1135                1140

Lys Phe Leu Ser Ala Ile Val Ser Ser Val Asp Lys Ile Pro Tyr
    1145                1150                1155

Gly Met Arg Phe Ile Ala Lys Val Leu Lys Asp Ser Leu His Glu
    1160                1165                1170

Lys Phe Pro Asp Ala Gly Glu Asp Glu Leu Leu Lys Ile Ile Gly
    1175                1180                1185

Asn Leu Leu Tyr Tyr Arg Tyr Met Asn Pro Ala Ile Val Ala Pro
    1190                1195                1200

Asp Ala Phe Asp Ile Ile Asp Leu Ser Ala Gly Gly Gln Leu Thr
    1205                1210                1215

Thr Asp Gln Arg Arg Asn Leu Gly Ser Ile Ala Lys Met Leu Gln
    1220                1225                1230

His Ala Ala Ser Asn Lys Met Phe Leu Gly Asp Asn Ala His Leu
    1235                1240                1245

Ser Ile Ile Asn Glu Tyr Leu Ser Gln Ser Tyr Gln Lys Phe Arg
    1250                1255                1260

Arg Phe Phe Gln Thr Ala Cys Asp Val Pro Glu Leu Gln Asp Lys
    1265                1270                1275

Phe Asn Val Asp Glu Tyr Ser Asp Leu Val Thr Leu Thr Lys Pro
    1280                1285                1290

Val Ile Tyr Ile Ser Ile Gly Glu Ile Ile Asn Thr His Thr Leu
    1295                1300                1305

Leu Leu Asp His Gln Asp Ala Ile Ala Pro Glu His Asn Asp Pro
    1310                1315                1320

Ile His Glu Leu Leu Asp Asp Leu Gly Glu Val Pro Thr Ile Glu
    1325                1330                1335

Ser Leu Ile Gly Glu Ser Ser Gly Asn Leu Asn Asp Pro Asn Lys
    1340                1345                1350

Glu Ala Leu Ala Lys Thr Glu Val Ser Leu Thr Leu Thr Asn Lys
    1355                1360                1365

Phe Asp Val Pro Gly Asp Glu Asn Ala Glu Met Asp Ala Arg Thr
```

|  |  |  |  | 1370 |  |  |  | 1375 |  |  |  | 1380 |  |  |
|---|---|---|---|---|---|---|---|---|---|---|---|---|---|---|
| Ile | Leu | Leu | Asn | Thr | Lys | Arg | Leu | Ile | Val | Asp | Val | Ile | Arg | Phe |
| 1385 |  |  |  | 1390 |  |  |  | 1395 |  |  |  |  |  |  |
| Gln | Pro | Gly | Glu | Thr | Leu | Thr | Glu | Ile | Leu | Glu | Thr | Pro | Ala | Thr |
| 1400 |  |  |  | 1405 |  |  |  | 1410 |  |  |  |  |  |  |
| Ser | Glu | Gln | Glu | Ala | Glu | His | Gln | Arg | Ala | Met | Gln | Arg | Arg | Ala |
| 1415 |  |  |  | 1420 |  |  |  | 1425 |  |  |  |  |  |  |
| Ile | Arg | Asp | Ala | Lys | Thr | Pro | Asp | Lys | Met | Lys | Lys | Ser | Lys | Ser |
| 1430 |  |  |  | 1435 |  |  |  | 1440 |  |  |  |  |  |  |
| Val | Lys | Glu | Asp | Ser | Asn | Leu | Thr | Leu | Gln | Glu | Lys | Lys | Glu | Lys |
| 1445 |  |  |  | 1450 |  |  |  | 1455 |  |  |  |  |  |  |
| Ile | Gln | Thr | Gly | Leu | Lys | Lys | Leu | Thr | Glu | Leu | Gly | Thr | Val | Asp |
| 1460 |  |  |  | 1465 |  |  |  | 1470 |  |  |  |  |  |  |
| Pro | Lys | Asn | Lys | Tyr | Gln | Glu | Leu | Ile | Asn | Asp | Ile | Ala | Arg | Asp |
| 1475 |  |  |  | 1480 |  |  |  | 1485 |  |  |  |  |  |  |
| Ile | Arg | Asn | Gln | Arg | Arg | Tyr | Arg | Gln | Arg | Arg | Lys | Ala | Glu | Leu |
| 1490 |  |  |  | 1495 |  |  |  | 1500 |  |  |  |  |  |  |
| Val | Lys | Leu | Gln | Gln | Thr | Tyr | Ala | Ala | Leu | Asn | Ser | Lys | Ala | Thr |
| 1505 |  |  |  | 1510 |  |  |  | 1515 |  |  |  |  |  |  |
| Phe | Tyr | Gly | Glu | Gln | Val | Asp | Tyr | Tyr | Lys | Ser | Tyr | Ile | Lys | Thr |
| 1520 |  |  |  | 1525 |  |  |  | 1530 |  |  |  |  |  |  |
| Cys | Leu | Asp | Asn | Leu | Ala | Ser | Lys | Gly | Lys | Val | Ser | Lys | Lys | Pro |
| 1535 |  |  |  | 1540 |  |  |  | 1545 |  |  |  |  |  |  |
| Arg | Glu | Met | Lys | Gly | Lys | Lys | Ser | Lys | Lys | Ile | Ser | Leu | Lys | Tyr |
| 1550 |  |  |  | 1555 |  |  |  | 1560 |  |  |  |  |  |  |
| Thr | Ala | Ala | Arg | Leu | His | Glu | Lys | Gly | Val | Leu | Leu | Glu | Ile | Glu |
| 1565 |  |  |  | 1570 |  |  |  | 1575 |  |  |  |  |  |  |
| Asp | Leu | Gln | Val | Asn | Gln | Phe | Lys | Asn | Val | Ile | Phe | Glu | Ile | Ser |
| 1580 |  |  |  | 1585 |  |  |  | 1590 |  |  |  |  |  |  |
| Pro | Thr | Glu | Glu | Val | Gly | Asp | Phe | Glu | Val | Lys | Ala | Lys | Phe | Met |
| 1595 |  |  |  | 1600 |  |  |  | 1605 |  |  |  |  |  |  |
| Gly | Val | Gln | Met | Glu | Thr | Phe | Met | Leu | His | Tyr | Gln | Asp | Leu | Leu |
| 1610 |  |  |  | 1615 |  |  |  | 1620 |  |  |  |  |  |  |
| Gln | Leu | Gln | Tyr | Glu | Gly | Val | Ala | Val | Met | Lys | Leu | Phe | Asp | Arg |
| 1625 |  |  |  | 1630 |  |  |  | 1635 |  |  |  |  |  |  |
| Ala | Lys | Val | Asn | Val | Asn | Leu | Leu | Ile | Phe | Leu | Leu | Asn | Lys | Lys |
| 1640 |  |  |  | 1645 |  |  |  | 1650 |  |  |  |  |  |  |
| Phe | Tyr | Gly | Lys |  |  |  |  |  |  |  |  |  |  |  |
| 1655 |  |  |  |  |  |  |  |  |  |  |  |  |  |  |

SCAFFOLD-KINASE INTERACTION BLOCKADES AND USES THEREOF IN TREATING CANCER

CROSS REFERENCE TO RELATED APPLICATIONS

Pursuant to 35 U.S.C. §119 (e), this application claims priority to the filing date of the U.S. Provisional Patent Application Ser. No. 61/494,774 filed Jun. 8, 2011; the disclosure of which is herein incorporated by reference.

GOVERNMENT RIGHTS

This invention was made with government support under contract AR049737 awarded by the National Institutes of Health. The Government has certain rights in the invention.

FIELD OF THE INVENTION

This invention pertains to the use of agents that inhibit the interaction between scaffold proteins and kinases for the treatment of cancer.

BACKGROUND OF THE INVENTION

Cancer is a worldwide epidemic claiming over 7.6 million lives per year and is the leading cause of death in developed countries (International Agency for Research on Cancer. Cancer Mondial 2010. Lyon, France: World Health Organization; Jemal, A., et al. Global cancer statistics. CA Cancer J Clin 61, 69-90 (2011)). In the US alone, current statistics estimate that over the course of a lifetime 1 in 2 men and 1 in 3 women will develop some form of cancer (American Cancer Society. Cancer Facts & Figures 2010. Atlanta, Ga.: American Cancer Society (2010); International Agency for Research on Cancer. Cancer Mondial 2010. Lyon, France: World Health Organization (2010)). While cancer can be characterized by persistent cell proliferation, inhibition of apoptosis, and altered cell migratory behavior, cancer is, at its core, a disease of dysregulated signal transduction (Hanahan, D. and Weinberg, R. A. The hallmarks of cancer. Cell 100, 57-70 (2000); Dhillon, A. S., et al. MAP kinase signaling pathways in cancer. Oncogene 26, 3279-3290 (2007)). Targeting key signaling cascades that regulate these processes will lead to the development of efficacious therapeutics.

Mitogen activated protein kinase (MAPK) cascades are evolutionarily conserved three-tier phosphorylation relays. A MAPK kinase kinase (MAPKKK) phosphorylates and activates downstream target MAPK kinase (MAPKK), which in turn phosphorylates and activates downstream target MAPK (Dhillon, A. S., et al. MAP kinase signaling pathways in cancer. Oncogene 26, 3279-3290 (2007)). The extracellular signal-regulated kinase (ERK) MAPK pathway is probably the most well-known MAPK cascade (Kolch, W., et al. The role of RAF kinases in malignant transformation. Expert Rev Mol Med 4, 1-18 (2002)). In this pathway, the MAPKKK are C-RAF-1, A-RAF, and B-RAF with MEK1 and MEK2 acting as MAPKK and ERK1 and ERK2 denoted as MAPK. This cascade is initiated by activation of RAS, the first identified human oncogene (Tabin, C. J., et al. Mechanism of activation of a human oncogene. Nature 300, 143-149 (1982)). As this pathway is capable of regulating proliferation, differentiation, migration, and survival, it is not surprising that more than one-third of all human cancers are characterized by pathologic activation of this pathway, most often as a result of constitutive activation of core kinases (FIG. 1A) (Kolch, W., et al. The role of RAF kinases in malignant transformation. Expert Rev Mol Med 4, 1-18 (2002); Hoshino, R., et al. Constitutive activation of the 41-/43-kDa mitogen-activated protein kinase signaling pathway in human tumors. Oncogene 18, 813-22 (1999); Schubbert, S., et al. Hyperactive RAS in developmental disorders and cancer. Nature Rev. Cancer 7, 295-308 (2007); Dhillon, A. S., et al. MAP kinase signaling pathways in cancer. Oncogene 26, 3279-3290 (2007); Reddy, K. B., et al. Role of MAP kinase in tumor progression and invasion. Cancer Metastasis Rev 22, 395-403 (2003)). Targeting this pathway may prove efficacious in treating cancer (FIG. 1B).

SUMMARY OF THE INVENTION

Aspects of the invention include compositions and methods for inhibiting the interaction between scaffold proteins and kinases. These compositions and methods find a number of uses including, for example, suppressing tumor growth and metastasis and reducing tumor size and number in a mammal with cancer.

In some aspects of the invention, methods are provided for inhibiting intracellular signaling in a cell, for example, hyperactive or constitutively active intracellular signaling, e.g. signaling that results in a cancerous phenotype in the cell such as cancerous proliferation or metastasis, by contacting a cell with an effective amount of an agent that is a scaffold-kinase interaction blockade ("SKIB"). In some embodiments, the intracellular signaling is activity by the RAS pathway, i.e. RAS pathway activity. In some such embodiments, the cell is a cancer cell, and the cancer is a RAS pathway-driven cancer. In some such embodiments, the cell is selected from the group consisting of a skin cancer cell, a breast cancer cell, a colorectal cancer cell, and a prostate cancer cell. In some such embodiments, the method inhibits RAS-driven cell proliferation and/or cell metastasis. In some embodiments, the cell is in vitro. In other embodiments, the cell is in vivo. In some embodiments the SKIB is an IQGAP1 WW peptide or a nucleic acid encoding an IQGAP1 WW peptide.

In some aspects of the invention, methods are provided for treating a mammalian subject for cancer. In such methods, an effective amount of an agent that inhibits the interaction between a scaffold protein and a kinase, i.e. a SKIB, is administered to the subject. In some embodiments, the SKIB is a blocking peptide or a nucleic acid that encodes a blocking peptide. In other embodiments, the SKIB is a small molecule. In some embodiments, the cancer is a RAS-driven cancer. In some embodiments, the SKIB blocks the interaction between the scaffold protein IQGAP1 and a RAS pathway kinase. In some such embodiments, the SKIB is an IQGAP1 WW peptide or a nucleic acid encoding an IQGAP1 WW peptide. In some embodiments, the SKIB is administered intratumorally. In some embodiments, the SKIB is administered systemically. In some embodiments, the SKIB is co-administered with a cancer therapy. In some embodiments, the cancer is selected from the group consisting of a skin cancer, a breast cancer, a colorectal cancer, a prostate cancer, and a lung cancer.

In some aspects of the invention, compositions are provided for inhibiting the interaction between the scaffold protein IQGAP1 and its cognate kinases, for example, the kinase ERK and the kinase AKT. In some embodiments, the composition is an isolated IQGAP1 WW peptide. In some embodiments, the composition is a pharmaceutical composition comprising or consisting essentially of the IQGAP1 WW peptide. In some embodiments, the composition specifically suppresses cancer cell proliferation and metastasis, for example, to treat a cancer that is a RAS-driven cancer or PI3K-driven cancer. In some embodiments, the composition specifically reduces the size and number of tumors in the cancer patient. In some embodiments, the cancer is a carcinoma, e.g. a skin cancer, a breast cancer, a colorectal cancer, a prostate cancer, or a lung cancer.

In some aspects of the invention, the methods and compositions are applied to reducing or preventing cancer cell metastasis in the mammalian subject. In some such embodiments, the method further comprises the step of measuring the number of tumors in the individual after administration of the SKIB. In some aspects of the invention, methods and compositions are applied to suppressing or reversing tumor growth in a mammalian subject. In some such embodiments, the method further comprises the step of measuring tumor size in the individual after administration of the IQGAP1 inhibitor. In certain embodiments, tumor size is decreased at least 2-fold thirty days after the administration of the IQGAP1 inhibitor.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 1 depicts the organization of the ERK/MAPK pathway and previous efforts to target ERK/MAPK pathway proteins. (A) Ligand-binding to cell surface receptors mediates the GDP to GTP molecular switch and conformational change in the small G protein RAS. RAS is then able to initiate the phosphorylation cascade from RAF to MEK to ERK. ERK has >140 targets which can regulate apoptosis, migration, and proliferation pathways. More than 30% of all human cancers are characterized by upregulation of this pathway with constitutive activation, cancer-associated mutations occurring at many points. (B) Efforts to target ERK/MAPK pathway proteins are indicated in red. These efforts face the challenge that these kinases are required for tissue viability in mammals. Additionally, the effectiveness of new inhibitors of mutant BRAF has been diminished by acquired tumor resistance via selection for B-Raf-independent mechanisms of Erk1/2 induction. Moreover, recently identified Erk1/2-inducing mutations in MEK1/2 MAPK kinase genes in melanoma confer resistance to emerging therapeutic MEK inhibitors, underscoring the challenges facing the general strategy of direct kinase inhibition. The current standard of care, therefore, is a combination of chemotherapy with dose-limiting side effects and diminished quality of life as well as some kinase-targeted treatments that are plagued by acquired resistance.

FIG. 2 demonstrates that inhibition of ERK via UO126 inhibits neoplastic invasion. (A) Immunofluorescence staining (upper) of the epithelial marker keratin 5 (orange) and the basement membrane zone (BMZ) protein type-VII collagen (green) and corresponding immunohistochemistry staining (lower) of normal human organotypic tissue expressing LacZ and treated daily with DMSO, UO126 (5 µM), SB0203580 (2.6 µM), PD98059 (18.7 µM), or LY294002 (5 µM). (B) Organotypic tissue expressing H-RAS$^{G12V}$/IκBαM with stains and drug treatments as in (A). (C) Quantitative invasion index (±SD) of neoplastic tissue in (B). (D) Immunoblots of primary keratinocyte extracts comparing phosphorylated ERK levels in response to treatment with DMSO or UO126 (5 µM). Cell lysates were also probed with antibodies to total ERK and actin to verify equal loading. All stains and immunoblots are representative images for at least 3 independent experiments.

FIG. 4 lists the ERK/MAPK scaffolds.

FIG. 6 demonstrates that IQGAP family members share a high degree of identity. (A) Diagram of IQGAP1 (middle), IQGAP2 (top), and IQGAP3 (bottom) structure with degree of homology in each of the protein domains indicated. Figure was adapted from (47)(48)(49). (B) qRT-PCR validating lack of compensation in IQGAP1 and IQGAP2 levels by IQGAP2 and IQGAP1 siRNAs, respectively. All qPCR (±SD) are representative of at least 3 independent experiments.

FIG. 10 demonstrates that IQGAP1 knockout mice heal wounds similarly to wildtype animals. (A) Macroscopic images of wounds for IQGAP1 wildtype (top), heterozygous (middle), and null (bottom) animals over time. The black scale bar=1 mm. (B) Quantification of wound healing in (A). n=7 mice per group, ±SD.

FIG. 14 demonstrates that IQGAP1 is strongly overexpressed in human squamous cell carcinoma. (A) Quantification of IQGAP1 expression in SCC tissue microarrays compared to normal epithelial tissue. Tumors were blindly scored based upon strength of IQGAP1 stain. N=39 and 265 for normal and SCC tissue, respectively. (B) Quantification of IQGAP1 expression in SCC tissue microarrays by SCC grade. Scored as in (A). N=162, 85, and 18 for SCC grade I, grade II, and grade III, respectively. (C) Representative immunohistochemistry stains for data quantified in (A) and (B).

FIG. 21 demonstrates that the thirty-two amino acid WW domain of IQGAP1 inhibits growth of RAS-driven cancers in vitro. (A) Proliferation assays of primary human epithelial cells (keratinocytes and melanocytes), EGFR-overexpressing SCC-25 SCC cancer cells, BRAF-mutant Colo-829 melanoma cancer cells, EGFR-overexpressing MDA-MB-468 breast cancer cells, EGFR overexpressing PC3 prostate cancer cells, KRAS-mutant HCT-116 colorectal cancer cells, and EGFR-overexpressing H322M lung cancer cells following treatment with empty vector or WW lentiviruses as indicated. (B) Immunoblots of cell lysates from primary human melanocytes (NHM) and melanoma cancer cells without Ras-MAPK pathway mutations (WT BRAF/NRAS, CHL1) or with pathway mutations (BRAFV600E, Colo-829 and NRASQ61L, MM-485) were probed to detect levels of phosphorylated ERK and total ERK as a loading control. (C) Growth of tumors derived from melanoma cancer cells as in (B) infected with empty vector (EV) or WW-expressing lentivirus and injected into subcutaneous space of hairless SCID mice quantified by tumor volume (n=3 mice per group). (D) Representative end time point images of tumors as in (c). Scale bar: 5 mm. (E) Growth of tumor as in (C) quantified by mean average radiance [photons per second per cm2 per steradian±SD]; (n=3 mice per group). (F) Representative luciferase images of mice as in (E).

FIG. 24 demonstrates that exogenous peptide delivery of WW domain of IQGAP1 inhibits neoplastic invasion. (A) Confocal stacks showing the expression of keratin (in red), BMZ protein type-VII collagen (in green), and nuclei of keratinocytes and fibroblasts (in blue) of Ras-driven organotypic human epidermal neoplasia, treated with either 10 uM R8-myc-tagged scrambled control (SCR) or WW peptide (WW) daily. Images are X-Y plane (top) and Z-X plane (top middle). Immunohistochemistry staining for myc-tag (middle), pErk1/2 (bottom middle), and total Erk1/2 (bottom). Black dashed line denotes BMZ separation of epidermis and underlying dermis. Black arrowheads denote residual pErk staining in WW peptide tissue. (B) Lysates of cells as in (A) treated with R8-myc-tagged scrambled peptide (left) or R8-myc-tagged IQGAP1 WW domain peptide (right) were probed with myc, phosphorylated-ERK, and total ERK. Cell lysates were also probed with antibodies to actin to verify equal loading.

FIG. 27 demonstrates that systemic delivery of WW peptide in vivo can inhibit tumorigenesis. (A) Established xenograft tumors derived from BRAFV600E mutant SK-MeI-28 melanoma cancer cells were subcutaneously implanted with osmotic pumps (Alzet model 2002) (indicated by black arrows) which released 19 mg/kg/day of R8-myc-tagged Scrambled or WW peptide for 14 days (indicated by hash bars) with tumor growth quantified by mean average radiance (n=3 mice per group). (B) Weight gain of mice as in (A) reveal no negative effects on mouse growth, ±SD (C)

Representative data of tumor growth as quantified by average radiance±SEM from d21 and d43 post pump implantation with black dash bar corresponds to average initial tumor size. (D) Representative data of tumor growth as quantified by tumor volume±SEM from d28 and d43.

Figure 28:
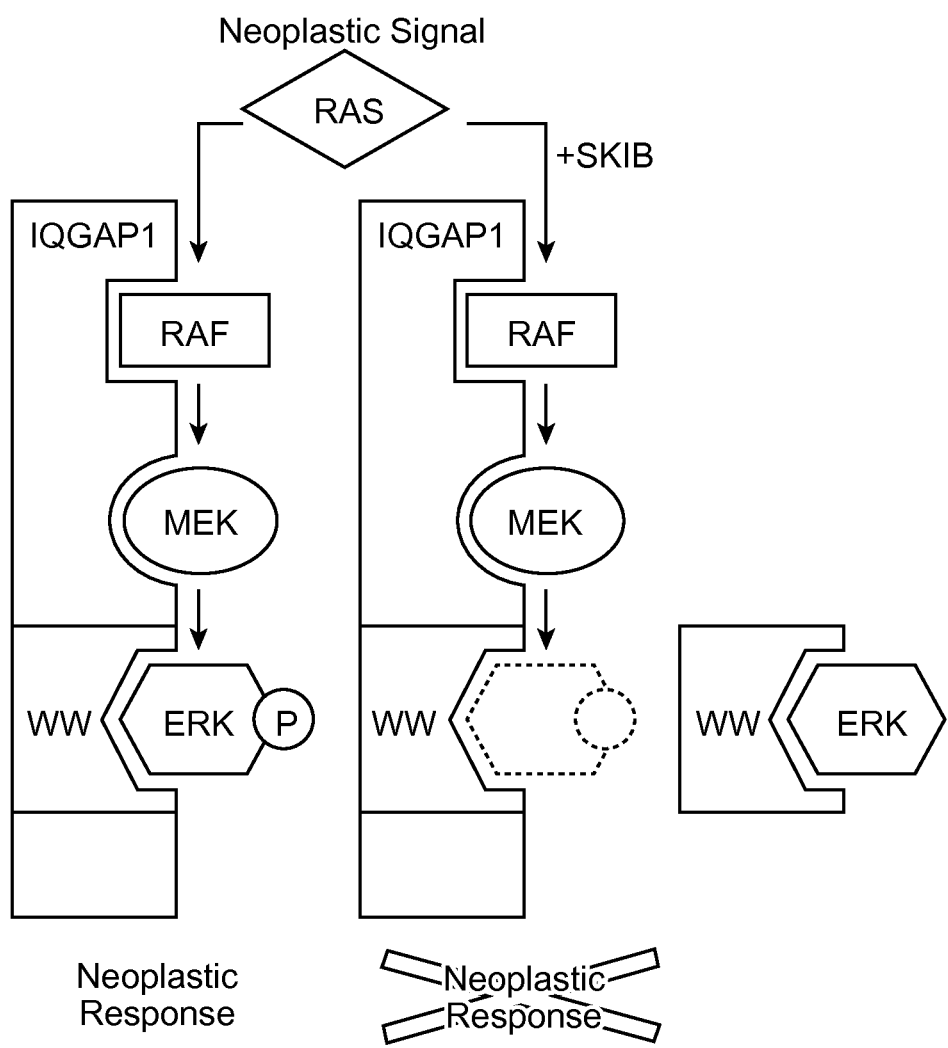

FIG. 28 provides a model for WW-mediated scaffold-kinase interaction blockade (SKIB) action in Erk1/2 MAPK hyperactive cancer. In untreated cancer cells (left), IQGAP1 scaffolds Raf, Mek1/2, and Erk1/2 kinases and facilitate neoplasia-enabling signal transduction. In the presence of WW SKIB (right), Erk1/2 is sequestered away from the IQGAP1 scaffold, pErk1/2 levels are diminished, and neoplastic response is attenuated.

DETAILED DESCRIPTION OF THE INVENTION

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

Aspects of the invention include compositions and methods for inhibiting the interaction between scaffold proteins and kinases. These compositions and methods find a number of uses including, for example, suppressing tumor growth and metastasis and reducing tumor size and number in a mammal with cancer. These and other objects, advantages, and features of the invention will become apparent to those persons skilled in the art upon reading the details of the compositions and methods as more fully described below.

The terms "subject," "individual," and "patient" are used interchangeably herein to refer to a mammal being assessed for treatment and/or being treated. In an embodiment, the mammal is a human. The terms "subject," "individual," and "patient" thus encompass individuals having cancer (e.g., colorectal cancer, adenocarcinoma of the ovary or prostate, breast carcinoma, lung carcinoma, etc.), including those who have undergone or are candidates for resection (surgery) to remove cancerous tissue (e.g., cancerous colorectal tissue). Subjects may be human, but also include other mammals, particularly those mammals useful as laboratory models for human disease, e.g. mouse, rat, etc.

As used herein, the terms "treatment," "treating," and the like, refer to administering an agent, or carrying out a procedure (e.g., radiation, a surgical procedure, etc.), for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, covers any treatment of any metastatic tumor in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease. In tumor (e.g., cancer) treatment, a therapeutic agent may reduce the rate in which a tumor size is increasing or new tumors are forming; it may prevent any increase in tumor size or numbers of tumors formed; or it may directly decrease the size of tumors and/or metastasis of tumor cells.

"In combination with", "combination therapy" and "combination products" refer, in certain embodiments, to the concurrent administration to a patient of a first therapeutic and the compounds as used herein. When administered in combination, each component can be administered at the same time or sequentially in any order at different points in time. Thus, each component can be administered separately but sufficiently closely in time so as to provide the desired therapeutic effect.

According to the present invention, the first therapeutic can be any suitable therapeutic agent, e.g., cytotoxic agents. Other combination therapies are radiation, surgery, and hormone deprivation (Kwon et al., Proc. Natl. Acad. Sci. U.S.A., 96: 15074-9, 1999). Angiogenesis inhibitors can also be combined with the methods of the invention.

"Concomitant administration" of a known cancer therapeutic drug with a pharmaceutical composition of the present invention means administration of the drug and IQGAP1 inhibitor at such time that both the known drug and the composition of the present invention will have a therapeutic effect. Such concomitant administration may involve concurrent (i.e. at the same time), prior, or subsequent administration of the drug with respect to the administration of a compound of the present invention. A person of ordinary skill in the art would have no difficulty determining the appropriate timing, sequence and dosages of administration for particular drugs and compositions of the present invention.

The term "cell culture" or "culture" means the maintenance of cells in an artificial, in vitro environment. It is to be understood, however, that the term "cell culture" is a generic term and may be used to encompass the cultivation not only of individual cells, but also of tissues or organs.

The term "tumor," as used herein, refers to all neoplastic cell growth and proliferation, whether malignant or benign, and all pre-cancerous and cancerous cells and tissues.

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. In general, cells of interest for detection, analysis, classification, or treatment in the present application include precancerous (e.g., benign), malignant, pre-metastatic, metastatic, and non-metastatic cells. Examples of cancer include but are not limited to, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer.

By a "RAS-driven cancer", it is meant a cancer in which there is hyperactivation of RAS-ERK/MAPK pathway signaling either by upstream RTKs or downstream kinases, including without limitation the disregulation of a ras proto-oncogene. RAS is a guanosine-nucleotide-binding protein ("G-protein") that activates the MAPK signaling cascade. There are four highly homologous RAS isoforms—H-RAS, NRAS, KRAS4A, and KRAS4B. Each one is identical for the first 85 amino acids followed by a highly variable C-terminus. When inappropriately activated, e.g. by constitutively active mutation, RAS proteins play a key role in uncontrolled proliferation and malignant transformation.

By a "PI3K-driven cancer," it is meant a cancer in which there is hyperactivation of the P13 kinase pathway signaling either by upstream RTKs or downstream kinases, including without limitation the disregulation of the kinase Akt. Akt, also known as Akt1 or Protein Kinase B (PKB), is a serine/threonine-specific protein kinase that plays a key role in multiple cellular processes such as glucose metabolism, apoptosis, cell proliferation, transcription and cell migration. Since it can block apoptosis, and thereby promote cell survival, Akt has been implicated as a major factor in many types of cancer. Akt was originally identified as the oncogene in the transforming retrovirus, AKT8.

As used herein, the term "cancer cell proliferation" refers to the proliferation of neoplastic cells that results in the growth of a tumor.

As used herein, the term "cancer metastasis" or simply "metastasis" refers to the spread of cancer cells from one organ or part of an organ to another, non-adjacent organ or organ part. In other words, it is the growth of a cancerous tumor in an organ or body part, which is not directly connected to the organ of the original cancerous tumor. Metastasis will be understood to include micrometastasis, which is the presence of an undetectable amount of cancerous cells in an organ or body part which is not directly connected to the organ of the original cancerous tumor. Metastasis can also be defined as several steps of a process, such as the departure of cancer cells from an original tumor site, migration to another site, and invasion of cancer cells into other tissues of the body. Therefore, the present invention contemplates a method of treating, i.e. suppressing, preventing, or halting, growth of one or more cancerous tumors in an organ or body part which is not directly connected to the organ of the original cancerous tumor, and/or any steps in a process leading up to that growth.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs; therefore tumor spread encompasses tumor metastasis.

The term "diagnosis" is used herein to refer to the identification of a molecular or pathological state, disease or condition, such as the identification of a molecular subtype of breast cancer, prostate cancer, or other type of cancer.

The term "prognosis" is used herein to refer to the prediction of the likelihood of cancer-attributable death or progression, including recurrence, metastatic spread, and drug resistance, of a neoplastic disease, such as lung, colon, skin or esophageal cancer. The term "prediction" is used herein to refer to the act of foretelling or estimating, based on observation, experience, or scientific reasoning. In one example, a physician may predict the likelihood that a patient will survive, following surgical removal of a primary tumor and/or chemotherapy for a certain period of time without cancer recurrence.

As used herein, the phrase "disease-free survival," refers to the lack of such tumor recurrence and/or spread and the fate of a patient after diagnosis, with respect to the effects of the cancer on the life-span of the patient. The phrase "overall survival" refers to the fate of the patient after diagnosis, despite the possibility that the cause of death in a patient is not directly due to the effects of the cancer. The phrases, "likelihood of disease-free survival", "risk of recurrence" and variants thereof, refer to the probability of tumor recurrence or spread in a patient subsequent to diagnosis of cancer, wherein the probability is determined according to the process of the invention.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

A "biological sample" encompasses a variety of sample types obtained from an individual. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's cancer cell, e.g., a sample comprising polynucleotides and/or polypeptides that is obtained from a patient's cancer cell (e.g., a cell lysate or other cell extract comprising polynucleotides and/or polypeptides); and a sample comprising cancer cells from a patient. A biological sample comprising a cancer cell from a patient can also include non-cancerous cells.

In some instances, e.g. to determine the efficacy of a method described herein, a cancerous tissue sample may be obtained. As used herein, the phrase "cancerous tissue sample" refers to any cells obtained from a cancerous tumor. In the case of solid tumors which have not metastasized, a tissue sample from the surgically removed tumor will typically be obtained and prepared for testing by conventional techniques. Alternatively, a body fluid sample, such as lymph, blood or serum sample, or an exudate fluid sample such as the cancerous organ exudate (e.g., exudate from the breast) may be collected and used as the sample to be analyzed. In the case of leukemias, lymphocytes or leukemic cells will be obtained and appropriately prepared. Similarly, in the case of any metastasized cancer, cells may be drawn from a body fluid such as lymphatic fluid, blood, serum, or a distally infected organ or exudate thereof.

The term "isolated" is intended to mean that a compound is separated from all or some of the components that accompany it in nature. "Isolated" also refers to the state of a compound (e.g. protein) separated from all or some of the components that accompany it during manufacture (e.g., chemical synthesis, recombinant expression, culture medium, and the like).

A "native sequence" is a biologically active polypeptide comprising wild-type amino acid sequence, and biologically active fragments thereof. Such native sequence polypeptides can be isolated from cells producing endogenous protein of interest or can be produced by any convenient recombinant or synthetic means.

A "variant sequence" is a biologically active polypeptide having less than 100% sequence identity with the amino acid sequence of a wild type protein over the length of the sequence, and biologically active fragments thereof. Such variants include peptides wherein one or more amino acid residues are added at the N- or C-terminus of, or within, the native sequence; from about one to 20 amino acid residues are deleted, and optionally substituted by one or more amino acid residues; and derivatives of the above polypeptides, wherein an amino acid residue has been covalently modified so that the resulting product has a non-naturally occurring amino acid. Ordinarily, biologically active variants will have an amino acid sequence having at least about 75% sequence identity, about 80% sequence identity, about 85% amino acid sequence identity, about 90% amino acid sequence identity with a native sequence polypeptide, preferably at least about 95%, more preferably at least about 99% sequence identity. Various methods known in the art may be utilized in developing such variant polypeptides.

The term "specific binding" refers to that binding which occurs between such paired species as enzyme/substrate, receptor/ligand, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or ligand/receptor interaction.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

As summarized above, aspects of the invention include compositions and methods for inhibiting the interaction between scaffold proteins and kinases. These compositions and methods find a number of uses including, for example, suppressing tumor growth and metastasis and reducing tumor size and tumor number in a mammal with cancer. In other words, the subject compositions and methods may be used to suppress cancer cell proliferation and metastasis. By "cancer cell proliferation", it is meant the uncontrolled proliferation of neoplastic, or cancer, cells that results in the growth of a tumor. By "metastasis" it is meant the spread of cancer from one organ or tissue to a non-adjacent organ or tissue. Accordingly, methods of the invention find use in preventing the growth and spread of tumors.

By "suppressing" or "preventing" cancer cell proliferation and metastasis, i.e. the growth and spread of tumors, it is meant slowing the rate of proliferation and/or metastasis relative to the rate that would be observed prior to performing the methods of the invention, e.g. by 2-fold or more, 3-fold or more, 4-fold or more, including 5-fold or more, 7-fold or more, or 10-fold or more, such as 20-fold or more, or 50-fold or more, etc., relative to the rate of proliferation and/or metastasis prior to performing the methods. Proliferation and metastasis may be assessed by any convenient in vitro or in vivo method. For example, the rate of proliferation may be assessed in vitro by, e.g., counting the number of cells in culture that divide over a period of time with $^3$H-thymidine, while the rate of metastasis may be assessed by, e.g., the extent to which neoplastic, i.e. cancer, cells invade tissue preparations in organ cultures. As another example, proliferation may be assessed in vivo by, e.g., measuring tumor size over time, i.e. before treatment and at one or more time points after the start of treatment, e.g. 1 week, 2 weeks, 30 days, 60 days, and/or 90 days or more after the start of treatment, while the rate of metastasis may be assessed by, e.g., measuring the number of metastases observed in whole body imaging over time, before and after the start of treatment. In some instances, proliferation and/or metastasis may be slowed so substantially so as to be negligible, i.e. unmeasurable, i.e. halted. In other words, no tumor growth or new tumors may be observed. As demonstrated in the examples below, in some instances, tumor growth may be reversed, i.e. tumors may begin to shrink, e.g. by 2-fold, 3-fold, or 4-fold, or more, including 5-fold or more, 7-fold or more, 10-fold or more, in some cases 20-fold or more, 50-fold or more, etc., or the number of tumors may begin to decrease.

In some aspects, a cell, e.g. a cancer cell, is contacted with an effective amount of an agent that inhibits the interaction between a scaffold protein and its cognate kinase(s). For example, a cell in culture is contacted with an effective amount of an agent that inhibits the interaction between a scaffold protein and its cognate kinase(s), e.g. for research purposes, or to screen for candidate agents that may be useful in treating cancer. As another example, a therapeutically effective amount of the agent that inhibits the interaction between a scaffold protein and its cognate kinase(s) is administered to the cancer patient, e.g. to treat the cancer. By a "scaffold protein" it is meant a protein that tethers proteins of signaling pathways into complexes, and helps localize the complexes to specific areas of the cell such as the plasma membrane, the cytoplasm, the nucleus, the Golgi, endosomes, and the mitochondria. In this way, scaffold proteins are crucial regulators of many signaling pathways. By a "kinase" it is meant a protein that activates a second protein by phosphorylating that second protein, i.e., post-translationally modifying the protein by attaching a removable phosphate group to the protein. Examples of scaffold proteins and their cognate kinases, i.e. the kinases the scaffold protein binds to and regulate, may be found in FIG. 4, and include IQGAP1 (cognate kinases EGFR, RAF, MEK and ERK of the RAS pathway, and Akt of the PI3K pathway); MEKK1 (cognate kinases RAS and ERK), KSR1 (cognate kinases RAF, MEK and ERK), MORG1 (cognate kinases RAF, MEK and ERK), Beta-arrestin 1 ("ARB1", cognate kinases RAF, MEK and ERK), Beta-arrestin 2 ("ARB2", cognate kinases RAF, MEK and ERK of the RAS-ERK pathway; and JNK3 of the JNK pathway), and MP1 (cognate kinases ERK and MEK). Other examples of scaffold proteins include JIP (cognate kinase JNK1 of the JNK pathway), MALT1 (cognate kinase CARMA1 of the NF-κB pathway), BCL10 (cognate kinase CARMA1 of the NF-κB pathway), AHNAK-1 (Desmoyokin, cognate kinase PKC, the interaction of which regulates calcium channel activity and calcium signaling), HOMER, Pellino, NLRP, DLG, and Spinophilin.

Thus, for example, in some aspects of the invention, compositions and methods are provided for inhibiting the interaction between the scaffold protein IQGAP1 and its cognate kinases, for example, the kinase ERK and the kinase AKT. Such compositions and methods find use in inhibiting RAS pathway signaling or PI3K pathway signaling in vivo and in vitro, for example in the treatment of disease such as cancers associated with hyperactive RAS pathway signaling or PI3K pathway signaling, respectively, or for research purposes, e.g. to develop a better understanding of the mechanistic basis of RAS- or PI3-driven cancer or to develop better cancer therapeutics. As another example, in some aspects of the invention, compositions and methods are provided for inhibiting the interaction between the scaffold protein JIP and the kinase JNK1. Such methods find use in inhibiting JNK pathway signaling in vivo and in vitro, for example in the treatment of disease such as cancers associated with elevated levels of JNK pathway signaling, or for research purposes, e.g. to develop a better understanding of the mechanistic basis of JNK-driven cancer or to develop better cancer therapeutics. As another example, in some aspects of the invention, compositions and methods are provided for inhibiting the interaction between the scaffold protein Beta-arrestin 2 and the kinase JNK3. Such methods find use in inhibiting p38 MAPK pathway signaling in vivo and in vitro, for example in the treatment of disease such as cancers associated with elevated levels of p38 MAPK pathway signaling, or for research purposes, e.g. to develop a better understanding of the mechanistic basis of p38-driven cancer or to develop better cancer therapeutics. As such, methods of the invention find use in a variety of cancer therapies (including cancer prevention and post-diagnosis cancer therapy) in a mammalian subject, particularly in a human. Subjects having, suspected of having, or at risk of developing a tumor are contemplated for therapy described herein.

An agent that inhibits scaffold-kinase interactions in referred to herein as a "scaffold-kinase interaction blockade", or "SKIB". By "inhibiting scaffold-kinase interactions", it is meant reducing, disrupting, or blocking the interaction between the scaffold protein and kinase. Typically, the interaction is reduced 10% or more, e.g. 20%, 30%, 40% or 50%, sometimes 60%, 70% or 80%, e.g. 90%, 95% or more, for example. until the interaction is negligible or no interaction is observed. Any convenient agent that inhibits scaffold-kinase interaction may be used in the subject methods. For example, the agent may be a blocking peptide, that is, a peptide that mimics the scaffold protein in its ability to bind to the cognate kinase, but does not have any of the functional activities of the scaffold protein. In other words, the peptide binds to the cognate kinase but cannot tether the bound kinase into complexes or localize the kinase to specific areas of the cell. The agent may be a nucleic acid that encodes for a blocking peptide. The agent may be a small molecule inhibitor, e.g. a small molecule that binds the scaffold protein or the kinase at the scaffold-kinase interaction site and blocks scaffold-kinase interaction (a competitive inhibitor), or a small molecule that binds to the scaffold protein or the kinase at a site outside of the interaction domain and prevents scaffold-kinase interaction (a non-competitive inhibitor). Cells may be contacted with agents in vitro, i.e. in culture, or in vivo by any convenient method known in the art.

In further describing aspects of the invention, the following description focuses on inhibiting the interaction between the scaffold protein IQGAP1 and its cognate kinases, e.g. ERK and Akt, for example to inhibit cancer cell proliferation, inhibit cancer metastasis, and treat cancer. However, the subject methods may also be applied to treating cancers associated with the hyperactivity of other signaling pathways, e.g. by disrupting the interactions between the scaffold proteins and their cognate kinases as described above.

IQGAP1 Inhibitors

In aspects of the invention, an agent that inhibits scaffold-kinase interactions is provided to cells, e.g. by administration to a human subject, to block the interaction between the scaffold protein IQGAP and its cognate kinase(s). IQGAP1 ("IQ motif containing GTPase activating protein 1", GenBank Accession No. NM_003870.3, SEQ ID NO:61) is a ubiquitously expressed multidomain scaffold protein that binds to a wide variety of targets and modulates several cellular activities, including cell-cell adhesion, transcription, cytoskeletal architecture, and signaling pathways. The IQGAP1 cDNA encodes a 1,657-amino acid polypeptide with a number of well-known domains. These include a calponin homology domain (CHD), which mediates actin-binding and binds calponin; a 32 amino acid protein-protein interaction domain called a "WW", or "poly-proline protein-protein" domain, (so named because of two functionally conserved tryptophans (W)), which mediates IQGAP1 interaction with proline-rich domains of other proteins; an IQ domain, comprising IQ motifs which binds calmodulin, a protein known as a calcium sensor that can bind and regulate many target proteins; a GRD domain (rasGAP-related domain), which is highly similar to the functional subunit of Ras GTPase-activating proteins (GAPs) and was thus thought to have GAP function; and a RGCT (RasGAP carboxy terminal) sequence important for binding beta-catenin and E-cadherin.

In some embodiments, the agent that acts as a scaffold-kinase interaction blockade, or "SKIB", for IQGAP1, or "IQGAP SKIB", is a peptide of IQGAP1 protein that blocks IQGAP1 binding to its cognate kinase(s). In other words, the peptide is a dominant negative of IQGAP1 activity. Included is a peptide of IQGAP1 that comprises an IQGAP1 WW domain, i.e. a fragment of the IQGAP1 protein or a variant thereof that comprises the WW domain of IQGAP1. Without wishing to be bound by theory, it is believed that the WW domain of IQGAP1 mediates the association of IQGAP1 with the proline-rich domains of MAPK-related proteins, e.g. extracellular signal-regulated kinase (ERK). In other words, the WW domain mediates the specific binding between IQGAP1 and MAPK proteins such as ERK and ERK2. The delineation of the WW domain of IQGAP1 is exemplified in FIG. 19 with IQGAP1 proteins of different species. In some instances, the IQGAP1 SKIB is an IQGAP1 peptide that consists of the complete WW domain as depicted. In some instances, the IQGAP1 WW peptide consists essentially of the complete WW domain as depicted, i.e. with only a few amino acids, e.g. 1, 2, 3, 4, 5, 6, 7, 8, 9, or 10 amino acids, of the native IQGAP1 sequence N-terminal and C terminal to the WW domain included. In some instances, the IQGAP1 WW peptide consists of the complete WW domain as depicted. In some instances, the IQGAP1 WW peptide comprises a subdomain of the WW domain as depicted, e.g. a subdomain of the WW domain that comprises the conserved tryptophans. In some instances, the IQGAP1 WW peptide comprises a variant IQGAP1 WW peptide, i.e. a biologically active polypeptide corresponding to the WW domain but having less than 100% sequence identity, e.g. having 70% or more, 75% or more, 80% or more, in some instances, 85% or more, 90% or more, 95% or more, 97% or more, or 99% sequence identity, with a native IQGAP1 sequence over the length of the fragment. In some instances, the IQGAP1 WW peptide aligns by conserved residues with positions 680-711 of human IQGAP1. Any WW-domain containing fragment of the IQGAP1 protein or variant thereof that inhibits IQGAP1-ERK or IQGAP-Akt interaction and hence IQGAP1 control of cell proliferation and/or invasion and metastasis finds use in the methods of the invention.

To improve uptake of the peptide by the cancer cell, the peptide may comprise the peptide sequences of interest fused to a peptide permeant domain. A number of permeant domains are known in the art and may be used in the non-integrating polypeptides of the present invention, including peptides, peptidomimetics, and non-peptide carriers. For example, a permeant peptide may be derived from the third alpha helix of Drosophila melanogaster transcription factor Antennapaedia, referred to as penetratin. As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, e.g. octa d-Arg, and the like. (See, for example, Futaki et al. (2003) Curr Protein Pept Sci. 2003 April; 4(2): 87-96; and Wender et al. (2000) Proc. Natl. Acad. Sci. U.S.A. 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002).

The peptide agent for use in the subject methods may be produced from eukaryotic cells, or it may be produced by prokaryotic cells, it may be further processed by unfolding, e.g. heat denaturation, DTT reduction, etc. and may be further refolded, using methods known in the art.

Modifications of interest that do not alter primary sequence include chemical derivatization of peptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are peptides that have been modified using ordinary molecular biological techniques and synthetic chemistry so as to improve their resistance to proteolytic degradation or to optimize solubility properties or to render them more suitable as a therapeutic agent. Analogs of such peptides include those containing residues other than naturally occurring L-amino acids, e.g. D-amino acids or non-naturally occurring synthetic amino acids. D-amino acids may be substituted for some or all of the amino acid residues.

The subject peptides may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The peptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

In some instances, the peptide is provided to the cancer cell by providing a nucleic acid encoding the peptide, i.e. to ectopically express the peptide of interest in the cancer cell. Any convenient vector useful for transferring nucleic acids into target cells may be used. The vectors may be maintained episomally, e.g. as plasmids, minicircle DNAs, virus-derived vectors such cytomegalovirus, adenovirus, etc., or they may be integrated into the target cell genome, through homologous recombination or random integration, e.g. retrovirus derived vectors such as MMLV, HIV-1, ALV, etc.

Vectors may be provided directly to the cells of the individual. In other words, the cancer cells are contacted with vectors comprising the nucleic acid of interest such that the vectors are taken up by the cells. Methods for contacting cells with nucleic acid vectors, such as electroporation, calcium chloride transfection, and lipofection, are well known in the art.

Alternatively, the nucleic acid of interest may be provided to the cells via a virus. In other words, the cancer cells are contacted with viral particles comprising the nucleic acid of interest. Retroviruses, for example, lentiviruses, are particularly suitable to the method of the invention. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein to be incorporated into the capsid, this envelope protein determining the specificity of the viral particle for the cells. Envelope proteins are of at least three types, ecotropic, amphotropic and xenotropic. Retroviruses packaged with ecotropic envelope protein, e.g. MMLV, are capable of infecting most murine and rat cell types, and are generated by using ecotropic packaging cell lines such as BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse, and are generated by using amphotropic packaging cell lines such as PA12 (Miller et al. (1985) *Mol. Cell. Biol.* 5:431-437); PA317 (Miller et al. (1986) *Mol. Cell. Biol.* 6:2895-2902); GRIP (Danos et al. (1988) *PNAS* 85:6460-6464). Retroviruses packaged with xenotropic envelope protein, e.g. AKR env, are capable of infecting most mammalian cell types, except murine cells. The appropriate packaging cell line may be used to ensure that the subject CD33+ differentiated somatic cells are targeted by the packaged viral particles. Any convenient method for introducing the retroviral vectors comprising the nucleic acid encoding the reprogramming factors into packaging cell lines and of collecting the viral particles that are generated by the packaging lines may be used.

Vectors used for providing nucleic acid of interest to the cancer cells will typically comprise suitable promoters for driving the expression, that is, transcriptional activation, of the nucleic acid of interest. In other words, the nucleic acid of interest will be operably linked to a promoter that will promote the expression of the nucleic acid. This may include ubiquitously acting promoters, for example, the CMV-b-actin promoter, or inducible promoters, such as promoters that are active in particular cell populations or that respond to the presence of drugs such as tetracycline. By transcriptional activation, it is intended that transcription will be increased above basal levels in the target cell by at least about 10 fold, by at least about 100 fold, more usually by at least about 1000 fold.

Other nucleic acids, e.g., nucleic acids that encode IQGAP1-specific siRNA, shRNA or antisense molecules also find use in the present invention. As demonstrated in the examples below, inhibitory nucleic acid molecules targeting any region of the IQGAP1 gene are effective in antagonizing/suppressing IQGAP1 signaling. Such molecules may be designed, prepared, and delivered using any convenient technique. See, for example, Davis, M. E., et al. Nature 464, 1067-1070 (2010), which teaches a nanoparticle delivery system for targeting siRNAs to solid tumors with introduction into adjacent tissue, and which is specifically incorporated herein by reference.

In some aspects of the invention, an effective amount of an IQGAP1 SKIB is provided. Biochemically speaking, an effective amount or effective dose of an IQGAP1 SKIB is an amount of inhibitor to decrease or attenuate IQGAP1 signaling in a cell by at least 30%, at least 40%, at least 50%, at least 60%, at least 70%, at least 80%, at least 90%, at least 95%, or by 100%. In other words, the responsiveness to IQGAP1 signaling of a cell that has been contacted with an effective amount or effective dose of an IQGAP1 SKIB will be about 70% or less, about 60% or less, about 50% or less, about 40% or less, about 30% or less, about 20% or less, about 10% or less, about 5% or less, or will be about 0%, i.e. negligible, the strength of the responsiveness observed of a cell that has not been contacted with an effective amount/dose of an IQGAP1 SKIB. The amount of modulation of a cell's activity by IQGAP1, that is, the responsiveness of a cell to IQGAP1 signaling, can be determined by any convenient method. For example, as discussed above, it is known that IQGAP1 signaling results in the phosphorylation of ERK ("pERK") and ERK's downstream target, ELK1 ("pELK1"). Accordingly, an effective amount of IQGAP1 SKIB may be determined by measuring the amount of pERK or pELK1 in a cancer cell or tumor contacted with an IQGAP1 SKIB as compared to a control cancer cell or tumor, e.g. an untreated cancer cell or tumor. In this way, the antagonistic effect of the agent may be confirmed.

In a clinical sense, an effective dose of an IQGAP1 inhibitor is the dose that, when administered for a suitable period of time, e.g. at least about one week, and maybe two weeks, or more, up to a period of 30 days, 60 days, 90 days or longer, will evidence an alteration in the pathology of the cancer. For example, an effective dose is the dose that when administered for a suitable period of time, usually at least about one week, and may be about two weeks, or more, up to a period of about 4 weeks, 8 weeks, or longer will slow tumor growth in a cancer patient and in some instances may reduce the size or number of tumors. It will be understood by those of skill in the art that an initial dose may be administered for such periods of time, followed by maintenance doses, which, in some cases, will be at a reduced dosage.

Types of Cancer

The methods relating to cancer contemplated herein include, for example, use of IQGAP1 inhibitor therapy as an anti-cancer metastasis therapy. The methods are useful in the context of treating or preventing a wide variety of cancers, including cancers that can metastasize (e.g. carcinomas and sarcomas).

Carcinomas that can be amenable to therapy by a method disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelieal carcinoma, and nasopharyngeal carcinoma.

Sarcomas that can be amenable to therapy by a method disclosed herein include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be amenable to therapy by a method disclosed herein include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Other cancers that can be amenable to treatment according to the methods disclosed herein include atypical meningioma (brain), islet cell carcinoma (pancreas), medullary carcinoma (thyroid), mesenchymoma (intestine), hepatocellular carcinoma (liver), hepatoblastoma (liver), clear cell carcinoma (kidney), and neurofibroma mediastinum.

Further exemplary cancers that can be amenable to treatment using a methods disclosed herein include, but are not limited to, cancers of neuroectodermal and epithelial origin. Examples of cancers of neuroectodermal origin include, but are not limited to, Ewings sarcoma, spinal tumors, brain tumors, supratenbrial primative neuroectodermal tumors of infancy, tubulocystic carcinoma, mucinous tubular and spindle cell carcinoma, renal tumors, mediastinum tumors, neurogliomas, neuroblastomas, and sarcomas in adolescents and young adults. Examples of epithelial origin include, but are not limited to, small cell lung cancer, cancers of the breast, eye lens, colon, pancreas, kidney, liver, ovary, and bronchial epithelium.

In some instances, the cancer is a RAS-driven cancer. By a "RAS-driven cancer", it is meant a cancer that is caused by the disregulation of a ras proto-oncogene. Ras is a guanosine-nucleotide-binding protein, or G-protein, that activates the MAPK signaling cascade. There are four highly homologous RAS isoforms—H-RAS, NRAS, KRAS4A, and KRAS4B. Each one is identical for the first 85 amino acids followed by a highly variable C-terminus. When inappropriately activated, e.g. by constitutively active mutation, ras proteins play a key role in proliferation and malignant transformation. For example, oncogenic mutations in codons 12, 13, and 61 of RAS proteins render RAS unaffected by inactivating GTPase activating proteins (GAPs) and thus unable to hydrolyze GTP resulting in constitutive activity (9). Oncogenic mutations in Ras proteins such as these and others known in the art are found in 20%-30% of all human tumors. RAS-driven cancers may be identified by any convenient method for detecting oncogenic RAS, e.g. sequencing RAS genes to detect oncogenic mutations, assaying phosphorylation of downstream MAPK targets, etc.

Combinations with Other Cancer Therapies

Therapeutic administration of the agent that blocks IQGAP1-kinase interaction, i.e. the IQGAP1 SKIB, can include administration as a part of a therapeutic regimen that may or may not be in conjunction with additional standard anti-cancer therapeutics, including but not limited to immunotherapy, chemotherapeutic agents and surgery (e.g., as those described further below).

In addition, therapeutic administration of the IQGAP1 SKIB can also be post-therapeutic treatment of the subject with an anti-cancer therapy, where the anti-cancer therapy can be, for example, surgery, radiation therapy, administration of chemotherapeutic agents, and the like. Cancer therapy using IQGAP1 SKIB of the present disclosure can also be used in combination with immunotherapy. In other examples, the IQGAP1 SKIB can be administered in combination with one or more chemotherapeutic agents (e.g., cyclophosphamide, doxorubicin, vincristine and prednisone (CHOP)), and/or in combination with radiation treatment and/or in combination with surgical intervention (e.g., pre- or post-surgery to remove a tumor). Where the IQGAP1 SKIBs are used in connection with surgical intervention, the IQGAP1 SKIB can be administered prior to, at the time of, or after surgery to remove cancerous cells, and may be administered systemically or locally at the surgical site. The IQGAP1 SKIB alone or in combinations described above can be administered systemically (e.g., by parenteral administration, e.g., by an intravenous route) or locally (e.g., at a local tumor site, e.g., by intratumoral administration (e.g., into a solid tumor, into an involved lymph node in a lymphoma or leukemia), administration into a blood vessel supplying a solid tumor, etc.).

Any of a wide variety of cancer therapies can be used in combination with the IQGAP1 SKIB therapies described herein. Such cancer therapies include surgery (e.g., surgical removal of cancerous tissue), radiation therapy, bone marrow transplantation, chemotherapeutic treatment, biological response modifier treatment, and certain combinations of the foregoing.

Radiation therapy includes, but is not limited to, X-rays or gamma rays that are delivered from either an externally applied source such as a beam, or by implantation of small radioactive sources.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (CYTOXAN™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (TAXOL®), docetaxel (TAXOTERE®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.;

phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (TAXOL®), TAXOL® derivatives, docetaxel (TAXOTERE®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and ZOLADEX®. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); IRESSA® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL, TAXOTERE (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art.

Paclitaxel should be understood to refer to not only the common chemically available form of paclitaxel, but analogs and derivatives (e.g., TAXOTERE™ docetaxel, as noted above) and paclitaxel conjugates (e.g., paclitaxel-PEG, paclitaxel-dextran, or paclitaxel-xylose).

In the treatment of some individuals in accordance with the method of the present disclosure, it may be desirable to use a high dose regimen in conjunction with a rescue agent for non-malignant cells. In such treatment, any agent capable of rescue of non-malignant cells can be employed, such as citrovorum factor, folate derivatives, or leucovorin. Such rescue agents are well known to those of ordinary skill in the art. Rescue agents include those which do not interfere with the ability of the present inventive compounds to modulate cellular function.

Administration of the IQGAP1 SKIB

Administration of the agent that inhibits IQGAP1-kinase interaction, i.e. the IQGAP1 SKIB, may be achieved through various methods to different parts of the body, including intratumoral, intravenous, intradermal, subcutaneous, oral (e.g., inhalation), transdermal (i.e., topical), transmucosal, intraperitoneal, intraarterial, and rectal administration. Other suitable routes include administration of the composition orally, bucally, nasally, nasopharyngeally, parenterally, enterically, gastrically, topically, transdermally, subcutaneously, intramuscularly, in tablet, solid, powdered, liquid, aerosol form, intralesional injection into the tumor, intralesional injection adjacent to the tumor, intravenous infusion, and intraarterial infusion. Administration may be done locally, i.e. at a tumor site, e.g. by administration into the cancerous tissue or into the tumor, e.g. by injection into the tumor, administration into a blood vessel supplying a solid tumor, etc; or systemically, i.e., to the whole body, e.g. by parenteral administration, e.g. by an intravenous route; with or without added excipients. Administering can also be done via slow release mode at or around tumor sites of a subject.

One skilled in the art will appreciate that a variety of suitable methods of administering a formulation of the present disclosure to a subject or host, e.g., patient, in need thereof, are available, and, although more than one route can be used to administer a particular formulation, a particular route can provide a more immediate and more effective reaction than another route.

The phrase "therapeutically effective amount" refers to an amount that produces some desired effect at a reasonable benefit/risk ratio applicable to any medical treatment. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation.

According to exemplary implementations, the protein may be administered as part of a composition, which is described in more detail below. The composition may be in various forms including powders, creams, gels, salves, ointments, solutions, tablets, capsules, sprays, and patches. Vehicles and carriers may be used for delivery of the composition to the patient. Such carriers include solubilizing agents, diluents, and dispersion media. These carriers are biocompatible, pharmaceutically acceptable, and do not alter the treatment characteristics of the IQGAP1 inhibitor. Excipients, adjuvants and other ingredients may also be included in the composition.

Dosage

In the methods, an effective amount of an IQGAP1 SKIB is administered to a subject in need thereof. In particular, IQGAP1 SKIBs of specific interest are those that inhibit proliferation and/or metastasis of a cancer in a host when the IQGAP1 SKIBs are administered in an effective amount. The amount administered varies depending upon the goal of the administration, the health and physical condition of the individual to be treated, age, the taxonomic group of individual to be treated (e.g., human, non-human primate, primate, etc.), the degree of resolution desired, the formulation of the IQGAP1 SKIB composition, the treating clinician's assessment of the medical situation, and other relevant factors. It is expected that the amount will fall in a relatively broad range that can be determined through routine trials. For example, the amount of IQGAP1 SKIB employed to inhibit cancer metastasis is not more than about the amount that could otherwise be irreversibly toxic to the subject (i.e., maximum tolerated dose). In other cases the amount is around or even well below the toxic threshold, but still in an immunoeffective concentration range, or even as low as threshold dose.

Individual doses are typically not less than an amount required to produce a measurable effect on the subject, and may be determined based on the pharmacokinetics and pharmacology for absorption, distribution, metabolism, and excretion ("ADME") of the IQGAP1 SKIB of its by-products, and thus based on the disposition of the composition within the subject. This includes consideration of the route of administration as well as dosage amount, which can be adjusted for topical (applied directly where action is desired for mainly a local effect), enteral (applied via digestive tract for systemic or local effects when retained in part of the digestive tract), or parenteral (applied by routes other than the digestive tract for systemic or local effects) applications. For instance, administration of the IQGAP1 SKIB is typically via injection and often intravenous, intramuscular, intratumoral, or a combination thereof.

The IQGAP1 SKIB may be administered by infusion or by local injection, e.g. by infusion at a rate of about 50 mg/h to about 400 mg/h, including about 75 mg/h to about 375 mg/h, about 100 mg/h to about 350 mg/h, about 150 mg/h to about 350 mg/h, about 200 mg/h to about 300 mg/h, about 225 mg/h to about 275 mg/h. Exemplary rates of infusion can achieve a desired therapeutic dose of, for example, about 0.5 mg/m$^2$/day to about 10 mg/m$^2$/day, including about 1 mg/m$^2$/day to about 9 mg/m$^2$/day, about 2 mg/m$^2$/day to about 8 mg/m$^2$/day, about 3 mg/m$^2$/day to about 7 mg/m$^2$/day, about 4 mg/m$^2$/day to about 6 mg/m$^2$/day, about 4.5 mg/m$^2$/day to about 5.5 mg/m$^2$/day. Administration (e.g., by infusion) can be repeated over a desired period, e.g., repeated over a period of about 1 day to about 5 days or once every several days, for example, about five days, over about 1 month, about 2 months, etc. It also can be administered prior, at the time of, or after other therapeutic interventions, such as surgical intervention to remove cancerous cells. The IQGAP1 SKIB can also be administered as part of a combination therapy, in which at least one of an immunotherapy, a cancer chemotherapy or a radiation therapy is administered to the subject (as described in greater detail below).

Disposition of the IQGAP1 SKIB and its corresponding biological activity within a subject is typically gauged against the fraction of IQGAP1 SKIB present at a target of interest. For example, a IQGAP1 SKIB once administered can accumulate with a glycoconjugate or other biological target that concentrates the material in cancer cells and cancerous tissue. Thus dosing regimens in which the IQGAP1 SKIB is administered so as to accumulate in a target of interest over time can be part of a strategy to allow for lower individual doses. This can also mean that, for example, the dose of IQGAP1 SKIB that are cleared more slowly in vivo can be lowered relative to the effective concentration calculated from in vitro assays (e.g., effective amount in vitro approximates mM concentration, versus less than mM concentrations in vivo).

As an example, the effective amount of a dose or dosing regimen can be gauged from the $IC_{50}$ of a given IQGAP1 SKIB for inhibiting cell migration. By "$IC_{50}$" is intended the concentration of a drug required for 50% inhibition in vitro. Alternatively, the effective amount can be gauged from the $EC_{50}$ of a given IQGAP1 SKIB concentration. By "$EC_{50}$" is intended the plasma concentration required for obtaining 50% of a maximum effect in vivo. In related embodiments, dosage may also be determined based on $ED_{50}$ (effective dosage).

In general, with respect to the IQGAP1 SKIB of the present disclosure, an effective amount is usually not more than 200× the calculated $IC_{50}$. Typically, the amount of an IQGAP1 SKIB that is administered is less than about 200×, less than about 150×, less than about 100× and many embodiments less than about 75×, less than about 60×, 50×, 45×, 40×, 35×, 30×, 25×, 20×, 15×, 10× and even less than about 8× or 2× than the calculated $IC_{50}$. In one embodiment, the effective amount is about 1× to 50× of the calculated $IC_{50}$, and sometimes about 2× to 40×, about 3× to 30× or about 4× to 20× of the calculated $IC_{50}$. In other embodiments, the effective amount is the same as the calculated $IC_{50}$, and in certain embodiments the effective amount is an amount that is more than the calculated $IC_{50}$.

An effect amount may not be more than 100× the calculated $EC_{50}$. For instance, the amount of IQGAP1 SKIB that is administered is less than about 100×, less than about 50×, less than about 40×, 35×, 30×, or 25× and many embodiments less than about 20×, less than about 15× and even less than about 10×, 9×, 9×, 7×, 6×, 5×, 4×, 3×, 2× or 1× than the calculated $EC_{50}$. The effective amount may be about 1× to 30× of the calculated $EC_{50}$, and sometimes about 1× to 20×, or about 1× to 10× of the calculated $EC_{50}$. The effective amount may also be the same as the calculated $EC_{50}$ or more than the calculated $EC_{50}$. The $IC_{50}$ can be calculated by inhibiting cell proliferation and/or cell migration/invasion in vitro. The procedure can be carry out by methods known in the art or as described in the examples below.

Effective amounts of dose and/or dose regimen can readily be determined empirically from assays, from safety and escalation and dose range trials, individual clinician-patient relationships, as well as in vitro and in vivo assays such as those described herein and illustrated in the Experimental section, below. For example, a concentration used for carrying out the subject method in mice ranges from about 1 mg/kg to about 25 mg/kg based on the body weight of the mice. Based on this data, an example of a concentration of the IQGAP1 SKIB that can be employed in human may range about 0.083 mg/kg to about 2.08 mg/kg. Other dosage may be determined from experiments with animal models using methods known in the art (Reagan-Shaw et al. (2007) *The FASEB Journal* 22:659-661).

Pharmaceutical Formulations

Also provided are pharmaceutical compositions containing the IQGAP1 SKIB employed in the methods of treatment described above. The term "IQGAP1 SKIB composition" is used herein as a matter of convenience to refer generically to compositions comprising an IQGAP1 SKIB of the present disclosure, including conjugated IQGAP1 SKIB, or both. Compositions useful for suppression the growth, i.e. proliferation, and/or metastasis of cancer cells are described below.

The IQGAP1 SKIB compositions, e.g., in the form of a pharmaceutically acceptable salt, can be formulated for oral, topical or parenteral administration, as described above. In certain embodiments, e.g., where a IQGAP1 SKIB is administered as a liquid injectable (such as in those embodiments where they are administered intravenously or directly into a tissue), an IQGAP1 SKIB formulation is provided as a ready-to-use dosage form, or as a reconstitutable storage-stable powder or liquid composed of pharmaceutically acceptable carriers and excipients.

Methods for producing IQGAP1 SKIB suitable for administration to a subject (e.g., a human subject) are described below. An example method of formulating IQGAP1 SKIB can involve a pharmaceutical composition containing an effective amount of a IQGAP1 SKIB and a pharmaceutical excipients (e.g., saline). The pharmaceutical composition may optionally include other additives (e.g., buffers, stabilizers, preservatives, and the like). An effective amount of IQGAP1 SKIB can be an amount effective to provide for a decrease of cancer metastasis (e.g. cancer migration and/or invasion). A therapeutic goal (e.g., reduction in tumor load and/or confinement of cancerous growth) can be accomplished by single or multiple doses under varying dosing regimen.

The concentration of IQGAP1 SKIB in the pharmaceutical formulations can vary from less than about 0.1%, usually at or at least about 2% to as much as 20% to 50% or more by weight, and will be selected primarily by fluid volumes, viscosities, etc., in accordance with the particular mode of administration selected and the patient's needs. The resulting compositions may be in the form of a solution, suspension, tablet, pill, capsule, powder, gel, cream, lotion, ointment, aerosol or the like. Actual methods for preparing parenterally administrable compositions will be known or apparent to those skilled in the art and are described in more detail in such publications as Remington's Pharmaceutical Science, 18th ed., Mack Publishing Company, NY (1995).

According to another aspect of this disclosure, IQGAP1 SKIBs can be included in a pharmaceutical or nutraceutical composition together with additional active agents, carriers, vehicles, excipients, or auxiliary agents identifiable by a person skilled in the art upon reading of the present disclosure.

The pharmaceutical or nutraceutical compositions preferably comprise at least one pharmaceutically acceptable carrier. In such pharmaceutical compositions, the IQGAP1 SKIBs form the "active compound," also referred to as the "active agent." As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for an injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor® EL (BASF, Parsippany, N.J.), or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. According to embodiments, isotonic agents, for example, sugars, polyalcohols such as manitol, sorbitol, or sodium chloride in the composition are added. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preparation is prepared by vacuum drying or freeze-drying, which yields a powder of the active ingredient plus any additional desired ingredient from a previously sterile-filtered solution thereof.

It is recognized that when administered orally, IQGAP1 SKIB should be protected from digestion. This is typically accomplished either by complexing the IQGAP1 SKIB with a composition to render it resistant to acidic and enzymatic hydrolysis or by packaging in an appropriately resistant carrier such as a liposome. Means of protecting a compound of interest from digestion are well known in the art.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or strawberry, cherry, grape, lemon, or orange flavoring.

For administration by inhalation, the compounds are delivered in the form of an aerosol spray from pressured container or dispenser which contains a suitable propellant, e.g., a gas such as carbon dioxide, or a nebulizer.

In order to enhance serum half-life, IQGAP1 SKIB preparations that are injected may also be encapsulated, introduced into the lumen of liposomes, prepared as a colloid, PEGylated (Greenwald et al. (2003) *Advanced Drug Delivery Rev.* 55:217-250; Pasut et al. (2004) Expert Opin. Ther. Patents 14:859-894) or other conventional techniques may be employed which provide an extended serum half-life. A variety of methods are available for preparing liposomes, as described in, e.g., Szoka et al. (1980) *Ann. Rev. Biophys.*

Bioeng. 9:467, U.S. Pat. Nos. 4,235,871, 4,501,728 and 4,837,028. The preparations may also be provided in controlled release or slow-release forms for release and administration of the IQGAP1 SKIB compositions as a mixture or in serial fashion.

According to embodiments, intravitreal injection is accomplished using PLGA-based microparticles or nanoparticles (liposomes). PEG-based formulas may also be used. Accordingly, the other methods for injectable pharmaceutical compositions are expressly contemplated for intravitreal injection.

Systemic administration can also be transmucosal or transdermal. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In addition to the other forms of delivery, the compounds are deliverable via eye drop or intraocular injection. With respect to eye drops, the compositions of the present disclosure optionally comprise one or more excipients intended for topical application to the eye or nose. Excipients commonly used in pharmaceutical compositions intended for topical application to the eyes, such as solutions or sprays, include, but are not limited to, tonicity agents, preservatives, chelating agents, buffering agents, surfactants and antioxidants. Suitable tonicity-adjusting agents include mannitol, sodium chloride, glycerin, sorbitol and the like. Suitable preservatives include p-hydroxybenzoic acid ester, benzalkonium chloride, benzododecinium bromide, polyquaternium-1 and the like. Suitable chelating agents include sodium edetate and the like. Suitable buffering agents include phosphates, borates, citrates, acetates and the like. Suitable surfactants include ionic and nonionic surfactants, though nonionic surfactants are preferred, such as polysorbates, polyethoxylated castor oil derivatives and oxyethylated tertiary octylphenol formaldehyde polymer (tyloxapol). Suitable antioxidants include sulfites, ascorbates, BHA and BHT. The compositions of the present disclosure optionally comprise an additional active agent. With the exception of the optional preservative ingredient (e.g., polyquaternium-1), the compositions of the present disclosure preferably do not contain any polymeric ingredient other than polyvinylpyrrolidone or polystyrene sulfonic acid.

When the compositions of the present disclosure contain polyvinylpyrrolidone, the polyvinylpyrrolidone ingredient is preferably selected or processed to minimize peroxide content. Freshly produced batches of polyvinylpyrrolidone are preferred over aged batches. Additionally, particularly in cases where the composition will contain greater than 0.5% polyvinylpyrrolidone, the polyvinylpyrrolidone ingredient should be thermally treated (i.e., heated to a temperature above room temperature) prior to mixing with olopatadine in order to reduce the amount of peroxides in the polyvinylpyrrolidone ingredient and minimize the effect of peroxides on the chemical stability of olopatadine. While thermally treating an aqueous solution of polyvinylpyrrolidone for prolonged periods will substantially reduce the amount of peroxides, it can lead to discoloration (yellow to yellowish-brown) of the polyvinylpyrrolidone solution. In order to substantially reduce or eliminate peroxides without discoloring the polyvinylpyrrolidone solution, the pH of the aqueous solution of polyvinylpyrrolidone should be adjusted to pH 11-13 before it is subjected to heat. Much shorter heating times are needed to achieve significant reductions in peroxide levels if the pH of the polyvinylpyrrolidone solution is elevated.

One suitable method of thermally treating the polyvinylpyrrolidone ingredient is as follows. First, dissolve the polyvinylpyrrolidone ingredient in purified water to make a 4-6% solution, then raise the pH of the solution to pH 11-13, (an effective range of pH is 11-11.5), then heat to a temperature in the range of 60-121° C., preferably 65-80° C. and most preferably 70-75° C. The elevated temperature should be maintained for approximately 30-120 minutes (preferably 30 minutes). After the heated solution cools to room temperature, add HCl to adjust the pH to 3.5-8, depending upon the target pH for the olopatadine composition.

Particularly for compositions intended to be administered as eye drops, the compositions preferably contain a tonicity-adjusting agent in an amount sufficient to cause the final composition to have an ophthalmically acceptable osmolality (generally 150-450 mOsm, preferably 250-350 mOsm). The ophthalmic compositions of the present disclosure preferably have a pH of 4-8, preferably a pH of 6.5-7.5, and most preferably a pH of 6.8-7.2.

The eye-drop compositions of the present disclosure are preferably packaged in opaque plastic containers. A preferred container for an ophthalmic product is a low-density polyethylene container that has been sterilized using ethylene oxide instead of gamma-irradiation.

With respect to ophthalmic injectables, the pharmaceutical compositions of this disclosure are administered to the area in need of treatment by subconjunctival administration. One preferred method of subconjunctival administration to the eye is by injectable formulations comprising the pharmaceutical compositions disclosed herein. Another preferred method of subconjunctival administration is by implantations comprising slow releasing compositions.

Compositions that are delivered subconjunctivally comprise, according to embodiments, an ophthalmic depot formulation comprising an active agent for subconjunctival administration. According to embodiments, the ophthalmic depot formulation comprises microparticles of essentially pure active agent. The microparticles comprising can be embedded in a biocompatible pharmaceutically acceptable polymer or a lipid encapsulating agent. The depot formulations may be adapted to release all of substantially all the active material over an extended period of time. The polymer or lipid matrix, if present, may be adapted to degrade sufficiently to be transported from the site of administration after release of all or substantially all the active agent. The depot formulation can be liquid formulation, comprising a pharmaceutical acceptable polymer and a dissolved or dispersed active agent. Upon injection, the polymer forms a depot at the injections site, e.g., by gelifying or precipitating.

Solid articles suitable for implantation in the eye can also be designed in such a fashion to comprise polymers and can be bioerodible or non-bioerodible. Bioerodible polymers that can be used in preparation of ocular implants carrying the compositions of the present disclosure include without restriction aliphatic polyesters such as polymers and copolymers of poly(glycolide), poly(lactide), poly(c-caprolactone), poly(hydroxybutyrate) and poly(hydroxyvalerate), polyamino acids, polyorthoesters, polyanhydrides, aliphatic polycarbonates and polyether lactones. Illustrative of suitable non-bioerodible polymers are silicone elastomers.

According to embodiments, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to cell-specific antigens) can also be used as pharmaceutically acceptable carriers.

The IQGAP1 SKIB composition can be administered as a single pharmaceutical formulation. It may also be administered with an effective amount of another agent that includes other suitable compounds and carriers, and also may be used in combination with other active agents. The present disclosure, therefore, also includes pharmaceutical compositions comprising pharmaceutically acceptable excipients.

The pharmaceutically acceptable excipients include, for example, any suitable vehicles, adjuvants, carriers or diluents, and are readily available to the public. The pharmaceutical compositions of the present disclosure may further contain other active agents as are well known in the art. Pharmaceutically acceptable excipients are also well-known to those who are skilled in the art, and are readily available.

For example, the IQGAP1 SKIB compositions can be admixed with conventional pharmaceutically acceptable carriers and excipients (i.e., vehicles) and used in the form of aqueous solutions, tablets, capsules, elixirs, suspensions, syrups, wafers, patches and the like, but usually the IQGAP1 SKIB will be provided as an injectable. The pharmaceutical compositions may contain common carriers and excipients, such as corn starch or gelatin, lactose, dextrose, sucrose, microcrystalline cellulose, kaolin, mannitol, dicalcium phosphate, sodium chloride, and alginic acid. Disintegrators commonly used in formulations include croscarmellose, microcrystalline cellulose, corn starch, sodium starch glycolate and alginic acid. Preservatives and the like may also be included. Each of these components is well-known in the art. Such pharmaceutical compositions contain, in certain embodiments, from about 0.1 to about 90% by weight of the active compound, and more generally from about 1 to about 30% by weight of the active compound. See, e.g., U.S. Pat. No. 5,985,310, the disclosure of which is herein incorporated by reference The IQGAP1 SKIB compositions can be provided in a pharmaceutically acceptable excipient, which can be a solution such as an aqueous solution, often a saline solution, or they can be provided in powder form. The IQGAP1 SKIB compositions may contain other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting.

A liquid composition will generally be composed of a suspension or solution of the compound or pharmaceutically acceptable salt in a suitable liquid carrier(s), for example, ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The IQGAP1 SKIBs of the present disclosure and their pharmaceutically acceptable salts that are active when given parenterally can be formulated for intramuscular, intrathecal, or intravenous administration. A typical composition for intramuscular or intrathecal administration will be of a suspension or solution of active ingredient in an oil, for example, arachis oil or sesame oil. A typical composition for intravenous or intrathecal administration will be a sterile isotonic aqueous solution containing, for example, active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol, a chelating agent, for example, ethylenediamine tetracetic acid, and an anti-oxidant, for example, sodium metabisulphite may be included in the formulation. Alternatively, the solution can be freeze dried and then reconstituted with a suitable solvent just prior to administration.

The IQGAP1 SKIBs of the present disclosure and their pharmaceutically acceptable salts which are active on rectal administration can be formulated as suppositories. A typical suppository formulation will generally consist of active ingredient with a binding and/or lubricating agent such as a gelatin or cocoa butter or other low melting vegetable or synthetic wax or fat.

The IQGAP1 SKIBs of the present disclosure and their pharmaceutically acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. No. 5,023,252, herein incorporated by reference in its entirety. Such patches may be constructed for continuous, pulsatile, or on demand delivery of pharmaceutical agents.

The formulations of the present disclosure can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

Formulations suitable for topical administration may be presented as creams, gels, pastes, or foams, containing, in addition to the active ingredient, such carriers as are known in the art to be appropriate.

Suppository formulations are also provided by mixing with a variety of bases such as emulsifying bases or water-soluble bases. Formulations suitable for vaginal administration may be presented as pessaries, tampons, creams, gels, pastes, foams.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more IQGAP1 SKIB. Similarly, unit dosage forms for injection or intravenous administration may comprise the IQGAP1 SKIB (s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present disclosure calculated in an amount sufficient to produce the desired effect in association with a pharmaceutically acceptable diluent, carrier or vehicle. The specifications for the novel unit dosage forms of the present disclosure depend on the particular compound employed and the effect to be achieved, and the pharmacodynamics associated with each compound in the host.

Those of skill in the art will readily appreciate that dose levels can vary as a function of the specific IQGAP1 SKIB, the nature of the delivery vehicle, and the like. Suitable dosages for a given compound are readily determinable by those of skill in the art by a variety of means.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the disclosure, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

The term "effective amount" refers to an amount of a biologically active molecule or conjugate or derivative thereof sufficient to exhibit a detectable therapeutic effect without undue adverse side effects (such as toxicity, irritation and allergic response) commensurate with a reasonable benefit/risk ratio when used in the manner of the invention. The therapeutic effect may include, for example but not by way of limitation, being substantially cytotoxic to cancer cells, but less cytotoxic to natural cells. The effective amount for a subject will depend upon the type of subject, the subject's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Materials and Methods

The following materials and methods are used in the examples that follow below.

Isolation and culture of primary human cells. Primary human epidermal keratinocytes and melanocytes as well as dermal fibroblasts were isolated from discarded neonatal surgical specimens. Briefly, specimens are cut into pieces to allow for removal of vascular and adipose tissue. Subsequently tissue is incubated overnight at 4° C. in a 1:1 dispase: PBS mixture containing 500 units/mL penicillin and 50 ug/mL streptomycin. The epidermis can then be peeled from the dermal tissue and placed in 0.05% trypsin at 37° C. for 5 minutes. The trypsin solution is quenched by adding a double volume of DMEM containing 10% FBS. The solution is rotated for 10 minutes at room temperature. Following low-speed centrifugation, the epidermal-cell containing pellet can be resuspended in keratinocyte serum-free media (GIBCO) supplemented with epidermal growth factor and bovine pituitary extract for growth of keratinocytes or Media 254 (GIBCO) supplemented with human melanocyte growth supplement for growth of melanocytes. The dermal tissue can be placed in 0.5 mg/mL collagenase solution at 37° C. for 1 hour followed by rocking for 20 minutes at room temperature. Solution is strained through a 70 um filter and subsequently neutralized by addition of a double volume of DMEM containing 10% FBS. Following low-speed centrifugation, the dermal-cell containing pellet can be resuspended in DMEM containing 10% FBS. Cells were grown at 37° C. in a humidifier chamber with 5% CO2.

Virus Production. Virus production was performed as previously described (Ridky, T. W., et al. Invasive three-dimensional organotypic neoplasia from multiple normal human epithelia. Nat Med 16, 1450-1456 (2010); Choate, K. A. and Khavari, P. A. Direct cutaneous gene delivery in a human genetic skin disease. Hum Gene Ther 8, 1659-1665 (1997)). Briefly, phoenix 293T packaging cells were transfected with plasmid DNA corresponding to retroviral expression vectors using Fugene 6.0 (Roche) and according to the manufacture's protocol. Alternatively, 293T cells were transfected with pCMV Δ8.91 expressing the core proteins and enzymes of HIV (gag and pol), pMD VSV-G providing the envelope protein of VSV-G, and plasmid DNA corresponding to lentiviral expression vectors using Fugene as above. 24-hours after transfection, cultures were placed at 32° C. 24- and 48-hours later, viral media was collected and strained through 0.45 um filter. Retroviral media is used immediately for transduction. Lentiviral media was concentrated by incubation at 4° C. overnight with Lenti-X concentrator (Clonetech). Following high-speed centrifugation, pellet virus is resuspended in 0.5-1 mL PBS and stored at −80° C. Handling of viral vectors was according to the guidelines of BSL-2 laboratories and Stanford University guidelines.

Retroviral Transduction. In order to malignantly transform keratinocytes, cells were infected with a single LTR-driven retrovirus expressing oncogenic H-RAS and a stabilized, dominantly acting version of the nuclear factor-κB (NF-κB) inhibitor IκBαM. Alternatively transformation was achieved through combined infection with an LTR-driven retrovirus expressing oncogenic ER:H-RAS and a separate LTR-driven retrovirus expressing cyclin-dependent kinase 4 (CDK4). Polybrene was added to a final concentration of 5 ug/mL to cell media during infection. Infections were performed at 37° C. with low-speed centrifugation for 1 hour. Expression of these viral constructs was verified in vitro. Oncogenic RAS, when combined with loosened G1 checkpoint restraints, has been shown in our lab to induce invasive neoplasia that recapitulates the cardinal histological features of squamous cell carcinoma (Khavari, P. A. Modeling cancer in human skin tissue. Nat Rev Cancer 6, 270-280 (2006); Dajee, M., et al. NF-kappaB blockade and oncogenic RAS trigger invasive human epidermal neoplasia. Nature 421, 639-643 (2003); Lazarov, M., et al. CDK4 coexpression with RAS generates malignant human epidermal tumorigenesis. Nat Med 8, 1105-1114 (2002); Lazarov, M., et al. Escaping G1 restraints on neoplasia—Cdk4 regulation by RAS and NF-kappa B. Cell Cycle 2, 79-80 (2003)). As a control for a RAS-IκBα bicistronic virus (IIR), we also infected a separate pool of keratinocytes with a LacZ control virus. For dual ER:H-RAS and CDK4 infected cells, forty-eight hours after infection cultures were daily treated with either 100 uM 40 hydroxytamoxifen or an equal volume of ethanol (vehicle).

siRNA-mediated knockdown. For each ERK/MAPK scaffold, siRNA oligos were designed and synthesized by Dharmacon. Subsequently, 1×10⁶ early-passage neonatal keratinocytes were electroporated with 2 nMol of each siRNA oligo or 1 nMol each of two siRNA oligos using Amaxa nucleofection reagents and according to the manufacturer's protocol. A nonfunctional siRNA served as a negative control and ERK1/2 siRNA served as positive controls. The following siRNA oligos were used for this study (sense/antisense):

```
siIQGAP1.A-
                                          (SEQ ID NO: 11)
GAA CGU GGC UUA UGA GUA CUU
                                          (SEQ ID NO: 12)
GUA CUC AUA AGC CAC GUU CUU siIQGAP1.B-
                                          (SEQ ID NO: 13)
CCU CUC GCU CUG AUG GGA CAU UUG U
                                          (SEQ ID NO: 14)
ACA AAU GUC CCA UCA GAG CGA GAG G siIQGAP1.C-
                                          (SEQ ID NO: 15)
CAG CCA UCA UGA CAU UUA CCA UGA A
                                          (SEQ ID NO: 16)
UUC AUG GUA AAU GUC AUG AUG GCU G siMEKK1.A-
                                          (SEQ ID NO: 17)
GAU UAG AUG UCA AUA CAG AUU
                                          (SEQ ID NO: 18)
UCU GUA UUG ACA UCU AAU CUU siKSR1..D-
                                          (SEQ ID NO: 19)
AGA AAG AGG UGA UGA ACU AUU
                                          (SEQ ID NO: 20)
UAG UUC AUC ACC UCU UUC UUU siMORG1.A-
                                          (SEQ ID NO: 21)
UGA ACA CGG UGC AGU UUA AUU
                                          (SEQ ID NO: 22)
UUA AAC UGC ACC GUG UUC AUU siARB1.C-
                                          (SEQ ID NO: 23)
GAA CUG CCC UUC ACC CUA AUU
                                          (SEQ ID NO: 24)
UUA GGG UGA AGG GCA GUU CUU siARB2.B-
                                          (SEQ ID NO: 25)
CGG CGU AGA CUU UGA GAU UUU
                                          (SEQ ID NO: 26)
AAU CUC AAA GUC UAC GCG GUU siMP1.A-
                                          (SEQ ID NO: 27)
CGG AUG ACC UAA AGC GAU UUU
                                          (SEQ ID NO: 28)
AAU CGU UUU AGG UCA UCC GUU siERK1.B-
                                          (SEQ ID NO: 29)
GAC CGG AUG UUA ACC UUU AUU
                                          (SEQ ID NO: 30)
UAA AGG UUA ACA UCC GGU CUU siERK2.B-
                                          (SEQ ID NO: 31)
GUA CAG GGC UCC AGA AAU UUU
                                          (SEQ ID NO: 32)
AAU UUC UGG AGC CCU GUA CUU
``` shRNA-mediated knockdown. The vectors for pGIPZ shRNA targeting IQGAP1 were designed and purchased through Open Biosystems catalog number V2LHS-86779 for shIQGAP1.E, V2LHS-86781 for shIQGAP1.F, and V2LHS-259635 for shIQGAP1.G. Cells were transduced as above with 1000× puromycin (1 mg/mL) selection applied daily. Transduction of cells was visualized under a fluorescent microscope qRT-PCR Expression Analysis. At indicated time points, RNA was harvested from cells via treatment with TRIZOL by the standard Invitrogen protocol. Relative mRNA expression was determined by qRT-PCR analysis using a Stratagene Mx3000P thermocycler and Brilliant II SYBR green QRT-PCR 1-step master mix reagents. Primer concentration was 200 nM with 100 ng RNA. Samples were run in triplicate and normalized to levels of GAPDH mRNA for each reaction. The following primers were used for this study:

```
IQGAP1.Reverse-
                                    (SEQ ID NO: 33)
TTC GCC ACT ACC CAG ACC TTG TTT IQGAP1.Reverse-
                                    (SEQ ID NO: 34)
CCT GTC TTG GAT GTG GCC TTT GG MEKK1.Forward-
                                    (SEQ ID NO: 35)
TTC AAC CTC AGG ACA GAC CTC CAT MEKK1.Reverse-
                                    (SEQ ID NO: 36)
ACT GGC CTC GTT CAT AGC TGT TCA KSR1.Forward-
                                    (SEQ ID NO: 37)
AGC AAG TCC CAT GAG TCT CA KSR1.Reverse-
                                    (SEQ ID NO: 38)
CAA CCT GCA ATG CTT GCA CT MORG1.Forward-
                                    (SEQ ID NO: 39)
CAG ACC GAT TTA AGG CTG CAA GCA MORG1.Reverse-
                                    (SEQ ID NO: 40)
TCC ACA TTA AAT CGT ACG GCT CGC ARB1.Forward-
                                    (SEQ ID NO: 41)
AGG CAT GAA GGA TGA CAA GGA GGA ARB1.Reverse-
                                    (SEQ ID NO: 42)
AAT CCT GAG GCC AGA GGT TCA TCA ARB2.Forward-
                                    (SEQ ID NO: 43)
GGA GAG GTG AGG GCA GGA TTA AGA ARB2.Reverse-
                                    (SEQ ID NO: 44)
GTA TGA ACA CAG CTT GCC ACC CA MP1.Forward-
                                    (SEQ ID NO: 45)
GCA TGC TTT GCG ACC TGG TTT CTT MP1.Reverse-
                                    (SEQ ID NO: 46)
TAG TCC TGT ATT GGC ACT GCT GCT GAPDH.Forward-
                                    (SEQ ID NO: 47)
GAA GAG AGA GAC CCT CAC TGC TG GAPDH.Reverse-
                                    (SEQ ID NO: 48)
ACT GTG AGG AGG GGA GAT TCA GT GFP.Forward-
                                    (SEQ ID NO: 49)
TGA CCC TGA AGT TCA TCT GCA GFP.Reverse-
                                    (SEQ ID NO: 50)
TCT TGT AGT TGC CGT CGT CCT
```

Protein Expression Analysis. Cells were lysed in 20 mM Tris (pH 7.5), 150 mM NaCl, 1 mM EDTA, and 1% NP40 supplemented with complete mini EDTA-free protease inhibitors (Roche) and phosphatase inhibitor cocktails I and II (Sigma-Aldrich). 5-20 ug of lysate were loaded per lane, subjected to 10-12% SDS-PAGE or 16% Tricine electrophoresus (Invitrogen NuPage), and subsequently transfer to PVDF membranes via semidry transfer. Primary antibody incubations were performed overnight at 4° C. Secondary antibody incubations were for 1 hour at room temperature. The following antibodies were used: rabbit anti-ERK1/2 (1:1000, Cell Signaling, 9201), rabbit anti-phosphorylated ERK1/2 (1:1000, Thr202/Tyr204, Cell Signaling, 9201), mouse anti-IQGAP1 (1:400, Upstate, 05-504), rabbit anti-RAS (1:500, Santa Cruz, sc-520), rabbit anti-IκBa (1:500, Cell Signaling, 9242), Rabbit anti-β-Galactosidase (1:1000, Cappel, 55976), rabbit anti myc (1:500, Abcam, ab9106), mouse anti-actin (1:10,000, Sigma, 5316), donkey anti-rabbit IgG conjugated to horseradish peroxidase (HRP)(1:20,000, Amersham Biosciences), and donkey anti-mouse IgG conjugated to horseradish peroxidase (HRP)(1:20,000, Amersham Biosciences).

IP-Kinase Assay. Cell Signaling p44/42 MAP Kinase Assay Kit immunoprecipitation-kinase (IP-kinase) assays were employed to evaluate perturbations to ERK/MAPK biochemical signaling following ablation of ERK/MAPK scaffolds according to the manufacturer's protocol. Briefly, genetically modified cells are lysed under non-denaturing conditions at defined time points post-treatment. Cell lysates are incubated overnight at 4° C. in the presence of immobilized monoclonal phosphorylated ERK primary antibody. Immunoprecipitated complexes are then mixed with an ELK-1 fusion protein and cold ATP. Samples were analyzed by gel electrophoresis and immunoblotting for mouse phosphorylated ELK-1 (1:1000, Serine 383, Cell Signaling, 9186).

Human Tissue Model System. Dermis can be ordered from National Disease Research Interchange (NDRI) and New York Firefighter Skin Bank. Tissue is inspected for overall thickness as well as continuity across the spectrum. Pieces with less hair follicles are preferable. This tissue is cultures in a mixture of antibiotics and antimyotics for a period of 10-14 days. Subsequently, the epidermis is peeled off. The devitalized dermis is then ready to be repopulated with $2-4 \times 10^5$ neonatal human fibroblasts by low speed centrifugation for 1 hour. Tissue is raised to the air-liquid interface and seeded with $0.5-1 \times 10^6$ genetically modified human keratinocytes to stimulate differentiation and stratification (Ridky, T. W., et al. Invasive three-dimensional organotypic neoplasia from multiple normal human epithelia. Nat Med 16, 1450-1456 (2010); PrunieRAS, M., et al. Methods for cultivation of keratinocytes with an air-liquid interface. J Invest Dermatol 81, 28-33 (1983)). Tissue was treated with drug/peptide as indicated by application directly into culture media daily. Tissue was grown for five to ten days total. For immunofluorescence analysis, tissue was placed in OCT. For histological analysis, tissue was fixed in 10% formalin (Sigma-Aldrich) and embedded in paraffin.

Immunofluorescence and Invasion index. OCT embedded tissue samples were cut into 7 um sections then fixed and permeabilized by incubation in ice-cold methanol or acetone for 10 minutes at −20° C. followed by blocking in 10% horse serum in PBS for 1 hour. Tissue sections were then incubated with primary antibodies, followed by Alexafluor-488 conjugated or Alexafluor-555 conjugated, goat anti-mouse or goat anti-rabbit secondary antibodies (Molecular Probes). The following antibodies were used: rabbit anti-keratin-5 (1:4000, Covance, PRB-160P), mouse anti-collagen VII (1:200, Millipore, MAB2500), anti-mouse Keratin 10 (1:200, Neomarkers, MS611P), anti-mouse Transglutaminase (1:100, Biomedical Technology, BT-621), anti-rabbit Loricrin (1:200, Covance, PRB-145P), and anti-rabbit Ki67 (1:100, Neomarkers, SP6). Tissue was counterstained with Hoescht to visualize cell nuclei. Microscopy was performed on an Olympus FV1000 scanning laser confocal microscope. For each sample, 30 sequential Z-sections were taken in 3 channels (DAPI—405/450 nm excitation/emission, FITC-488/512 ex/em and TRITC-540/570 ex/em) allowing for subsequent three-dimensional reconstruction analysis. Image analysis and 3D reconstruction was performed using Improvision Volocity software (Perkin Elmer). Relative invasion index was quantified as number of keratin-positive epithelial cells below the collagen-positive basement membrane zone (BMZ) measured 10 times across 3 independent 20× fields of view. Ki67 quantification was quantified as number of Ki67-positive epithelial cells measured 10 times across 3 independent 20× fields of view.

Immunohistochemistry. De-waxed paraffin slides or tissue microarrays were treated with heated antigen unmasking reagent (vector labs H-3300). Subsequently, endogenous peroxidase activity was quenched by treatment with 3% $H_2O_2$ followed by blocking in 10% horse serum in PBS for 1 hour. The following antibodies were used rabbit anti-phosphorylated ERK (1:25, Thr202/Tyr204, Cell Signaling, 4370), rabbit anti-ERK (1:100, Cell Signaling, 4695), and mouse anti-IQGAP1 (1:25, Invitrogen, 33-8900). Subsequently, slides were stained with biotinylated horse anti-rabbit IgG as secondary antibody and counterstained with ABC-elite HRP (RTU Vectastain Universal elite ABC kit). Slides were developed using DAB+ substrate chromogen system (Dako Cytomation k3467) and counterstained with hematozylin and PBS blueing. Slides were mounted in a xylene-based medium Cytoseal-XYL (Richard Allan Scientific) and visualized on Leica DM LB microscope. Sections were stained with hematoxylin and eosin (H&E) for histology. Tissue microarrays were scored blinded on the basis of IQGAP1 stain.

Genotyping and Mouse Handling. All mouse husbandry and experimental procedures were performed in accordance and compliance with policies approved by the Stanford University Administrative Panel on Laboratory Animal Care (Khavari lab protocol #9863). Mice were housed and bred under standard conditions with food and water ad libitum and maintained on a 12-hour light/dark cycle. IQGAP1 knockout mice were maintained in a C57BU6 and 129 mixed background. Genotyping was performed using genomic DNA isolated from mouse tails in DirectPCR lysis regent (Viagen). Primers used for gene amplification were p5 5'-TTG CAG TCT GTG GCA TGT G-3' (SEQ ID NO:51) and p3 5'-CCT GCT GAC AGG TCA ATG AT-3' (SEQ ID NO:52) for wild-type IQGAP1 allele or p5 5'-TTG CAG TCT GTG GCA TGT G-3' (SEQ ID NO:53) and pNeo 5'-CCT GCT CTT TAC TGA AGG CT-3' (SEQ ID NO:54) for neomycin cassette. K14-ER:RAS transgenic mice, Jax stock number 006403, were kept in a 129/SvEv background. This line was crossed to IQGAP1 knockout mice and subsequently backcrossed to C57BU6 and 129 wildtype mice. The ER:RAS transgene was detect with the following primers: Forward 5'-CAC CAC CAG CTC CAC TTC AGC ACA TT-3' (SEQ ID NO:55) and Reverse 5' CGC ACC AAC GTG TAG AAG GCA TCC TC-3' (SEQ ID NO:56). Gender-matched littermates were used for all experiments.

Isolation and culture of primary murine cells. Primary murine epidermal keratinocytes were isolated from neonatal animals. Animals were anesthetized by treatment with isoflurane for no less than 20 minutes and subsequently euthanized by cervical decapitation Subsequently epidermal tissue is incubated overnight at 4° C. in a 1:1 dispase:HBSS mixture containing 200 μL of gentamycin. The epidermis can then be peeled from the dermal tissue and placed in 0.05% trypsin at 37° C. for 15 minutes with frequent shaking. The trypsin solution is quenched by adding a double volume of 15% FBS in HBSS. Following low-speed centrifugation, the epidermal-cell containing pellet can be resuspended in CnT-02 media and strained through a 70 um filter. Cells were grown at 37° C. in a humidifier chamber with 5% CO2.

Wound healing. Two round, full-thickness excision wounds, 6 mm in diameter were made on the dorsal skin of anesthetized 6-8 week old mice using sterile biopsy punches. Untreated wounds were measured for closure and photographed at least once every 3 days. Percent wound closure was measured as wound area compared to initial wound.

DMBA/TPA Chemical Carcinogenesis. The backs of anesthetized 8- to 10-wk-old mice were shaved and treated two-times (3 days apart) with application of 7,12-dimethylbenz(a)anthracene (DMBA, Sigma; 10 ug in 100 uL acetone) followed by twice weekly application of 12-O-tetradecanoylphorbol-13-acetate (TPA, Sigma: 12.5 ug in 100 uL acetone). Papillomas were observed twice per week for thirty weeks and recorded by photography and caliper measurement of length, width and depth. Tumor volume was estimated using the formula $4/3\pi(r1r2r3)$ where r1=length, r2=width, r3=height.

Acute Oncogenic RAS. The lower backs of anesthetized 6-8 week old mice were shaved and a 6-day, once-daily application of 1 mg/0.1 mL 4OHT (Sigma-Aldrich) in ethanol was used to activate the ER:RAS transgene. Relative hyperproliferation was quantitated by the thickness of interfollicular epidermis from the basal layer to the top of the stratified layer (not including the cornified layer) using a micrometer and measured 10 times across 3 independent 20× fields of view. Values were normalized to control.

In Vivo Xenografts. $1 \times 10^6$ genetically modified human cancer cell lines or transformed murine epithelial cells were injected into the subcutaneous space of anesthetized immunodeficient (SCID) 6-8 week old mice in a volume of 200 μL containing 50% matrigel (BD Biosciences). Tumors were allowed to develop 4-8 weeks. Tumors were observed at least twice per week and recorded by photography and caliper measurement of length, width and depth. Tumor volume was estimated using the formula $4/3\pi(r1r2r3)$ where r1 is the length (in mm), r2 is the width (in mm), and r3 is the height (in mm).

In addition, tumors were quantified through in vivo bioluminescence as cells were co-infected with retroviral vector encoding firefly luciferase. Luciferin was resuspended to 15 mg/ml and mice were IP injected with 10 ul per gram of body weight. Signal was allowed to plateau following injection of substrate. Luciferase signal as average radiance (photon/second/$cm^2$/steridian) value was recorded using Xenogen IVIS-200 imaging system and Living Image 3.2 software (Lim, E., et al. In vivo bioluminescent imaging of mammary tumors using IVIS spectrum. J V is Exp 26, 1-2 (2009)).

Cloning and Mutagenesis of IQGAP1 WW domain. The pLEX-mycWW clone was PCR amplified from pCR-BluntII-TOPO IQGAP1 (Openbiosystems, catalog MHS4426-99626202) using the following primers: Forward 5'-GCT CGC GGA TCC ACC ATG GAA CAA AAA CTT ATT TCT GAA GAA GAT CTG GAT AAT AAC AGC AAG TGG GTG AAG CAC-3' (SEQ ID NO:57) and Reverse 5' ATA AGT GCG GCC GCT TAT GGG GGT TCA TCC CAT CCT CCT TCC TG-3' (SEQ ID NO:58). PCR products were subsequently digested with BamH1 and Not1 restriction enzymes and ligated into LentiORF pLEX-MCS vector (Openbiosystems, catalog OHS4735). To generate the pLEX-mycYY (mutant WW) clone, QuikChange Site directed mutagenesis methodology (Stratagene) was employed. The following primers were used to mutate tyrosine 696 and tyrosine 697 to alanine: Forward 5'-GGT GAA GCA CTG GGT AAA AGG TGG ATA TTA TGC TGC CCA CAA TCT GGA GAC C-3' (SEQ ID NO:59) and Reverse 5'-GGT CTC CAG ATT GTG GGC AGC ATA ATA TCC ACC TTT TAC CCA GTG CTT CAC C-3' (SEQ ID NO:60).

Regression of established tumors. Mouse xenografts were allowed to grow untreated for 3-4 weeks. Subsequently, tumors were measured and equally divided depending on size into groups for experimental manipulation. Groups received 5 treatments of 200uLempty, WW or mutant WW lentivirus, intratumorally as indicated in the discussion below every 3 days over the course of two weeks. Tumors were observed at least twice per week and recorded by photography and caliper measurement of length, width and depth. Tumor volume was estimated using the formula $4/3\pi(r1r2r3)$.

Cell Viability Assay. Genetically modified adherent cancer cell lines were seeded in equivalent, low density cultures in duplicate to 24-well plates. 24 hours post-seeding, media was removed and replaced with 500 uL of a 5:1 mixture of cell media and cell titre blue reagent (Promega). Cultures were incubated with this mixture for 2 hours at 37° C. in the dark. Fluorescence (560 nm emission/590 nm excitation) for 100 uL in triplicates of each sample was recorded. Incubation with cell titre blue reagent and fluorescent readings were repeated every two days for a total of twelve days. Values plotted correspond to readings taken while control samples are still growing exponentially.

Cancer Cell Lines. The following cancer cell lines from the ATCC and collaborators at Stanford University were employed in this study (identified in text, cell line name, ERK/MAPK aberration, and media):

Breast Cancer Cell Line 1:MDA-MB-468, overexpress EGFR, DMEM with 10% FBS
Breast Cancer Cell Line 2: MDA-MB-231, KRAS mutation, DMEM with 10% FBS
Breast Cancer Cell Line 3: SK-BR-3, overexpress HER2, Ham's F12 with 10% FBS
Breast Cancer Cell Line 4: MCF7, NRAS mutation, DMEM with 10% FBS
Colorectal Cancer Cell Line 1: HCT-116, KRAS mutation, DMEM with 10% FBS
Colorectal Cancer Cell Line 2: HT-29, BRAF mutation, RPMI with 10% FBS
Prostate Cancer Cell Line 1: DU-145, overexpress EGFR, DMEM with 10% FBS
Prostate Cancer Cell Line 2: PC-3, overexpress EGFR, DMEM with 10% FBS
Melanoma Cancer Cell Line 1: SK-Mel-5, BRAF mutation, DMEM with 10% FBS
Melanoma Cancer Cell Line 2: Colo-829, BRAF mutation, RPMI with 10% FBS (also identified as BRAF V600E Melanoma)
Melanoma Cancer Cell Line 3: MM485, NRAS mutation, RPMI with 10% FBS (also identified as NRAS Q61 L Melanoma)
Melanoma Cancer Cell Line 4: CHL1, wild-type RAS and RAF, DMEM with 10% FBS (also identified as WT Melanoma)

Production of cells which are resistant to PLX-4032. Cells were made resistant to PLX-4032 as previously described (Nature 468:968, 2010 and Nature 468:973, 2010). Briefly, BRAFV600E cancer cell lines were grown in low doses of PLX-4032 (1 µM in DMSO, Active Biochem) for 6-8 weeks until pErk levels were increased and cells were no longer sensitive to increased doses of PLX-4032 (5 µM).

Immunoprecipitation of endogenous IQGAP1 protein and associated Erk. Cells were cross-linked with 1 mL of 20 mM DSP (Thermo Scientific) for 1 hour at 4° C. and the reaction was stopped with washes in 50 mM Tris. Cells were lysed in 20 mM Tris, 150 mM NaCl, 0.2% NP40, 10% Glycerol with 0.5 mM dTT and protease/phosphatase inhibitors added directly before use (buffer 1) for 1 hour at 4° C., but not pelleted. 1 mg lysate in 500 uL was combined with 5 ug of mouse anti-IQGAP1 antibody (Millipore 05-504) in buffer 1 and rocked overnight at 4° C. 30 uL of protein G sepharose 4 fast flow (GE Healthcare) were washed in buffer 1 and combined with lysate for 1 hour at 4° C. Supernatent was removed to check for immunodepletion. Beads were washed 3 times in 20 mM Tris, 150 mM NaCl, 1% Triton X-100 with protease/phosphatase inhibitors added directly before use (buffer 2). Immunoprecipitate was eluted from beads in 200 uL of 4×LDS sample buffer in buffer 1 plus 5% BME. Immunoblots were performed with the following antibodies used: rabbit anti-Erk1/2 (1:1000, Cell Signaling, 9201) and rabbit anti-IQGAP1 (1:500, Abcam, 86064).

Exogenous delivery of the WW domain to human tissue. Human tissue was regenerated as previously described (Ridky, T. W., Chow, J. M., Wong, D. J. & Khavari, P. A. Invasive three-dimensional organotypic neoplasia from multiple normal human epithelia. Nature medicine 16, 1450-1455 (2010)). Briefly stromal primary human fibroblasts were seeded onto devitalized human dermis and subsequently elevated to a sterilized annular dermal support (ADS) tissue culture insert device (Ridky, supra). Primary keratinocytes were transduced with viral constructs as previously described (Ricky, supra). These cells were then seeded to the air-liquid interface of the upper chamber of the ADS insert with media changed daily. In response to 4-hydroxytamoxifen (4OHT, Sigma 100 nM in ethanol), cell expressing inducible ER-HRas$^{G12V}$ invaded into the underlying dermis within ~5 days. Immunoflourescence was performed as previously described (Scholl, F. A., et al. Mek1/2 MAPK kinases are essential for Mammalian development, homeostasis, and Raf-induced hyperplasia. Developmental cell 12, 615-629 (2007)). Microscopy was performed on an Olympus FV1000 scanning laser confocal microscope. For each sample, 30 sequential Z-sections were taken in 3 channels (DAPI—405/450 nm excitation/emission, FITC-488/512 ex/em and TRITC-540/570 ex/em) allowing for subsequent three dimensional reconstruction analysis. Image analysis and 3D reconstruction was performed using Improvision Velocity software (Perkin Elmer). X-Y plane are three-color images (red, green, and blue), while Z-X planes are restricted to two colors (red and green) for ease of viewing effects on BMZ. Peptides corresponding to R8-myc-tagged Scrambled sequence, R8-myc-tagged WW domain, and R8-myc-tagged Mutant-WW domain were synthesized by Biomatik and by Stanford Biomaterials and Advanced Drug Discovery laboratories in acetate salt and resuspended in water to a 2.5 mM working solution. Peptide was added directly into the media of tissue culture at concentration as indicated.

Systemic delivery of WW peptide in vivo. $0.5 \times 10^6$ luciferase-expressing SK-Mel-28 were injected into the subcutaneous space of hairless immunodeficient 6-8 week old SCID mice (SHO stock, Charles Rovers). Mouse xenografts were allowed to grow untreated for 1 week. Subsequently, tumors were measured and randomized two groups of similar tumor size. Each group was subcutaneously implanted with osmotic pumps (Alzet, model 2002) releasing 0.5 uL of R8-myc-tagged scrambled or WW peptide per hour for 14 days.

Statistics. Standard deviation was employed for all analysis. Further analysis of variance and subsequent post hoc comparisons employed two-tailed, two-sample equal variance (homoscedastic) Student's t-tests.

Example 1

Results

ERK/MAPK pathway is required for RAS-driven epithelial neoplastic invasion. To generate models of epithelial neoplasia as well as normal homeostatic tissue, primary human keratinocytes were isolated from neonatal foreskin and transformed with oncogenic RAS and a stabilized and dominantly acting version of the nuclear factor-κB (NF-κB) inhibitor IκBα (IκBαM) that mediates escape from cell cycle arrest (Dajee, M., et al. NF-kappaB blockade and oncogenic RAS trigger invasive human epidermal neoplasia. Nature 421, 639-643 (2003); Lazarov, M., et al. CDK4 coexpression with RAS generates malignant human epidermal tumorigenesis. Nat Med 8, 1105-1114 (2002); Choate, K. A. and Khavari, P. A. Direct cutaneous gene delivery in a human genetic skin disease. Hum Gene Ther 8, 1659-1665 (1997)). These keratinocytes were subsequently seeded onto devitalized human dermis and raised to the air-liquid interface to initiate differentiation and regeneration of organotypic tissue (Ridky, T. W., et al. Invasive three-dimensional organotypic neoplasia from multiple normal human epithelia. Nat Med 16, 1450-1456 (2010)). Cultures of keratinocytes expressing a control virus (LacZ) remain bound by the basement membrane zone (BMZ) and in the epithelial compartment of the tissue (left panel, FIG. 2A), whereas those expressing neoplastic mediators invade into the underlying dermis with a characteristic degradation of the BMZ (left panel, FIG. 2B) as confirmed by immunostains for keratin 5 and type-VII collagen (Dajee, M., et al. NF-kappaB blockade and oncogenic RAS trigger invasive human epidermal neoplasia. Nature 421, 639-643 (2003)). This model system allowed us to assay key pathway inhibitors at well-tolerated concentrations in normal tissue (FIG. 2A) and subsequently at the same concentration in transformed tissue for their ability to affect neoplastic invasion (FIG. 2B) (Ridky, T. W., et al. Invasive three-dimensional organotypic neoplasia from multiple normal human epithelia. Nat Med 16, 1450-1456 (2010)).

UO126, a potent MEK1 and MEK2 inhibitor, is the only identified drug capable of completely inhibiting invasion without affecting normal tissue homeostasis (FIGS. 2A, and 2B) (Favata, M. F., et al. Identification of a novel inhibitor of mitogen-activated protein kinase kinase. J Biol Chem 29, 18623-18632 (1998)). All other drugs tested were much less effective at blocking neoplastic invasion (FIG. 2C) (Ridky, T. W., et al. Invasive three-dimensional organotypic neoplasia from multiple normal human epithelia. Nat Med 16, 1450-1456 (2010)). SB203580 inhibits the stress- and inflammatory cytokine-activated p38 MAPK pathway through its competitive binding of ATP, but does not affect ERK/MAPK signal output and did not completely block invasion. The phosphatidylinositol 3 (PI3) kinase inhibitor LY294002 blocks downstream phosphorylation of AKT and functions by competitively inhibiting ATP from the catalytic subunit. LY294002 does not affect ERK/MAPK signaling and neoplastic invasion proceeded in spite of the presence of this drug. Interestingly, the selective MEK1 inhibitor, PD098059 also did not have an abrogating effect on neoplastic invasion even at very high concentrations (Favata, M. F., et al. Identification of a novel inhibitor of mitogen-activated protein kinase kinase. J Biol Chem 29, 18623-18632 (1998)). Treating keratinocytes with U0126 results in diminished phosphorylation of ERK with no apparent effect on total ERK (FIG. 2D). Taken together, these findings demonstrate the importance of signaling through the ERK/MAPK pathway as a key regulator in cancer (FIG. 1) (Khavari, P. A. Modeling cancer in human skin tissue. Nat Rev Cancer 6, 270-280 (2006); Ridky, T. W., et al. Invasive three-dimensional organotypic neoplasia from multiple normal human epithelia. Nat Med 16, 1450-1456 (2010)).

Figure 3:
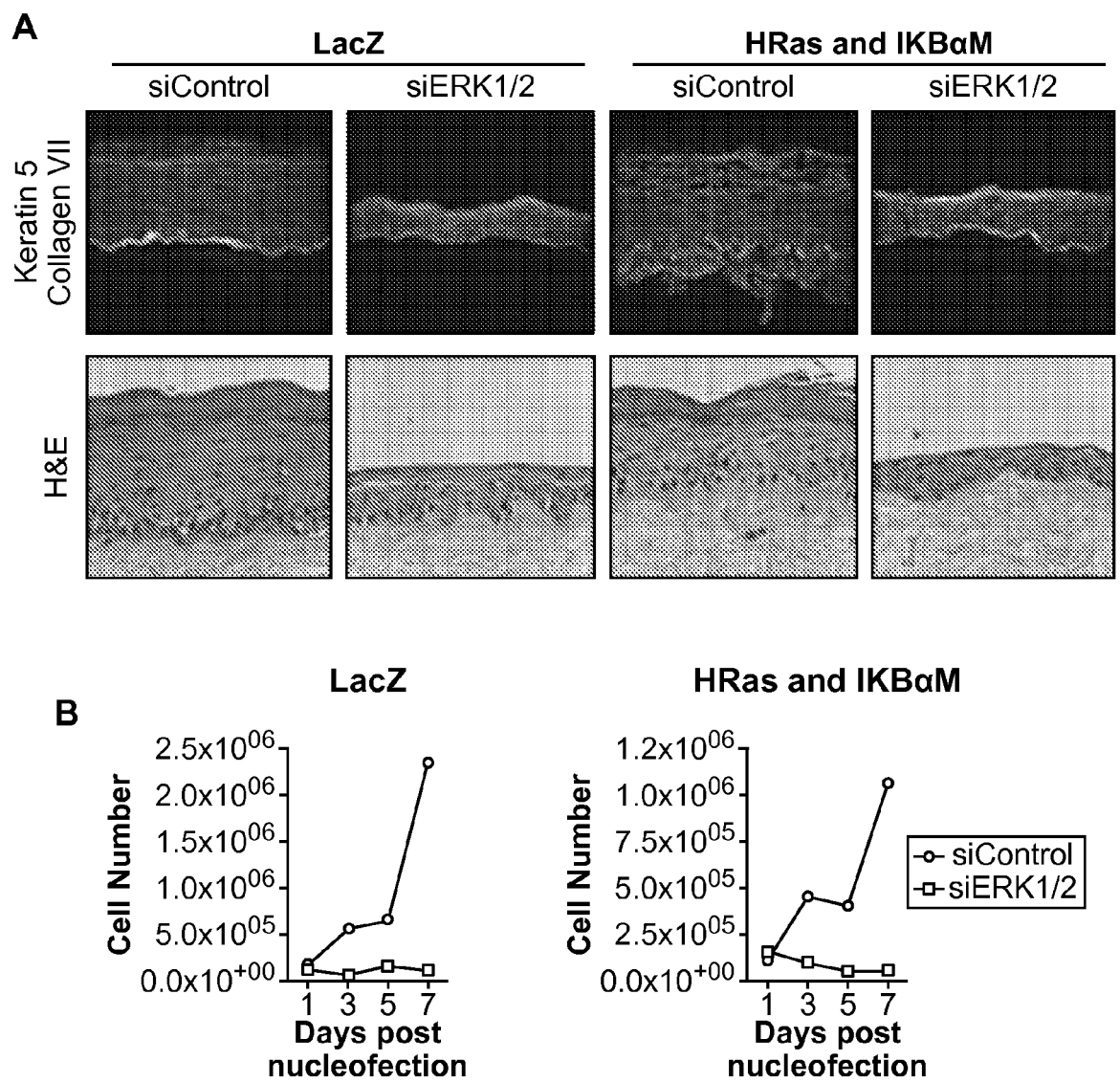
FIG. 3 depicts that ERK is necessary for normal tissue and RAS-induced neoplastic invasion. (A) Immunofluorescence staining (upper) of the epithelial marker keratin 5 (orange) and the basement membrane zone (BMZ) protein type-VII collagen (green) and corresponding immunohistochemistry staining (lower) of LacZ (left) or H-RAS$^{G12V}$/IκBαM (right) organotypic human tissue expressing siRNAs targeting a non-functional control sequence or ERK1/ERK2 sequences. All stains are representative images for at least 3 independent experiments. (B) Proliferation assays on primary keratinocytes expressing LacZ or H-RAS$^{G12V}$/IκBαM and nucleofected with siRNAs as in (A). Cells were seeded at an equal density and cell counts were performed every 2 days.

Targeting ERK is not a viable therapeutic. To precisely investigate the role of the most downstream member of the ERK/MAPK cascade in RAS-driven tumorigenesis, siRNAs targeting ERK1 and ERK2 were employed. Organotypic cultures regenerated with these cells showed drastic effects. As expected based on results with UO126, no invasion was observed in neoplastic tissue (FIG. 3A, right panels). However, siERK1/2 normal tissue was distinctly hypoplastic as compared to control (FIG. 3A, left panels). Furthermore, this tissue failed to form a stratum corneum, highlighting the barrier defects observed in previous work by Dumesic et al. (FIG. 3A, bottom panels) (Dumesic, P. A., et al. ERK1/2 MAP kinases are required for epidermal G2/M progression. J Cell Biol 185, 409-422 (2009)). Moreover, proliferation assays revealed that siERK1/2 nucleofected keratinocytes failed to proliferate as robustly as control cells in both normal and neoplastic conditions. Thus, while ERK is undoubtedly a key component of this pathway and activated ERK has a role in neoplastic invasion, ERK is also required for normal tissue development and function. As such, targeting the ERK kinases is simply not a viable therapeutic option.

Targeting ERK by targeting ERK/MAPK scaffolds. Having established the importance of the ERK/MAPK cascade in neoplastic tissue, we characterized several ERK/MAPK scaffold proteins in our human tissue model system (FIG. 4). Employing siRNAs that mediate robust knockdown of these scaffolds (FIG. 5B), we found that IQGAP1 is required for RAS-mediated epithelial neoplastic invasion (FIGS. 5A and 5C). It is interesting to note that with knockdown of other ERK/MAPK scaffolds, including KSR1 and MP1, invasion was only slightly diminished, when compared to the lack of invasion observed in IQGAP1 depleted cells (FIGS. 5A and 5C). Moreover, IQGAP1 levels did not change suggesting that there was no compensation nor modulation of IQGAP1 levels in cells with siRNA-mediated knockdown of other ERK/MAPK scaffold (FIG. 5D). This data indicates that a correlation exists between cell exhibiting normal levels of IQGAP1 and their ability to invade.

Collectively, these data demonstrate a model whereby RAS-mediated tumorigenesis requires signaling through the ERK/MAPK cascade such that ablation of active ERK by drug or direct targeting prevents neoplastic invasion. However, since depletion of active ERK also causes massive deleterious effects to the normal tissue, our data highlights the difficulty of directly targeting MAP kinases therapeutically. This led us to explore depletion of associated ERK/MAPK scaffolds as mediators of cascade dynamics. We demonstrated that IQGAP1 knockdown inhibits neoplastic invasion in our human tissue model system.

Discussion

Targeting kinases in crucial signaling cascades in cancer. Carcinogenesis as depicted by Hanahan and Weinberg (2000) is best described by six key characteristics—limitless growth, ability to replicate infinitely, inhibition of apoptosis, evasion of growth suppression, ability to migrate, and capacity to recruit a blood supply (Hanahan, D. and Weinberg, R. A. The hallmarks of cancer. Cell 100, 57-70 (2000)). Each of these characteristics can be mediated through dysregulation of normal signal transduction. Thus, we were motivated to explore the role of inhibiting key signaling cascades in cancer as a way to target these hallmarks—an idea highlighted in the most recent review by Hanahan and Weinberg (2011) (Hanahan, D. and Weinberg, R. A. Hallmarks of cancer: the next generation. Cell 144, 646-674 (2011)).

By employing primary neonatal cells to engineer human tissue model systems of normal, non-transformed tissue as well as RAS-driven neoplastic tissue, we were able to screen a group of known drug inhibitors for their ability to inhibit invasion without affecting normal tissue homeostasis (Ridky, T. W., et al. Invasive three-dimensional organotypic neoplasia from multiple normal human epithelia. Nat Med 16, 1450-1456 (2010)). Traditionally, tumorigenesis screens have relied on in vitro measures of neoplastic potential, such as soft agar growth assays. However, these surrogates do not always faithfully model human tumorigenesis (Khavari, P. A. Modeling cancer in human skin tissue. Nat Rev Cancer 6, 270-280 (2006)). Furthermore, mouse models of drug screens are complicated by an ability to introduce these drugs in vivo (Ridky, T. W., et al. Invasive three-dimensional organotypic neoplasia from multiple normal human epithelia. Nat Med 16, 1450-1456 (2010)). Thus our systems employing known gene modifications to human primary cells and introduction of drug concentrations at levels that did not adversely affect normal tissue is technically feasible and a biologically relevant approach. Employing these screens, we identified the MEK1 and MEK2 inhibitor U0126 for its potent ability to prevent neoplastic invasion. Interestingly, U0126 inhibits both active forms and activation of inactive forms of MEK1 and MEK2, whereas PD098059 only inhibits activation of inactive MEK1 and did not block invasion (Favata, M. F., et al. Identification of a novel inhibitor of mitogen-activated protein kinase kinase. J Biol Chem 29, 18623-18632 (1998)). This data supports finding by Scholl et al. (2009) that mouse tissue retaining one allele of either MEK1 or MEK2 was intermediately responsive to acute oncogenic RAS signaling in the epidermis, whereas tissue lacking all MEK1 and MEK2 alleles completely abolished RAS effects (Scholl, F. A., et al. MEK1/2 gene dosage determines tissue response to oncogenic RAS signaling in the skin. Oncogene 12, 1485-1495 (2009)). Furthermore Scholl et al. (2009) also showed that MEK1 knockout mice developed fewer RAS-driven papillomas than wildtype or heterozygous counterparts suggesting that by targeting both active and inactive forms UO126 is able to inhibits MEK1 more effectively than PD098059 and thus affect a more robust phenotype (Scholl, F. A., et al. Selective role for MEK1 but not MEK2 in the induction of epidermal neoplasia. Cancer Res 69, 3772-3778 (2009)). Further supporting the role of the ERK/MAPK pathway's role in mediating RAS-driven neoplastic invasion, we did not see effects following introduction of the p38 MAPK inhibitor SB203580 or the PI3K inhibitor LY294002. Additional work screening 20 total inhibitors and employing this methodology, Ridky et al. (2010) identified UO126 as the only drug capable of fully inhibiting invasion into the underlying dermis (Ridky, T. W., et al. Invasive three-dimensional organotypic neoplasia from multiple normal human epithelia. Nat Med 16, 1450-1456 (2010)). To counteract non-specific interactions and possible side effects, we knocked down the most downstream effector kinases ERK1 and ERK2 and characterizing the resultant phenotype. However, targeting the ERK kinases directly disrupts crucial cellular growth pathways, giving rise to massive defects that exclude this approach as a viable therapeutic modality. This data is supported by elegant in vivo mouse modeling, which showed ERK1/2 necessity in the epidermis for cell cycle progression (Dumesic, P. A., Scholl, F. A., Barragan, D. I., and Khavari, P. A. ERK1/2 MAP kinases are required for epidermal G2/M progression. J Cell Biol 185, 409-422 (2009)). Thus, through use of our human tissue model system, we have confirmed that targeting ERK directly is not a viable therapeutic option due to its participation in a large number of pathways involved in cellular homeostasis such as survival, migration, and proliferation.

Scaffolds as selective tumor targets. By selectively inhibiting interacting proteins found in the ERK/MAPK cascade, we identified IQGAP1 as the sole ERK/MAPK scaffold to completely abolish epithelial cell invasion in our neoplastic human tissue model system while sparing essential cellular processes. Previous work in the field has implicated additional ERK/MAPK scaffolds in mediating tumorigenesis (Kolch, W. Coordinating ERK/MAPK signaling through scaffolds and inhibitors. Nature Rev Mol Cell Bio 6, 827-837 (2005); Sacks, D. B. The role of scaffold proteins in MEK/ERK signaling. Biochem Soc Trans 34, 833-836 (2006)). However, in our studies we only observed moderate changes in invasion compared to control upon knockdown ERK/MAPK scaffolds MEKK1, KSR1, MORG1, ARB1, ARB2, and MP1. While Nguyen et al. (2002) demonstrated that KSR1 knockout animals develop polyomavirus MT-mediated mammary tumors at a slower rate than wildtype littermates, this work also highlighted that tumors still formed in these animals. Similarly, Lozano et al. (2003) also showed that while some H-RAS-mediated tumors formed in KSR1 null mice, there were overall fewer tumors than those observed in control animals (Lozano, J., et al. Deficiency of kinase suppressor of RAS1 prevents oncogenic RAS signaling in mice. Cancer Res 63, 4232-4238 (2003)). In both studies, however, tumors still formed in KSR1 knockout animals. While KSR1 knockdown diminished neoplastic invasion somewhat compared to control, invasion was still observed. In contrast, our data indicates that IQGAP1 knockdown is the only method capable of fully blocking invasion through the basement membrane.

Since scaffolds are known to associate with different partners in response to certain signals or subcellular locations, and that each scaffold rather than acting globally to effect change, modulates a certain subset of signaling events (Casar, B., et al. RAS subcellular localization defines extracellular signal-regulated kinase 1 and 2 substract specificity through distinct utilization of scaffold proteins. Mol Cell Biol 5, 1338-1353 (2009); Nguyen A., et al. Kinase suppressor of RAS (KSR) is a scaffold which facilitates mitogen-activated protein kinase activation in vivo. Mol Cell Biol 22, 3035-3045 (2002); Rocks, O., et al. Spatio-temporal segregation of RAS signals: one ship, three anchors, many harbors. Curr Opin Cell Biol 18, 351-357 (2006)), we believe that IQGAP1 functions in part as a RAS-mediated tumor-selective scaffold that mediates oncogenic signaling through this cascade to support continual growth, inhibition of apoptosis, and migration (Hanahan, D. and Weinberg, R. A. The hallmarks of cancer. Cell 100, 57-70 (2000)). Given the near ubiquity of cancer-associated activating mutations in this pathway, tumor-selective targets such as IQGAP1 that can be therapeutically inhibited without affecting normal tissue homeostasis represent new and viable effectors for drug development (FIG. 1).

Example 2

Results

IQGAP1 is a tumor Selective target. To confirm the non-invasive phenotype observed in Example 1 was in fact due to IQGAP1 depletion and not simply potential downregulation of IQGAP family members, we examined the mRNA levels of IQGAP2 in response to IQGAP1 depletion. For both IQGAP1 and IQGAP2, the knockdowns were specific and we did not observe compensation by the non-targeted family member (FIG. 6B). This result is somewhat expected given the previous published work by White et al. (2010), where they showed divergent functions for IQGAP1 and IQGAP2 in hepatocellular carcinoma despite their shared sequence similarity (FIG. 6A) (White, C. D., et al. IQGAP1 and IQGAP2 are reciprocally altered in hepatocellular carcinoma. BMC Gestroenterol 10, 125-135 (2010)).

Figure 7:
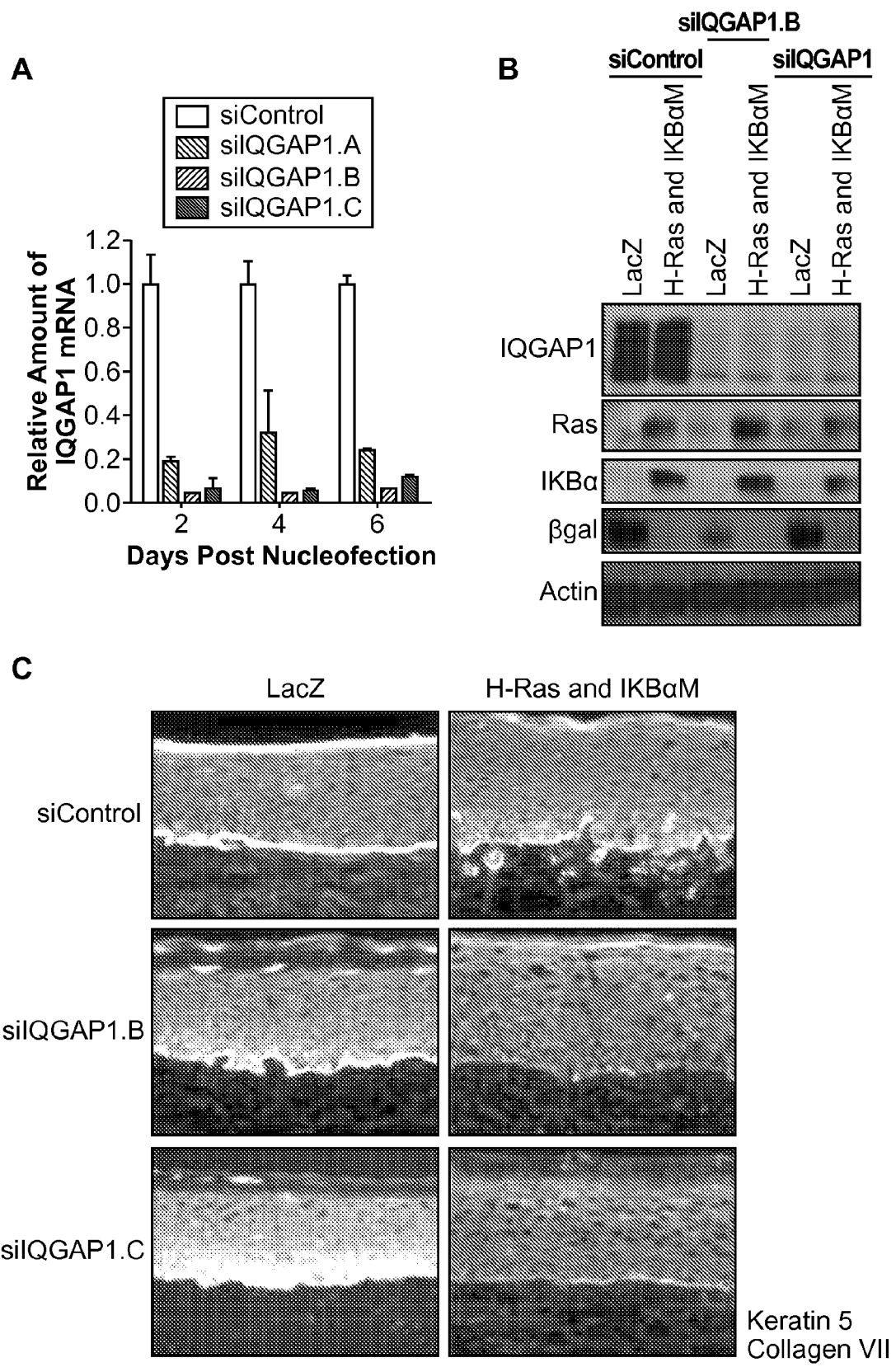
FIG. 7 depicts confirmation of IQGAP1 effects on transformed and non-transformed tissue with two additional siRNAs targeting 3' UTR of IQGAP1. (A) qRT-PCR validating knockdown of IQGAP1 two, four, and six days post-nucleofection with siRNAs corresponding to non-functional control, coding sequence of IQGAP1 (IQGAP1.A) and 3' UTR of IQGAP1 (IQGAP1.B, and IQGAP1.C). (B) Immunoblots of primary keratinocyte extracts comparing IQGAP1 levels in response to treatment with LacZ or H-RAS$^{G12V}$/IKBα. Cell lysates were also probed with RAS, IκBα, and βgal to show levels of LacZ, H-RAS, IKBα, and actin to verify equal loading. (C) Immunofluorescence staining of the epithelial marker keratin 5 (orange) and the basement membrane zone (BMZ) protein type-VII collagen (green) of LacZ (left) or H-RAS$^{G12V}$/IκBα (right) organotypic human tissue expressing siRNAs as in (A). All stains and immunoblots are representative images for at least 3 independent experiments.

As highlighted in a review by Ferrell (2000), the stoichiometry of scaffold proteins is key to signaling dynamics (Ferrell, J. E. What do scaffold proteins really do? Sci STKE 2000, PE1 (2000)). Depletion of a scaffold results in diminished signaling through a cascade just as overexpression of a scaffold can result in monomeric binding and reduced signaling (Ferrell, J. E. What do scaffold proteins really do? Sci STKE 2000, PE1 (2000)). Functionally rescuing IQGAP1 depleted cells by way of an overexpression construct is technically difficult since expression levels would need to be fine-tuned to endogenous levels to avoid potential dominant negative effects. Therefore to account for potential siRNA off-target effects, we tested multiple siRNAs to IQGAP1 to confirm the non-invasive phenotype was mediated by knockdown of IQGAP1. These siRNAs targeted sequences in the 3' UTR of IQGAP1 (siIQGAP1.B and siIQGAP1.C) and mediated more durable knockdown than those targeting sequences in the coding region (siIQGAP1.A) (FIG. 7A). Regardless of any of these modest differences observed between these siRNAs, protein levels of H-RAS, IκBαM, LacZ, and IQGAP1 confirm that cells had comparable levels of neoplastic mediators (FIG. 7B). More importantly, in tissue regenerated with any of these siRNAs, we saw no invasion in H-RAS/IκBαM expressing tissue and phenotypically normal tissue in LacZ expressing tissue (FIG. 7C). Thus, use of siRNAs to transiently remove IQGAP1 confirms our previous assertion that this scaffold protein has an essential role in epithelial neoplastic invasion.

Figure 8:
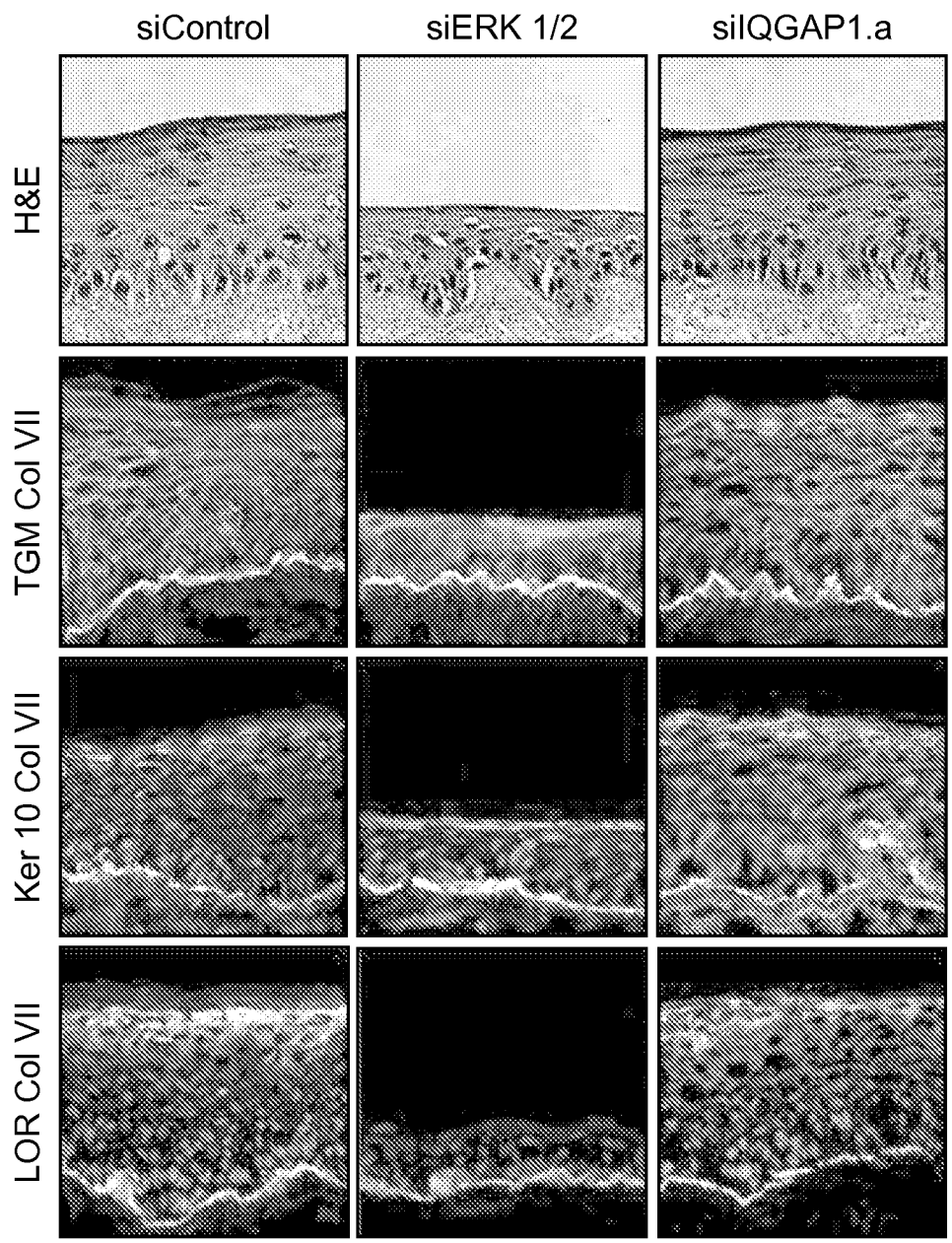
FIG. 8 illustrates that IQGAP1 knockdown does not affect normal tissue differentiation, stratification, or proliferation. (A) Immunohistochemistry staining for early and late, differentiation markers transgluaminase (TGM), keratin 10 (Ker10), and loricrin (LOR, orange) and the basement membrane zone (BMZ) protein type-VII collagen (green) in normal human organotypic tissue expressing siRNAs corresponding to a non-functional control, ERK1 and ERK2, or IQGAP1 sequences. (B) Ki67 (orange) and the basement membrane zone (BMZ) protein type-VII collagen (green) in normal human organotypic tissue expressing LacZ and siRNAs corresponding to a non-functional control and IQGAP1 sequences. (C) Quantification of Ki67-positive cells as in (B), ±SD. All stains are representative images for at least 3 independent experiments.

Since IQGAP1 recapitulates the invasion blocking phenotype of ERK1/2 depletion in neoplastic tissue, we also investigated the consequences of IQGAP1 depletion on normal tissue. LacZ-expressing control tissue as well as ERK1/2 and IQGAP1 knockdown tissue were harvested and stained for markers of normal skin differentiation by immunofluorescence (FIG. 8B-E). While ERK1/2 tissue was characteristically hypoplastic and revealed diminished levels of differentiation markers such as Keratin 10, Transglutaminase, and Loricrin, IQGAP1 depleted tissue was phenotypically normal. Stratification and layer formation as assessed by histology were also indistinguishable from control tissue (FIG. 8A). Staining with the proliferation marker Ki67 also revealed no significant differences in proliferation between IQGAP1 depleted and healthy control tissue (FIGS. 8B and 8C). Collectively, these data demonstrate that IQGAP1 knockdown inhibits neoplastic invasion without effecting normal tissue homeostasis in our human tissue model system.

Figure 9:
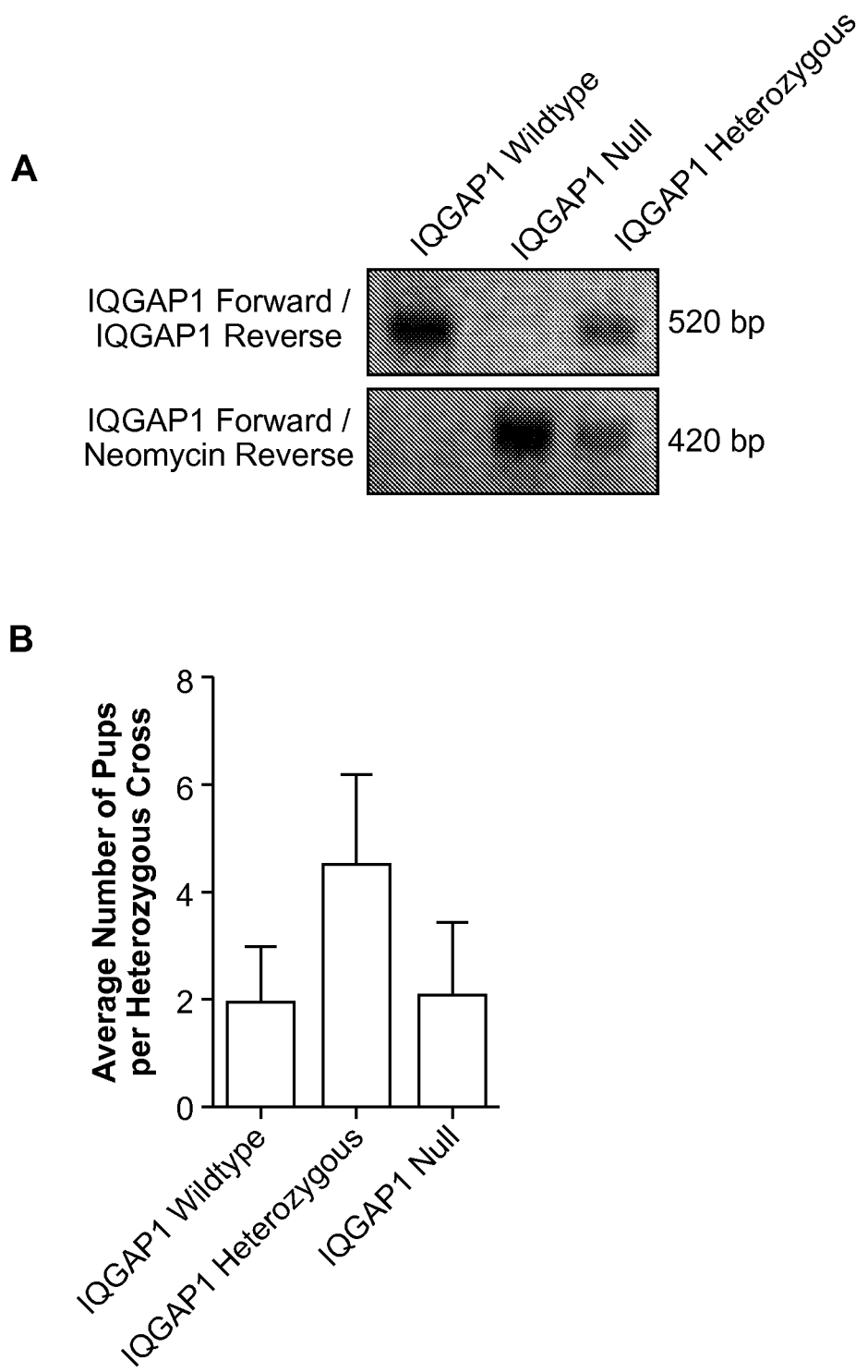
FIG. 9 illustrates that IQGAP1 knockout mice are born at expected Mendelian ratios and exhibit no differences in aged skin as compared to wildtype. (A) PCR validating presence of IQGAP1 allele with IQGAP1 forward and reverse primers (top) and neomycin cassette with IQGAP1 forward and neomycin reverse primers (bottom). (B) Quantification of genotypes of pups from twenty heterozygous crosses. (C) Gender-matched, litter-matched wildtype and IQGAP1 null skin from six-month and eighteen-month old mice.
Figure 9:
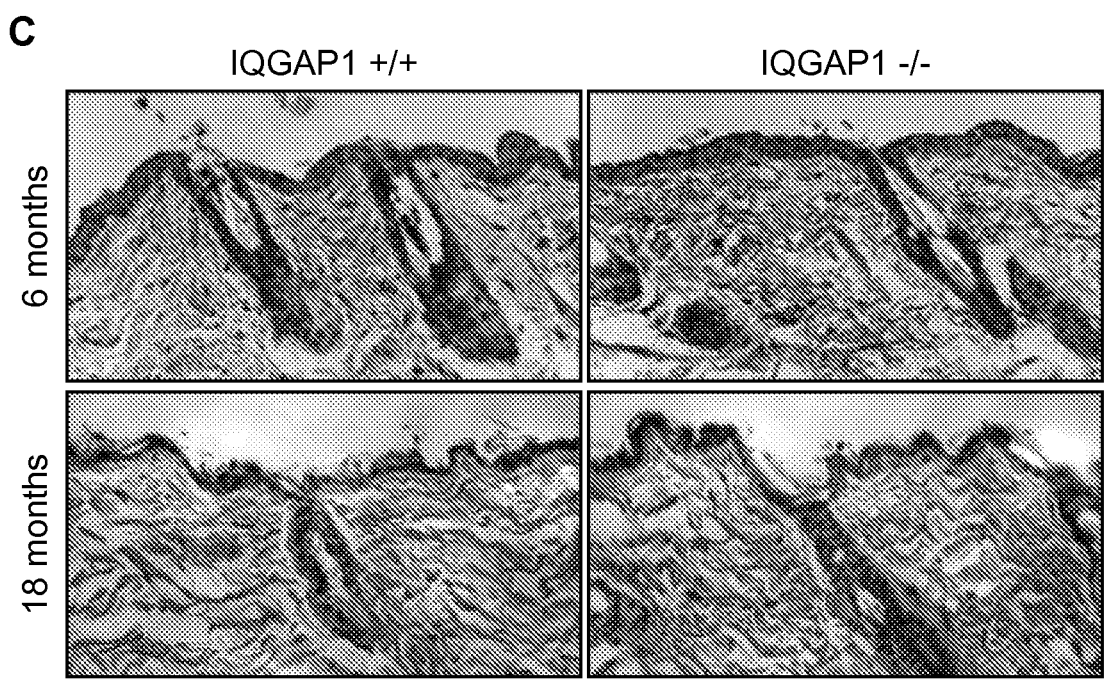

IQGAP1 knockout mice develop and heal wounds normally. IQGAP1 heterozygous animals in a mixed C57BU6 and 129 background were used to build a colony of IQGAP1 wildtype, heterozygous, and knockout mice. In order to verify genotypes, DNA was isolated from tail clippings and analyzed by PCR for an IQGAP1 allele and/or a neomycin cassette (FIG. 9A). As previously reported, we confirmed reported Mendelian ratios for all genotypes, illustrating that IQGAP1 knockout does not affect normal adult breeding or embryonic development (FIG. 9B) (Li, S., et al. Gastric hyperplasia in mice lacking the putative Cdc42 effector IQGAP1. Mol Cell Biol 20, 697-701 (2000)). Since our lab was specifically interested in epithelial tumorigenesis, we analyzed the dorsal skin of 6-month and 18-month old IQGAP1 wild-type and null animals. These time points were selected for analysis because we believed that any pathological effects to skin homeostasis would be apparent. No differences in stratification or morphology were observed upon comparing skin from the two genotypes, consistent with the findings of Li et al. who extensively characterized these mice and only identified late-stage gastric hyperplasia (FIG. 9C) (Li, S., et al. Gastric hyperplasia in mice lacking the putative Cdc42 effector IQGAP1. Mol Cell Biol 20, 697-701 (2000)).

Our human tissue organotypic system models RAS-driven epithelial neoplastic invasion as seen in squamous cell carcinoma (SCC) (Khavari, P. A. Modeling cancer in human skin tissue. Nat Rev Cancer 6, 270-280 (2006); Ridky, T. W., et al. Invasive three-dimensional organotypic neoplasia from multiple normal human epithelia. Nat Med 16, 1450-1456 (2010); Dajee, M., et al. NF-kappaB blockade and oncogenic RAS trigger invasive human epidermal neoplasia. Nature 421, 639-643 (2003); Tartutani, M., et al. Inducible activation of RAS and RAF in adult epidermis. Cancer Res. 63, 319-323 (2003)). Since SCCs are often associated with sites of chronic injury and there was such a robust phenotype to SCCs following IQGAP1 knockdown, we next tested whether IQGAP1 loss would adversely affect wound healing (Edwards, M. J., et al. Squamous cell carcinoma arising in previously burned of irradiated skin. Arch Surg 124, 115-117 (1989)) in the IQGAP1 knockout animals. Six to eight week old IQGAP1 wildtype, heterozygous, and null animals were subjected to through-and-through 6 mm punch biopsies, and wound area was assessed every three days (FIG. 10A). Wound closure was plotted as a percent of total initial wound area (FIG. 10B). Total wound closure occurred within twelve days for all of the IQGAP1 genotypes tested, indicating that IQGAP1 depletion did not affect wound healing response (FIG. 10). Together these data highlight that IQGAP1 knockout mice are viable and fertile and do not exhibit defects in normal epithelial tissue or wound healing.

Figure 11:
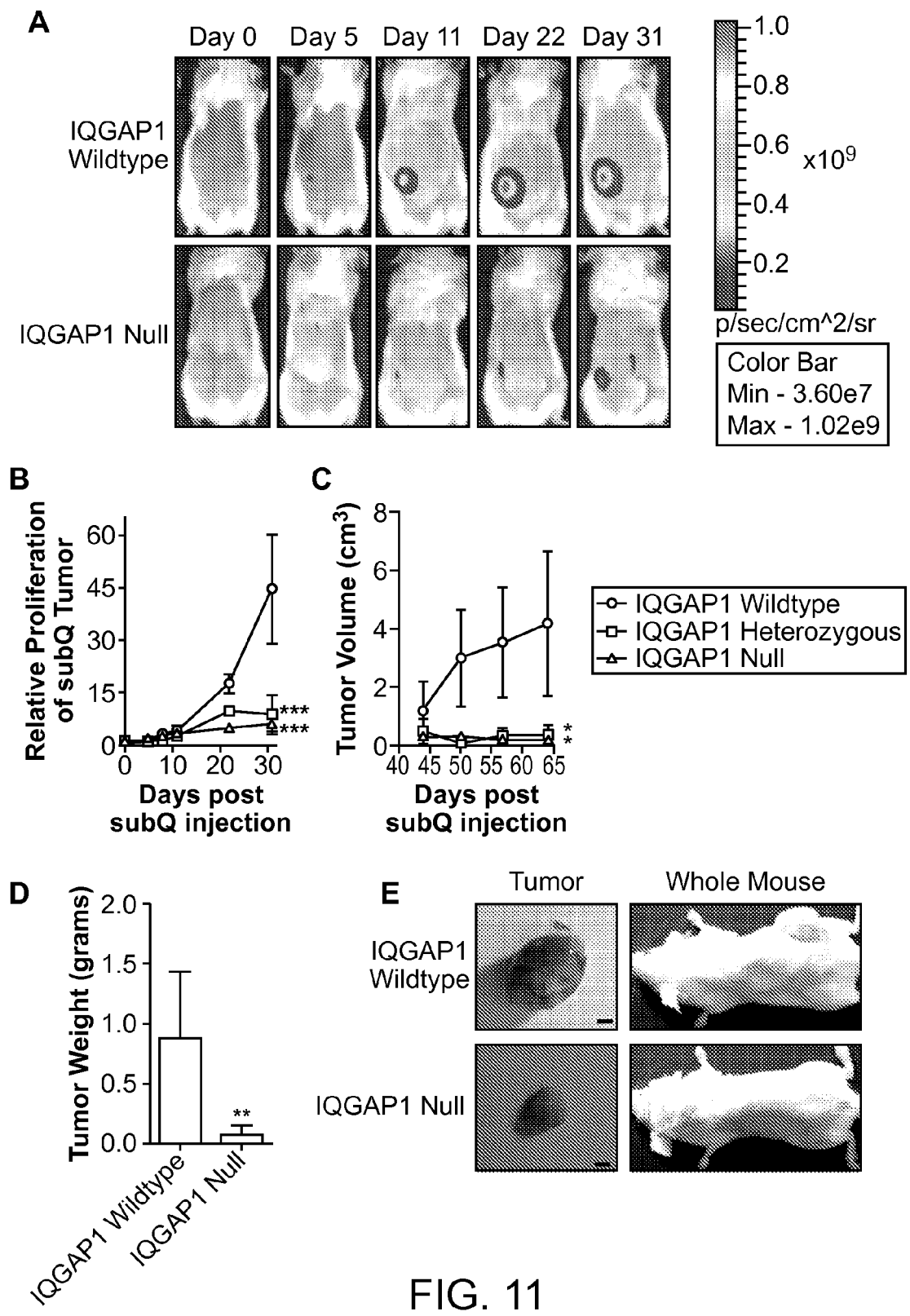
FIG. 11 illustrates diminished tumorigenesis in cells from IQGAP1 knockout mice following transformation with H-RAS$^{G12V}$/IκBαM. (A) Representative bioluminescence images of H-RAS$^{G12V}$/IκBαM-infected IQGAP1 wildtype (top) and null (bottom) murine epithelial cells over time as indicated. (B) Tumor xenograft growth after injection of cells in (A) as represented by mean average radiance (photons per second per cm2 per steridian). (C) Tumor growth after injection of cells in (A) as represented by tumor volume. (D) Tumor weight of cells in (A). (E) Clinical appearance of excised tumors (left) and whole mouse (right) following injection of cells in (A). Black scale bar=5 mm. n=4 mice/group, ±SD. p-values as follows: * ≤0.1,  ≤0.06, * ≤0.01.

Diminished tumorigenesis in IQGAP1 knockout mice. Since we have shown that IQGAP1 plays a role in mediating neoplastic migration without affecting migratory responses associated with wound healing, we next investigated the potential for IQGAP1 to inhibit in vivo tumor growth. Previous studies suggested that IQGAP1 knockout mice did not differ in spontaneous tumor growth as compared to wildtype animals (Li, S., et al. Gastric hyperplasia in mice lacking the putative Cdc42 effector IQGAP1. Mol Cell Biol 20, 697-701 (2000)). We therefore explored how these mice differed in tumor formation following oncogene and chemical driven tumorigenesis. We isolated primary murine epithelial cells from neonates, transformed them with retroviruses carrying H-RAS/IκBαM and the firefly luciferase gene, and subsequently injected these cells into the subcutaneous space of SCID mice. We hypothesized that if IQGAP1 is essential for malignant transformation, then loss of IQGAP1 might prevent tumor growth. We assayed tumor growth by non-invasive bioluminescence imaging of luciferase-expressing tumors, until tumor volume exceeded the quantifiable imaging parameters at which time tumors volume was assessed using calipers (FIG. 11A) (Lim, E., et al. In vivo bioluminescent imaging of mammary tumors using IVIS spectrum. J V is Exp 26, 1-2 (2009)). In the first four weeks post injection, mice injected with IQGAP1 wildtype cells developed significantly larger tumors than those derived from IQGAP1 null cells (FIG. 11B). IQGAP1 wildtype tumors continued to grow for the next five weeks, whereas IQGAP1 null and heterozygous tumors did not increase in size during this time (FIG. 11O).

The final weight of excised IQGAP1 null tumors was significantly smaller than IQGAP1 wildtype tumors, which supported the macroscopic differences we observed (FIGS. 11D and 11E). Interestingly, tumors derived from transformed IQGAP1 heterozygous cells more closely resembled those from IQGAP1 null mice. This data suggests that two functional alleles of IQGAP1 are required for RAS-driven tumor growth.

Figure 12:
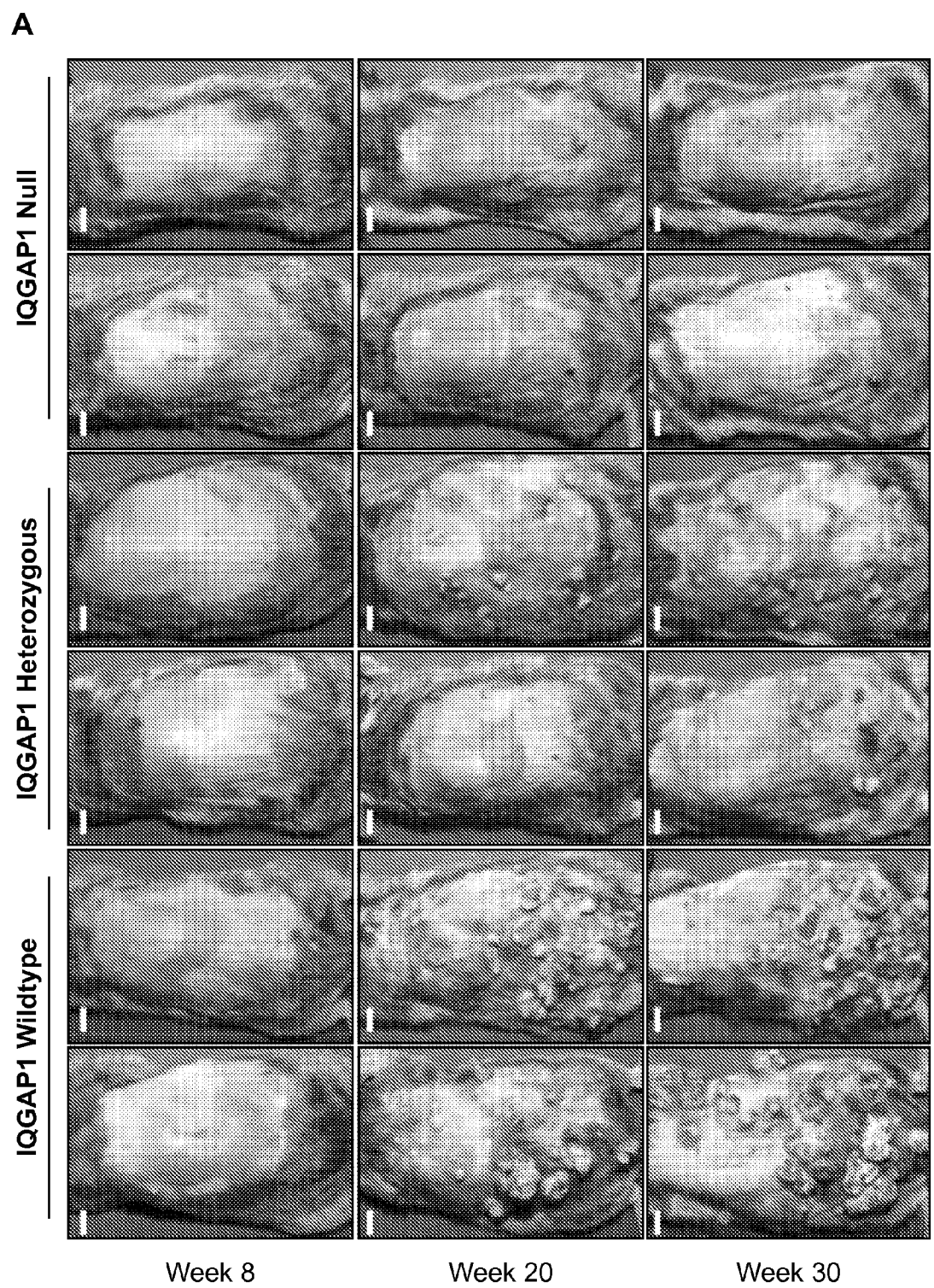
FIG. 12 illustrates diminished tumorigenesis in IQGAP1 knockout mice following DMBA/TPA treatment. (A) Clinical appearance of papillomas in IQGAP1 wildtype (left), heterozygous (middle), and null (right) animals over time. White scale bar=5 mm. (B) Quantification of papilloma formation over time as in (A). Color bars denote tumor volume: Blue=10-50 mm$^3$, Green=50-100 mm$^3$, Yellow=100-500 mm$^3$, Orange=500-1000 mm$^3$, and Red>1000 mm$^3$. Papillomas smaller than 10 mm$^3$ are abortive papillomas and not shown here. (C) Papilloma-free survival curve. (D) Quantification of tumor burden at week 30. n=7 mice per group, ±SD.

To further confirm the role of IQGAP1 in RAS-driven neoplasia, we elected to explore tumor formation induced by two-step chemical carcinogenesis. In this classical method, initial topical application of 7,12-dimethylbenz(a)anthracene (DMBA) causes mutations in H-RAS codon 61. Bi-weekly treatments with the tumor promoter 12-O-tetradecanoylphorbol-13-acetate (TPA) cause chronic hyperplasia and inflammation as well as selective clonal expansion into benign papillomas (Toftgard, R., et al. Proto-oncogene expression during two-stage carcinogenesis in mouse skin. Carcinogenesis 6, 655-657 (1985)). Eight to ten week old IQGAP1 wildtype, heterozygous, and null animals were treated with DMBA and subsequent bi-weekly treatments with TPA for thirty weeks. Dramatic macroscopic differences in these animals were very apparent (FIG. 12A). IQGAP1 wildtype animals had many more and much larger papillomas than IQGAP1 null animals (FIG. 12B). In fact after nine weeks of treatment, all of the IQGAP1 wildtype animals had at least one papilloma with a volume greater than 10 mm3 (FIG. 12C). On the other hand, after thirty weeks of treatment almost 50% of IQGAP1 null animals remained papilloma-free (FIG. 12C). Additionally at the end of the experiment, the mean tumor burden of IQGAP1 wildtype animals was five-fold more than that of IQGAP1 null animals (FIG. 12D). Interestingly, IQGAP1 heterozygous animals displayed an intermediate phenotype, suggesting a correlation between IQGAP1 gene dosage and tumor susceptibility (FIGS. 12A and 12B).

Figure 13:
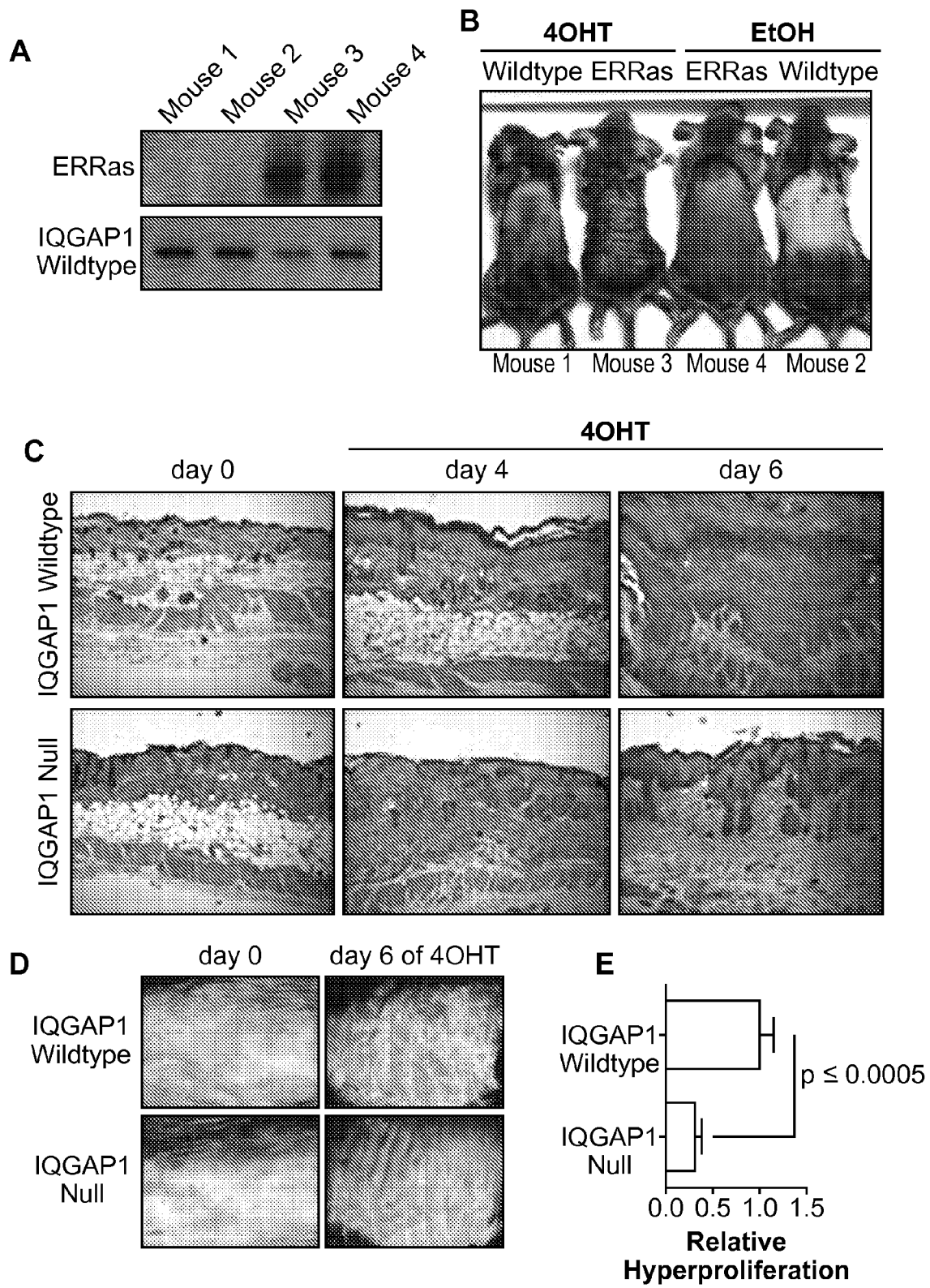
FIG. 13 illustrates diminished hyperplasia in IQGAP1 knockout mice following exposure to acute oncogenic H-RAS. (A) PCR validating presence of K14-ER:H-RAS transgene with forward and reverse primers (top) and IQGAP1 allele with IQGAP1 forward and reverse primers (bottom). (B) Clinical appearance of treated skin on mice in (A) following seven days of 4OHT or EtOH. (C) Histology of skin from K14-ER:H-RAS, IQGAP1 wildtype and K14-ER:H-RAS, IQGAP1 null animals treated with 4OHT as indicated. (D) Clinical appearance of treated skin of mice in (C). (E) Quantification of hyperplasia in (C). n=4 mice per group.

To examine the effects of IQGAP1 in response to acute oncogenic RAS activation, we made use of a previously generated K14-ER:H-RASG12V mouse strain (Tarutani, M., et al. Inducible activation of RAS and RAF in adult epidermis. Cancer Red 63, 319-323 (2003)). These animals express a 4-hydroxytamoxifen (4OHT)-regulated H-RASG12V fusion transgene under a keratin (K14) promoter that drives expression of RAS in basal layers of the skin (ibid). Activation of RAS via application of 4OHT directly onto the skin results in massive hyperplasia (ibid). To assess any potential leakiness in our 4OHT-responsive mutant ER:H-RASG12V, IQGAP1 wildtype and IQGAP1 wildtype K14-ER:H-RASG12V were treated with EtOH (vehicle) or 4OHT daily for one week (FIGS. 13A and 13B). Hyperplastic skin was only observed in animals with K14-ER:H-RASG12V and treated with 4OHT. Animals expressing K14-ER:H-RASG12V and treated with EtOH resembled wildtype animals treated with EtOH. Moreover, wildtype animals treated with 4OHT did not develop any adverse effects (FIG. 13B). Having confirmed the effectiveness of this inducible transgene, we crossed IQGAP1 null animals with K14-ER:H-RASG12V heterozygous animals to yield IQGAP1 heterozygous, K14-ER:H-RASG12V heterozygous animals.

We subsequently crossed these lines with additional IQGAP1 heterozygotes to yield IQGAP1 wildtype and null, K14-ER:H-RASG12V littermates. Since the PCR reaction used to detect the ER:H-RASG12V transgene cannot discriminate between one copy and two copies of the transgene, care was taken to never cross two transgene positive animals to one another. Six to eight week old IQGAP1 wildtype and null, K14-ER:H-RASG12V were split into 3 groups and never treated, treated 4 days, or treated 6 days with 4OHT. Treated skin was harvested from these animals and histology showed the massive hyperplasia in response to acute oncogenic RAS in IQGAP1 wildtype animals (FIG. 13C). IQGAP1 null animals had some hyperplasia, but significantly less than their wildtype counterparts (FIGS. 13C and 13E). Moreover, the clinical appearance of IQGAP1 wildtype animals reveals a much more severe blistering and hyperkeratosis phenotype than paired littermates (FIG. 13D). Collectively, these data suggest a model wherein oncogenic RAS-mediated signaling requires IQGAP1 for tumorigenic initiation and growth.

IQGAP1 in Squamous Cell Carcinoma. As previously reported increased IQGAP1 expression has been observed in a number of different cancers, but to the best of our knowledge no one has yet explored IQGAP1 in human skin cancer. In the first half of this work, we explored the effects of IQGAP1 on RAS-mediated epithelial cell invasion in what can be described as different models of oncogene-induced and chemical-induced squamous cell carcinoma. To evaluate expression of IQGAP1 in spontaneous SCCs, we compared tissue from normal human epidermis and invasive SCCs. While IQGAP1 is expressed in all epidermal tissue tested, it is much more strongly expressed in SCCs (FIGS. 14A and C). Furthermore, IQGAP1 is most strongly expressed in early stage SCCs suggesting increases in IQGAP1 expression may be an initiating event in cellular transformation and SCC development (FIG. 14B). These data corroborate the results we see in our human tissue model system and strongly implicates the importance of IQGAP1 in progression from normal tissue to cancerous tissue.

Figure 15:
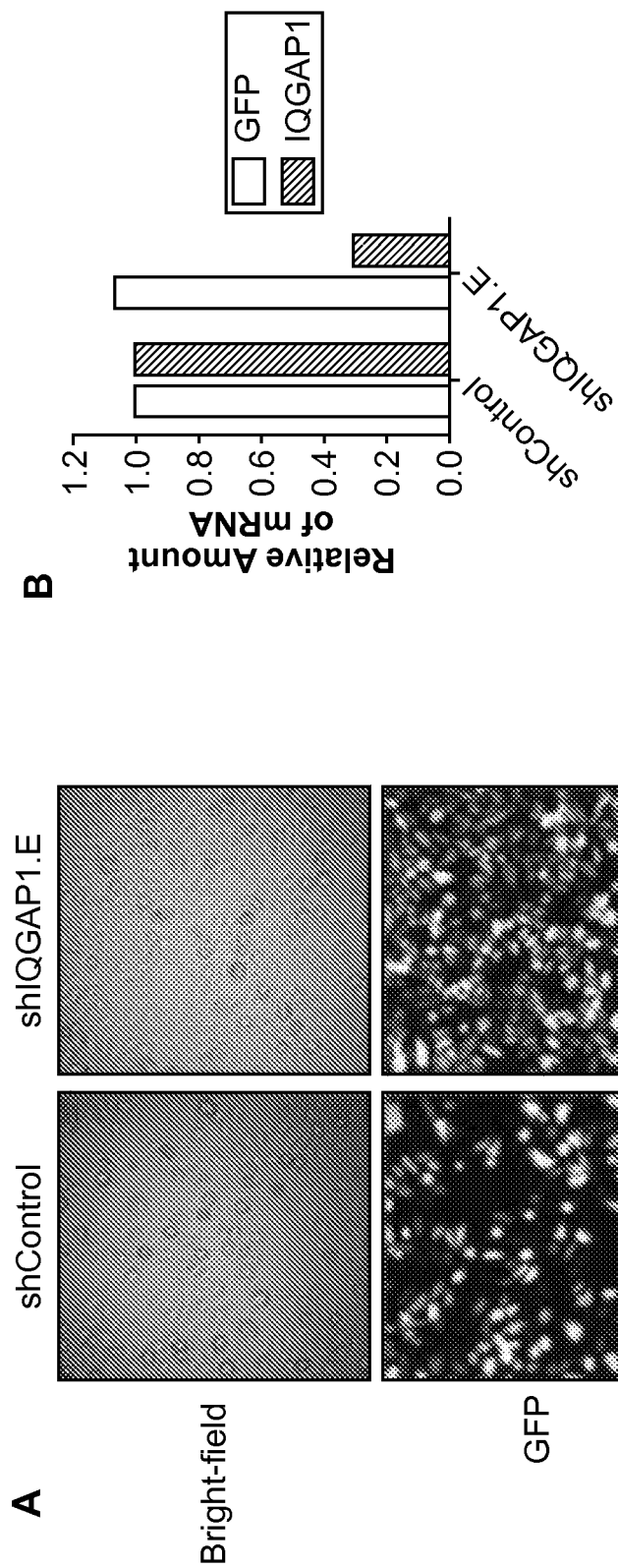
FIG. 15 depicts hairpins targeting IQGAP1 mediate long-term knockdown of IQGAP1 and confirm inhibition of invasion. (A) Bright-field and GFP fluorescence of scrambled control and IQGAP1 targeting hairpins. (B) qRT-PCR validating knockdown of IQGAP1 and equal GFP levels of shRNAs as in (A). (C) Confocal stack images showing the expression of keratin (in red), BMZ protein type-VII collagen (in green), and nuclei of keratinocytes and fibroblasts (in blue) of RAS-driven organotypic human epidermal neoplasia, treated with shRNAs targeting scrambled control or IQGAP1. Images are X-Y plane (top) and Z-X plane (middle); note reversion of invasive destruction of the BMZ by IQGAP1 tissue depletion. Immunohistochemistry staining for IQGAP1 (bottom). Black dashed line denotes BMZ separation of epidermis and underlying dermis. (D) qRT-PCR validating knockdown of IQGAP1 of shRNAs in (C). (E) Lysates prepared from primary human keratinocytes infected ten-days before with IQGAP1 and scrambled control hairpins were probed for levels of IQGAP1 and actin as a loading control. All qPCR, stains, and immunoblots are representative images for at least 3 independent experiments, except (B) which is data from one experiment.

Understanding that increased IQGAP1 expression could be a causative event in other tumor types or simply a non-related effect of tumorigenesis, we evaluated how IQGAP1 knockdown affects other tumors. SiRNA-mediated knockdown was very efficient for short-term studies in our model system, but in order to expand our studies we also needed to expand our knockdown. To this end, we identified three short hairpin RNAs (shRNAs) that mediate puromycin-selectable long-term knockdown of IQGAP1. Additionally, these hairpin-expressing vectors also carry the gene encoding the green fluorescent protein (GFP), which allowed us to visually inspect our cells for presence of shIQGAP1 (FIGS. 15A and 15B). These hairpins also allowed us the opportunity to revise our tumor initiating protocol. Rather than continue use of the H-RAS/IκBαM and LacZ retroviruses, we began to use CDK4 and ER:H-RAS lentiviruses. Co-expression of CDK4, like IκBα, mediates escape from RAS-induced senescence and induces invasive neoplasia in our human tissue model system (Ridky, T. W., et al. Invasive three-dimensional organotypic neoplasia from multiple normal human epithelia. Nat Med 16, 1450-1456 (2010); Lazarov, M., et al. CDK4 coexpression with RAS generates malignant human epidermal tumorigenesis. Nat Med 8, 1105-1114 (2002); Lazarov, M., et al. Escaping G1 restraints on neoplasia—Cdk4 regulation by RAS and NF-kappa B. Cell Cycle 2, 79-80 (2003)). Moreover, this system employs a 4OHT-responsive H-RAS mutant, which allows for precise control over oncogenic RAS activation (Ridky, T. W., et al. Invasive three-dimensional organotypic neoplasia from multiple normal human epithelia. Nat Med 16, 1450-1456 (2010); Reuter, J. A., and Khavari, P. A. Use of conditionally active RAS fusion proteins to study epidermal growth, differentiation, and neoplasia. Methods Enzymol 407, 691-702 (2006)). Thus, we can set up our regenerated tissue with longer-term knockdown via the hairpins targeting IQGAP1 and allow the keratinocytes to begin proliferation and stratification prior to initiating expression of oncogenic RAS, which more accurately mimics the RAS-signaling observed in spontaneously occurring neoplastic human tissue (Ridky, T. W., et al. Invasive three-dimensional organotypic neoplasia from multiple normal human epithelia. Nat Med 16, 1450-1456 (2010); Reuter, J. A., and Khavari, P. A. Use of conditionally active RAS fusion proteins to study epidermal growth, differentiation, and neoplasia. Methods Enzymol 407, 691-702 (2006)). Daily treatment of organotypic tissue with vehicle (EtOH) does not activate RAS and the epidermis remains adherent to the BMZ (FIG. 15C). Daily treatment with 4OHT, however, resulted in neoplastic invasion and characteristic degradation of the BMZ (FIG. 15C). Hairpins targeting IQGAP1 recapitulate the inhibition of neoplastic invasion observed using siRNA to knockdown IQGAP1 (FIG. 15C). Importantly, the shRNAi-mediated stable knockdown was comparable to that of siRNAs (FIGS. 15D and 15E).

Figure 16:
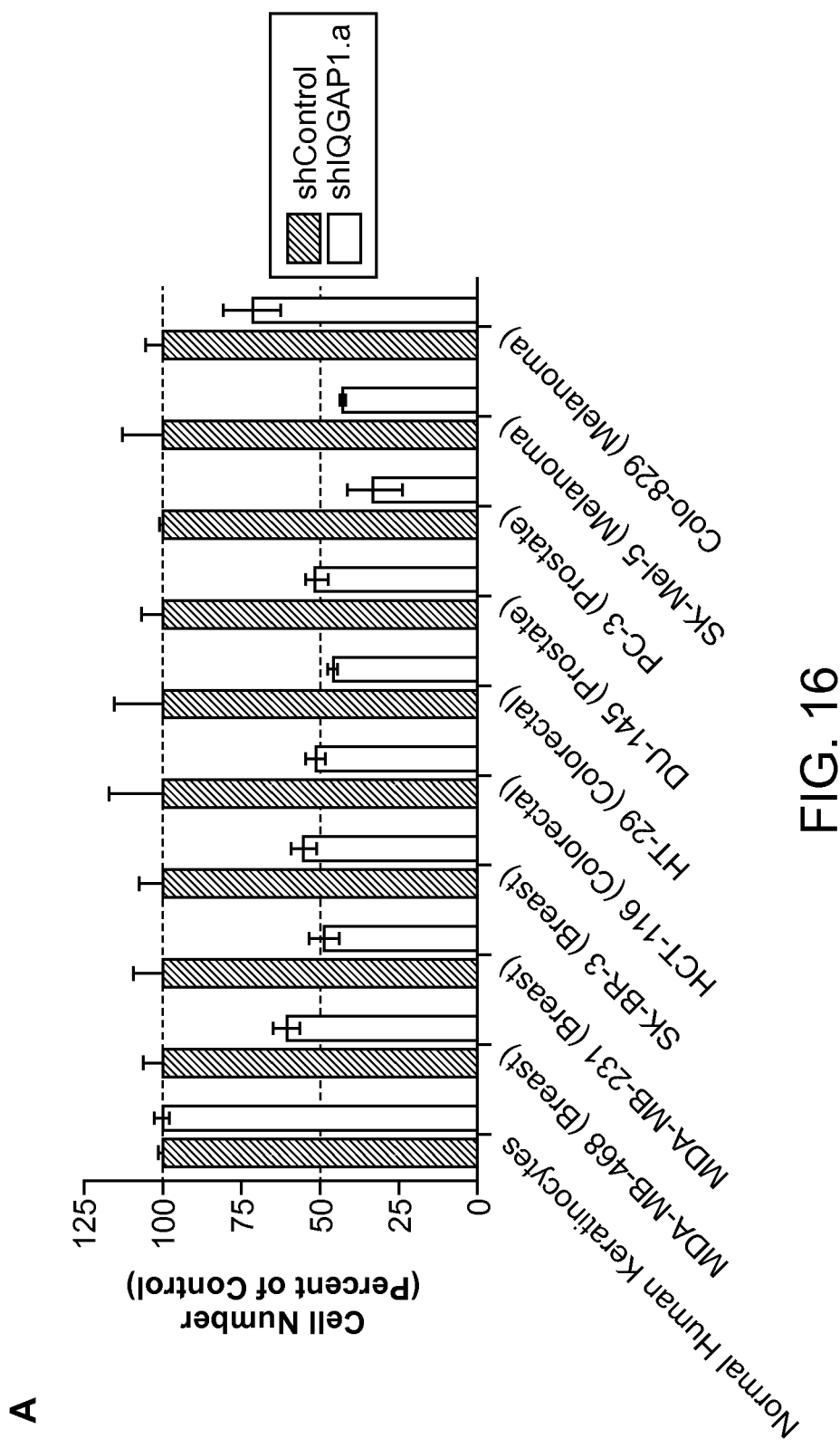
FIG. 16 illustrates diminished proliferation of RAS-driven cancer following IQGAP1 knockdown. (A) Proliferation assays of primary human keratinocytes, breast cancer cell lines (EGFR-overexpressing MDA-MB-468, KRAS-mutant MDA-MB-231, and HER2-overexpressing SK-BR-3), colorectal cancer cell lines (KRAS-mutant HCT-116 and BRAF-mutant HT-29) prostate cancer cell lines (EGFR-overexpressing PC-3 and DU-145), and melanoma skin cancer cell lines (BRAF-mutant SK-MeI-5 and Colo-829) following treatment with shRNAs targeting scrambled control (black) or IQGAP1 (gray). (B) qRT-PCR validating shRNA-mediated knockdown of IQGAP1 of cells in (A). Breast cancer cell line 1: MDA-MB-468; 2: MDA-MB-231; 3: SK-BR-3. Colorectal cancer cell line 1: HCT-116; 2: HT-29. Prostate cancer cell line 1: DU-145; 2: PC-3. Melanoma cancer cell line 1: SK-MeI-5; 2: Colo-829. All values for proliferation assays and qPCR are mean of 3 samples±SD, respectively.
Figure 16:
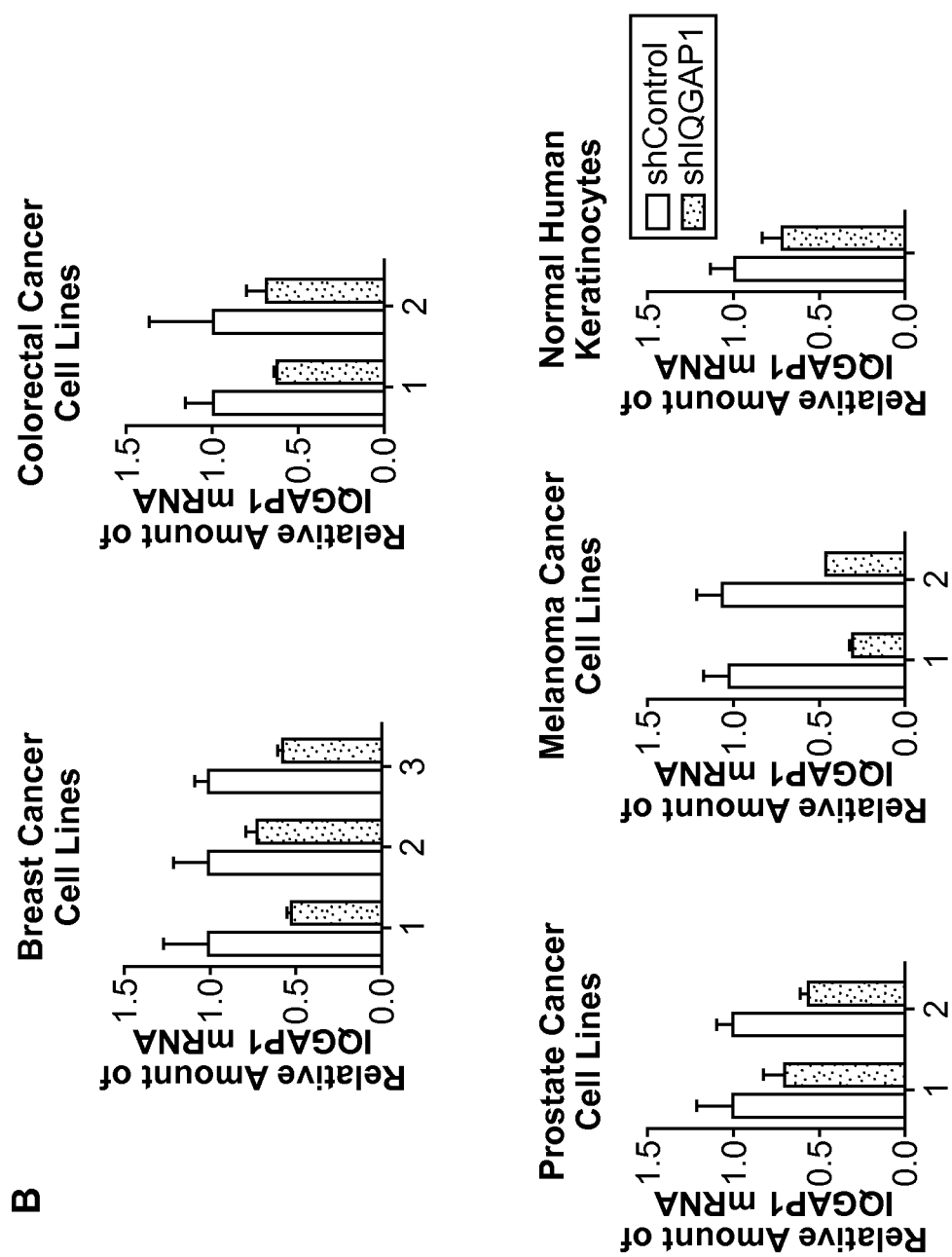

IQGAP1 in Breast, Colorectal, Prostate, and Melanoma Cancers. In order to examine IQGAP1 function in other cancer types, we collected a variety of cancer cell lines. Knockdown of IQGAP1 with shRNAs in these cells consistently resulted in decreased proliferation. For example, in three independent breast cancer cell lines with three different mechanisms of pathological MAPK activation, we were able to routinely knockdown IQGAP1 to ~50% and at this level we saw a significant decrease in proliferation compared to control (FIGS. 16A and 16B). Additionally, we saw similar knockdown levels and proliferation defects in two colorectal cancer cell lines with KRAS and BRAF mutations, two EGFR-overexpressing prostate cancer cell lines, and two BRAF mutant melanoma cancer cell lines (FIGS. 16A and 16B). Interestingly, knocking down IQGAP1 to comparable levels in normal primary human keratinocytes did not have an appreciable effect on proliferation (FIGS. 16A and 16B). These effects following IQGAP1 depletion confirm our suspicion that IQGAP1 knockdown could be an effective therapeutic for a multitude of cancer tissue types without adversely effecting normal tissue homeostasis.

Figure 17:
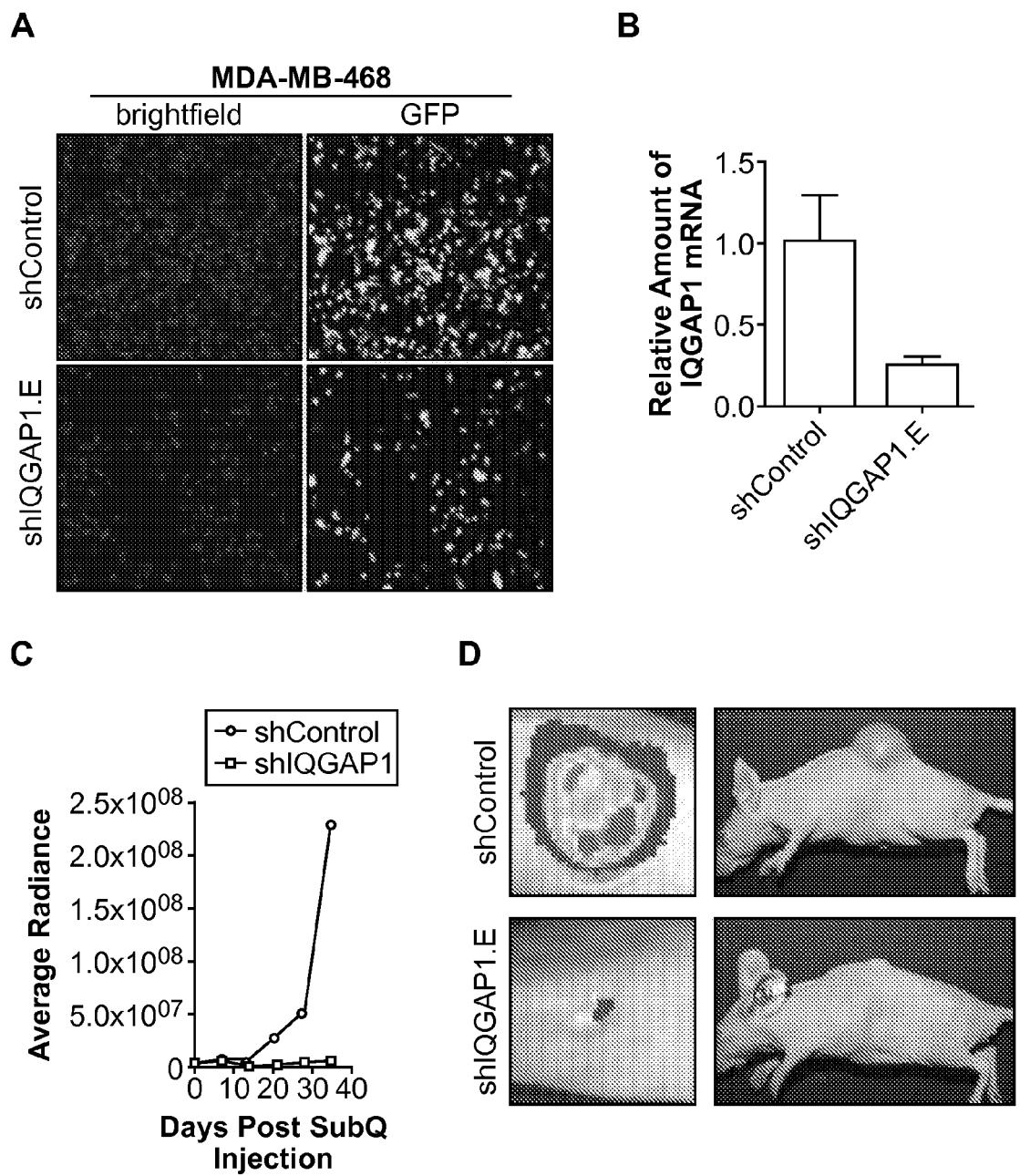
FIG. 17 illustrates diminished tumorigenesis in vivo of RAS-driven cancer following IQGAP1 knockdown. (A) Brightfield (left) and GFP fluorescence (right) of scrambled control (top) and IQGAP1 targeting hairpins (bottom) in MDA-MB-468 breast cancer cells (line #1 in FIG. 16). (B) qRT-PCR validating knockdown of IQGAP1 in (A). (C) Tumor xenograft growth after injection of cells in (A) as represented by mean average radiance (photons per second per cm2 per steridian). (D) Clinical appearance of tumors (right) and bioluminescence (left) of mice in (C) at week 35. n=2 mice/group, ±SD.

Next, we wanted to test the effects of IQGAP1 knockdown on in vivo tumor growth. MDA-MB-468 (breast cancer cell line 1) cells were verified to contain scrambled control or IQGAP1 hairpins by GFP expression (FIG. 17A). Efficient knockdown of IQGAP1 was also confirmed with qRT-PCR (FIG. 17B). One million luciferase positive breast cancer cells treated with scrambled control or IQGAP1 hairpins and luciferase were injected into the subcutaneous space of hairless SCID mice. Tumor formation was assayed by luciferase expression as measured in average radiance values. Control-treated MDA-MB-468 tumors grew rapidly, whereas tumors depleted for IQGAP1 failed to grow (FIGS. 17C and 17D). Together, these data confirm in vitro results that IQGAP1 is not only a tumor selective target in RAS-driven skin cancers, but also in RAS-driven cancer of multiple types. Furthermore, it highlights the importance of IQGAP1 expression in tumorigenesis suggesting IQGAP1 acts more like a driver of oncogenesis than a by-product since knockdown of IQGAP1 elicits such dramatic effects on tumors.

Non-Essential Role of IQGAP1 in Homeostasis. Having confirmed that IQGAP1 and IQGAP2 are not functionally redundant based on their expression levels as well as previous data from White et al. suggesting their differential functions (White, C. D., et al. IQGAP1 and IQGAP2 are reciprocally altered in hepatocellular carcinoma. BMC Gestroenterol 10, 125-135 (2010)) and that IQGAP1 alone was capable of inhibiting neoplastic invasion through the use of multiple siRNAs, we next analyzed homeostatic skin tissue for IQGAP1 loss-of-function phenotypes. We compared IQGAP1 knockdown tissue to the ERK1/2 knockdown tissue, which was characterized by defects in differentiation, proliferation, and stratification of normal skin. Interestingly, the grossly hypoproliferative epidermal tissue derived from ERK1/2 knockdown is reminiscent of the skin from MEK1/2 knockout mice (Scholl, F. A., et al. MEK1/2 MAPK kinases are essential for mammalian development, homeostasis, and RAF-induced hyperplasia. Cell 12, 615-629 (2007)). The skin of these mice also failed to terminally differentiate and thereby failed to develop a functional barrier and following significant transepidermal water loss animals died perinatally (ibid). In contrast, IQGAP1 siRNA-treated tissue was phenotypically similar to control-treated tissue which corroborates previous studies that reported mild homeostatic phenotypes in IQGAP1 knockout animals (Li, S., et al. Gastric hyperplasia in mice lacking the putative Cdc42 effector IQGAP1. Mol Cell Biol 20, 697-701 (2000); Balenci, L., et al. IQGAP1 regulates adult neural progenitors in vivo and vascular endothelial growth factor-triggered neural progenitor migration in vitro. J Neurosci 27, 4716-4724 (2007)). Together these data highlight that IQGAP1 is dispensable for normal tissue and a viable therapeutic target since knockout mice, as previously discussed, are viable, fertile, and have normal epidermal tissue and epidermal human tissue is able to stratify and differentiate normally.

To further assess the role of IQGAP1 in homeostasis, we next sought to explore the role of IQGAP1 in wound healing. Given the correlation between SCC formation and chronic wound sites, and previous studies that suggested that IQGAP1 ablation inhibits wound healing, we anticipated that IQGAP1 depletion would have resulted in less effective wound healing (Edwards, M. J., et al. Squamous cell carcinoma arising in previously burned of irradiated skin. Arch Surg 124, 115-117 (1989)). These previous studies, however, employed in vitro scratch assays, using siRNA-mediated knockdown of IQGAP1 in bronchial epithelial cells to model wound healing (Wang, Y., et al. IQGAP1 promotes cell proliferation and is involved in a phosphorylation-depended manner in wound closure of bronchial epithelial cells. Int J Mol Med 22, 79-87 (2008)). In contrast, we assessed the role of IQGAP1 in wound healing in a more rigorous in vivo context, and failed to observe any significant differences in the regeneration capacity of IQGAP1 knockout and control skin (Martin, P. Wound healing—aiming for perfect skin regeneration. Science 276, 75-81 (1997)). Together these data suggest that targeting IQGAP1 will not result in tissue catastrophe, changes in viability, or alterations to healing.

Essential Role of IQGAP1 in Tumorigenesis. Since we believe that IQGAP1 represents a nexus of RAS-oncogene addicted cancer signaling, we explored the effects of IQGAP1 loss on induced tumorigenesis. Initially, we explored classic mouse xenograft models. These experiments employed H-RAS-mediated transformation of primary murine epithelial cells isolated from IQGAP1 wildtype, heterozygous, and null mice. We followed tumor growth over time through non-invasive bioluminescence and caliper measurements. We observed significantly diminished tumorigenesis in tumors derived from IQGAP1 knockout animals. This highlights that in complete IQGAP1 knockout cells, tumorigenesis is diminished compared to control. We next employed a two-step chemical tumorigenesis model to complement our findings in the human tissue model system. This model has been widely used to study initiation, promotion, and progression of mouse skin tumors since the evolution of human squamous cell carcinoma has many similarities with mouse chemically induced squamous cell tumors (Toftgard, R., et al. Proto-oncogene expression during two-stage carcinogenesis in mouse skin. Carcinogenesis 6, 655-657 (1985); Scholl, F. A., et al. Selective role for MEK1 but not MEK2 in the induction of epidermal neoplasia. Cancer Res 69, 3772-3778 (2009)). Tumorigenesis was measured by several factors including time to first incidence of papilloma, total number of papillomas, and volume of papillomas. In each condition, IQGAP1 knockout animals had significantly diminished tumorigenesis as compared to their wildtype counterparts. While we did not observe progression into invasive SCCs in any of the papillomas, we believe this is due to the previously described mouse strain resistance to malignant conversion rather than the conditions of the experiment (Woodworth, C. D., et al. Strain-dependent differences in malignant conversion of mouse skin tumors is an inherent property of the epidermal keratinocyte. Carcinogenesis 25, 1771-1778 (2004)). Interestingly, IQGAP1 heterozygous animals displayed an intermediate phenotype, suggesting a correlation between IQGAP1 gene dosage and tumor susceptibility. This data also highlight that IQGAP1 depletion results in diminished tumorigenesis. Finally, we explored the tumorigenic response to acute oncogenic RAS as opposed to our previous studies following chronic oncogenic RAS exposure. In these sets of experiments, we employed the K14-ER:HR-RAS$^{G12V}$ mouse model that expresses an inducible form of H-RAS in the basal cells of the epidermis following exposure to 4-hydroxytamoxifen (4OHT) (Tartuani, M., et al. Inducible activation of RAS and RAF in adult epidermis. Cancer Res 63, 319-323 (2003)). IQGAP1 wildtype animals developed massive hyperplasia in response to H-RAS activation, whereas the skin from IQGAP1 null animals was significantly less hyperplastic. Taken together, our three independent in vivo methods to assess RAS-driven tumorigenesis present a compelling picture of the essential role of IQGAP1 in tumor initiation, formation, and progression. While some of these observations have been made in other in vitro models (Jadeski, L., et al. IQGAP1 stimulates proliferation and enhances tumorigenesis of human breast epithelial cells. J Biol Chem 283, 1008-1017 (2008)), we believe that our novel assessments in mouse models represent a high-quality dataset, complimenting and exceeding previous findings.

IQGAP1 is a tumor-selective target. In previous studies, IQGAP1 was found to be highly expressed in gastric, colorectal, and metastatic melanoma neoplasms (Sugimoto, N., et al. IQGAP1, a negative regulator of cell-cell adhesion, is upregulated by gene amplification at 15q26 in gastric cancer cell lines HSC39 and 40A. J. Hum. Genet. 46, 21-25 (2001); Nabeshima, K., et al. Immunohistochemical analysis of IQGAP1 expression in human colorectal carcinomas: its overexpression in carcinomas and association with invasive fronts. Cancer Lett. 176, 101-109 (2002); Clark, E. A., et al. Genomic analysis of metastasis reveals an essential role for RhoC. Nature 406, 532-535 (2000)). To our knowledge, however, no one has explored IQGAP1 expression in human squamous cell carcinoma. Employing two separate human tissue microarrays (TMA) consisting of a variety of different stage SCC and normal human epidermis samples, we saw an increase in IQGAP1 expression in tumor tissue compared to non-transformed tissue. Since IQGAP1 has recently been identified as a prognosticator of disease state in glioblastomas and thyroid cancers (Balenci, L., et al. IQGAP1 protein specifies amplifying cancer cells in Gluioblastoma Multiforme. Cancer Res 66, 9074-9082 (2006); Liu, Z., et al. IQGAP1 plays an important role in the invasiveness of thyroid cancer. Clin Cancer Res 16, 6009-6018 (2010); McDonald, K. L., et al. IQGAP1 and IGFBP2: valuable biomarkers for determining prognosis in glioma patients. J Neuropathol Exp Neurol 66, 405-417 (2007)), we explored whether IQGAP1 expression was correlated with disease state in spontaneous human SCCs. IQGAP1 was highly expressed in all grades of human SCC but most highly in initial grade I. This indicates that targeting IQGAP1 therapeutically would be effective in a number of tumors irrespective of tissue origin.

Since IQGAP1 knockdown mediates such potent anti-neoplastic effects in human and murine models of SCC and is observed to highly expressed in a number of cancer, we next investigated the effects of IQGAP1 loss on other RAS-driven cancers. Since the ERK/MAPK pathway is hyper-activated in 30% of all human cancers and RAS is such a potent oncogene, we hypothesized that IQGAP1 ablation would have effects on multiple RAS-driven tumor types (Chapman, M. S, and Miner, J. N. Novel mitogen-activated protein kinase kinase inhibitors. Expert Opin Investig Drugs 20, 209-220 (20111); Hersey, P., et al. Small molecules and targeted therapies in distant metastatic disease. Ann Oncol 20, vi35-40 (2009); Wickenden, J. A., et al. Colorectal cancer cells with BRAF (V600E) mutation are addicted to the ERK1/2 pathway for growth factor-independent survival and repression of BIM. Oncogene 27, 7150-7161 (2008); Weinstein, B. and Joe, A. Oncogene addiction. Cancer Res 68, 3077-3080 (2008).). We first identified three selectable hairpins to IQGAP1 that confer a non-invasive phenotype on oncogenic RAS transformed tissue in our organotypic system. Subsequently, we infected nine separate RAS-driven human cancer cell lines with these shRNA constructs. We observed significantly diminished proliferation in three breast cancer cell lines with three different mechanisms of pathological MAPK activation, two colorectal cancer cell lines with KRAS and BRAF mutations, two prostate cancer cell lines with EFGR overexpression, and two melanoma cancer cell lines with BRAF mutations. Interestingly, shIQGAP1 had no proliferation effects on non-transformed primary human keratinocytes underscoring yet again that IQGAP1 is not required for normal cell proliferation and tissue homeostasis. Furthermore, we confirmed these in vitro results through murine xenograft in vivo models and observed significantly smaller tumor formation in IQGAP1 knockdown cells compared to control. Collectively, these data confirm that IQGAP1 is a tumor selective target. IQGAP1 loss does not adversely affect homeostasis or wound healing. IQGAP1 expression is increased in variety of human cancers and depleting IQGAP1 levels results in diminished tumor formation, proliferation, and invasion. Therefore, we believe that IQGAP1 represent a therapeutic target not only for a few cancer types, but also for the treatment of all RAS-driven human cancers and once targeted will not adversely effect normal tissue.

These data also strongly suggest the role of dosage dependence in IQGAP1 pro-tumor signaling. Following DMBA/TPA treatment, IQGAP1 heterozygotes had an intermediate phenotype with slow growing papillomas similar to IQGAP1 knockouts, but a papilloma burden more similar to IQGAP1 wildtype. Whereas, tumors derived from primary murine cells transformed with oncogenic Ras expressing only one allele of IQGAP1 failed to increase substantially in size. Finally, shRNA constructs targeting IQGAP1 mediated a sustained knockdown of about 50% in various cancer cell lines resulting in significantly diminished tumor growth. Collectively, this data suggest that one allele of IQGAP1 is enough to initiate papilloma formation, but perhaps not enough to sustain Ras-driven tumor growth and that therapeutics targeting IQGAP1 might not need to inactivate 100% of IQGAP1 to mediate an effect or perhaps that there is a specific IQGAP1 signaling interaction inhibited by loss of 50% of IQGAP1.

Example 3

Results

Figure 5:
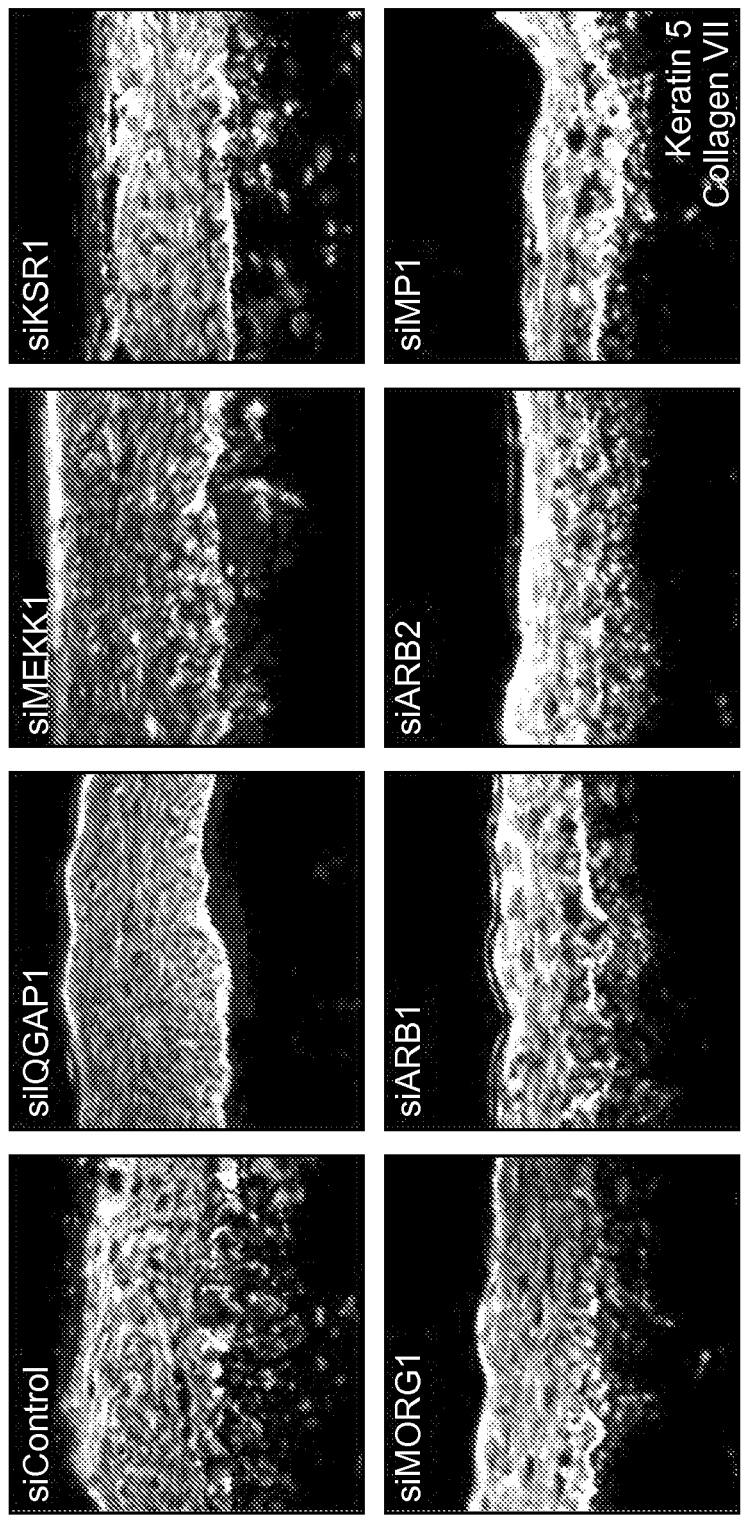
FIG. 5 demonstrates that IQGAP1 is required for RAS-induced neoplastic invasion. (A) Immunofluorescence staining of the epithelial marker keratin 5 (orange) and the basement membrane zone (BMZ) protein type-VII collagen (green) on H-RAS$^{G12V}$/IκBαM organotypic human tissue expressing siRNAs targeting a non-functional control, IQGAP1, MEKK1, KSR1, MORG1, ARB1, ARB2, or MP1 sequences. (B) qRT-PCR validating knockdown of ERK/MAPK scaffolds in (A). (C) Quantitative invasion index (±SD) of neoplastic tissue in (A). (D) qRT-PCR demonstrating unchanged IQGAP1 mRNA levels following knockdown of ERK/MAPK scaffolds in (A). All stains and qPCR (±SD) are representative images for at least 3 independent experiments.
Figure 5:
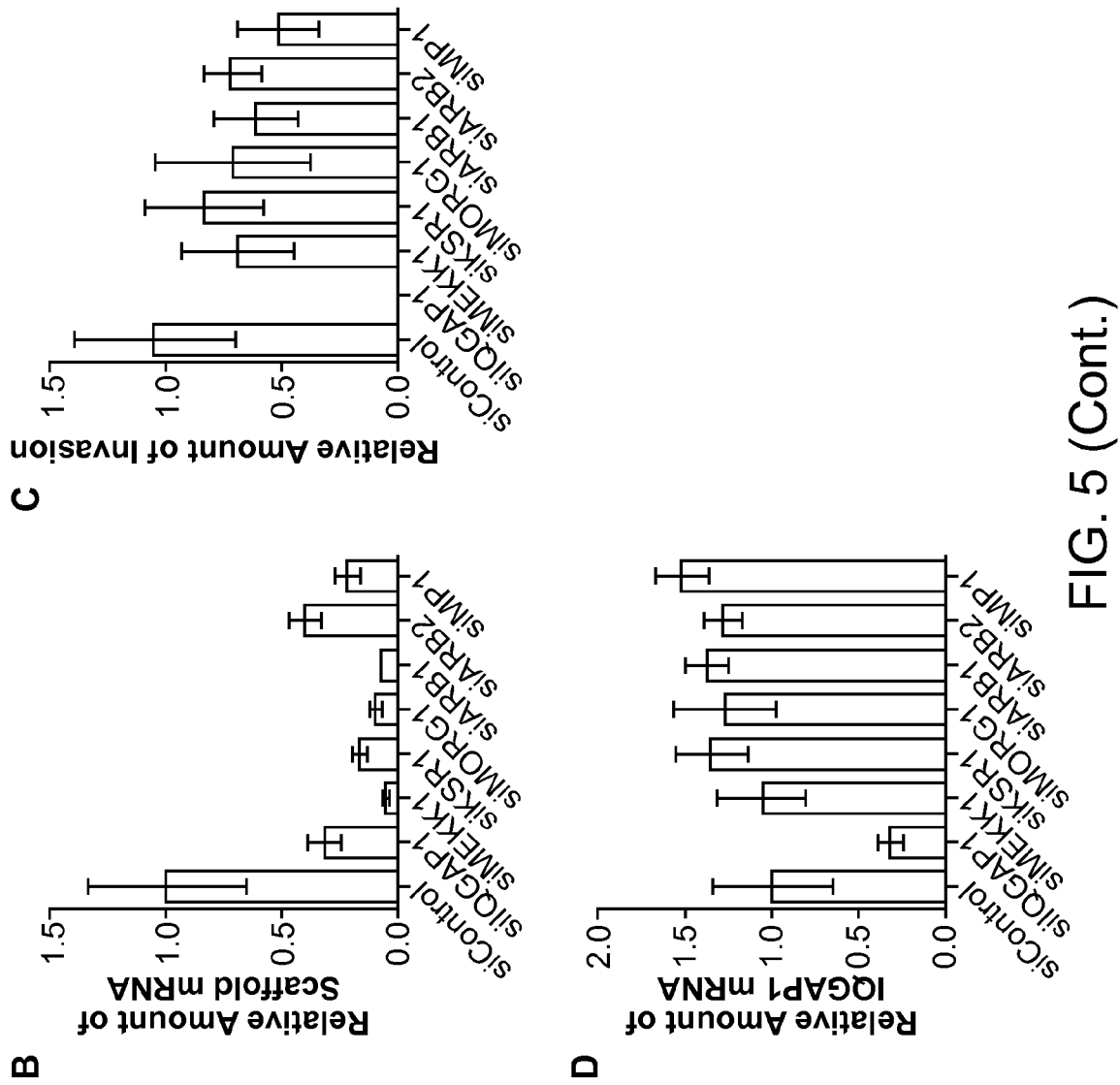
Figure 18:
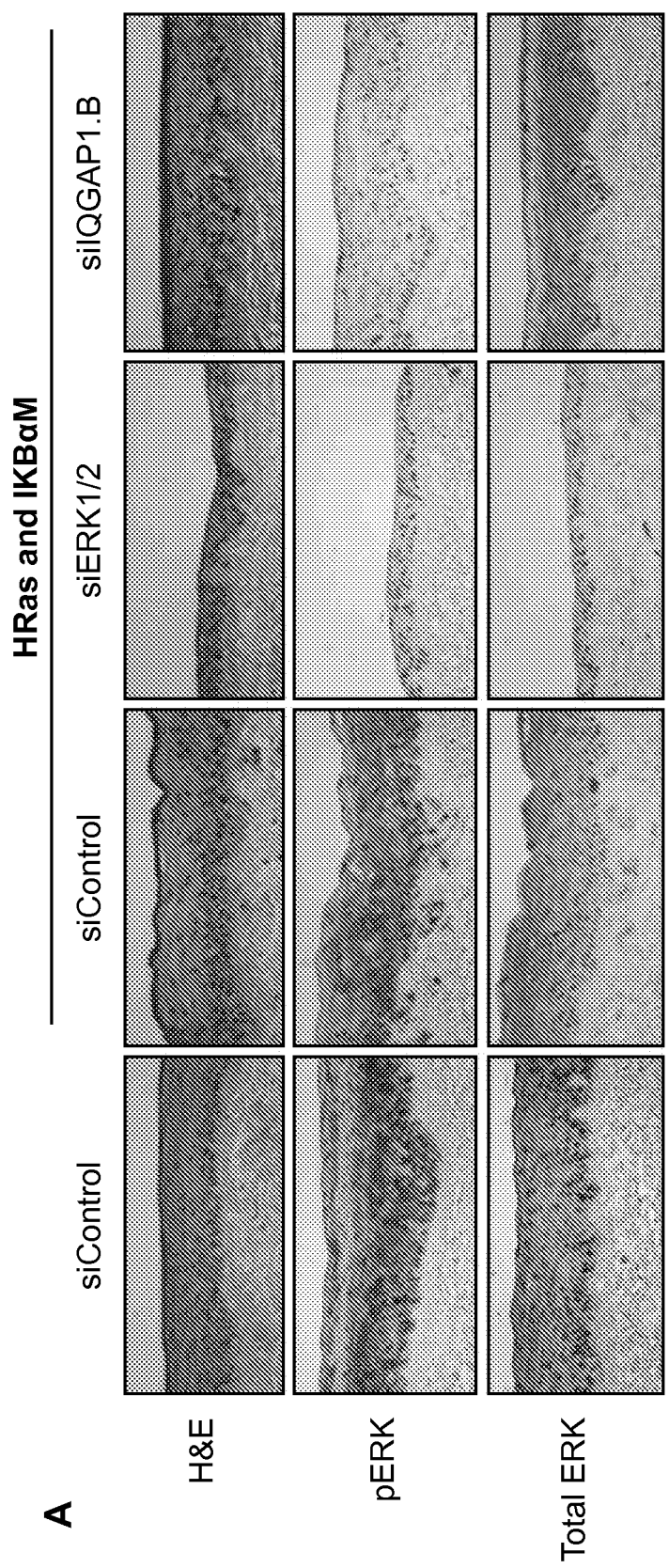
FIG. 18 demonstrates that IQGAP1 knockdown results in diminished phosphorylated-ERK. (A) Immunohistochemistry staining for histology (top), phosphorylated ERK (middle), and total ERK (bottom) for LacZ and H-RAS$^{G12V}$/IκBαM organotypic human tissue expressing siRNAs targeting a non-functional control, ERK1 and ERK2, or IQGAP1 sequences. (B) Immunoblots of H-RAS$^{G12V}$/IκBαM-infected keratinocyte extracts comparing phosphorylated ERK, total ERK, and IQGAP1 levels following nucleofection with siRNAs targeting a non-functional control, ERK1 and ERK2, or two different IQGAP1 sequences. Cell lysates were also probed with antibodies to actin to verify equal loading. (C) Immunoblots of H-RAS$^{G12V}$/IκBαM-infected keratinocyte extracts comparing IQGAP1, phosphorylated ERK, and total ERK levels following nucleofection with siRNAs targeting a non-functional control, KSR1, MP1, or IQGAP1 sequences. Cell lysates were also probed with antibodies to actin to verify equal loading. (D) Primary human keratinocytes expressing hairpins to scrambled control or IQGAP1 sequence were lysed, immunoprecipitated with antibodies to phosphorylated ERK, and subjected to an in vitro kinase assay using ELK-1 protein as a substrate. Immunoblots were performed to detect levels of phosphorylated-ELK-1. Samples were confirmed for knockdown of IQGAP1 and equal loading (FIG. 16E). All stains and immunoblots are representative images for at least 3 independent experiments.
Figure 18:
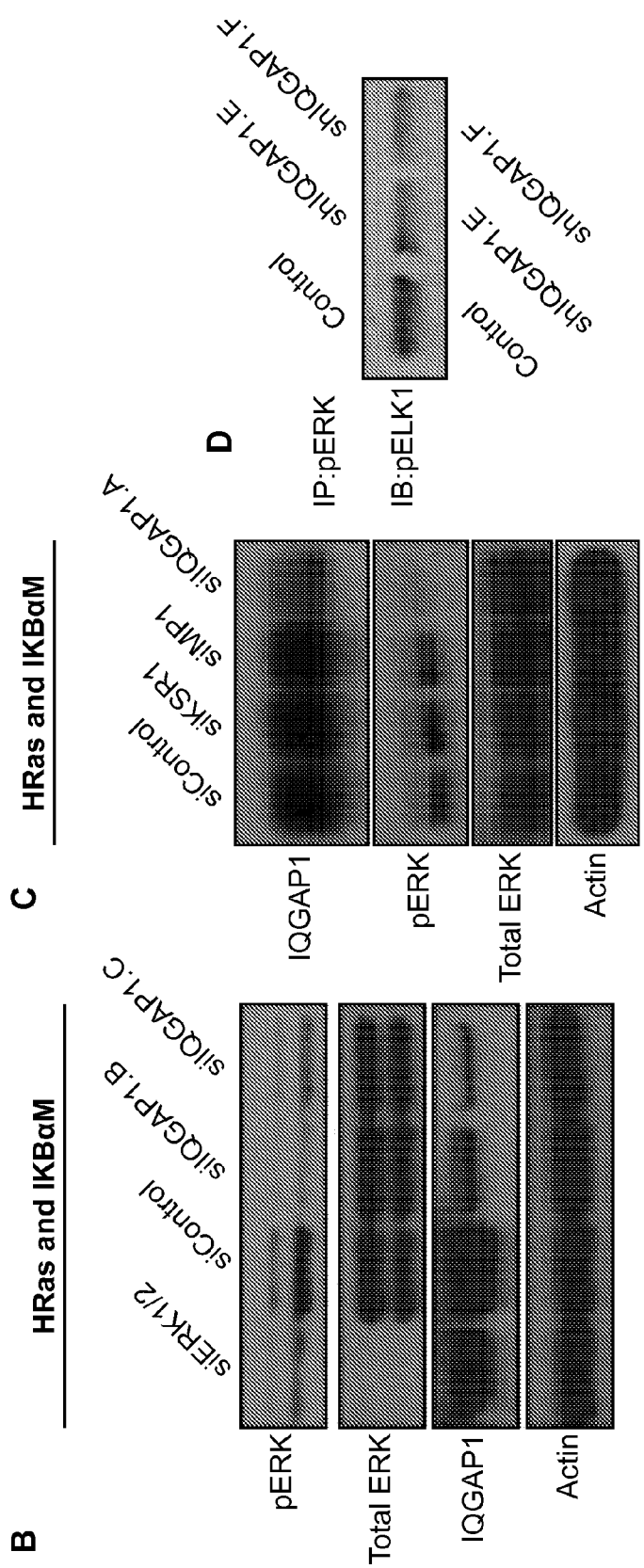

IQGAP1 depletion results in diminished phosphorylated ERK. To interrogate the mechanism by which siRNA-mediated IQGAP1 depletion results in inhibition of neoplastic invasion and tumor growth, we revisited our initial hypothesis. We began this study hypothesizing that knockdown of ERK/MAPK scaffolds would inhibit signaling though the ERK/MAPK cascade. To examine ERK/MAPK signal transduction, we evaluated changes in the activation of the most downstream effector, ERK. In neoplastic tissue depleted of IQGAP1, we not only observe inhibition of invasion, but also diminished phosphorylated ERK levels (FIG. 18A). Interestingly, IQGAP1 depleted tissue maintains a phenotypically normal level of total ERK (FIGS. 18A and 18B). ERK1/2 depleted transformed tissue is also non-invasive and lacks phosphorylated ERK; however it is also characterized by depletion of total ERK and significant hypoplasia (FIG. 18A). Since the potent MEK inhibitor UO126 also blocked invasion and diminished phosphorylated ERK levels without affecting total ERK (FIG. 2), it appears that IQGAP1 is capable of blocking invasion via inhibition of the signaling cascade in a manner similar to UO126 (FIG. 18B). Interestingly, in lysates from transformed keratinocytes, only IQGAP1 depletion resulted in diminished phosphorylated ERK, whereas depletion of ERK/MAPK scaffolds KSR1 and MP1 maintained control-like levels (FIG. 18C). Invasion proceeded normally in tissue regenerated from these cells (FIG. 5). To further validate observed perturbations to ERK/MAPK signaling output, we employed immunoprecipitation-kinase (IP) assays. These assays involve immunoprecipitation of active ERK from cell lysates followed by in vitro kinase assays wherein fusion protein for the downstream ERK target ELK-1 and ATP are added to lysates in buffer to determine if immunoprecipitated active ERK could activate its downstream target. Subsequently, samples are analyzed by western blot for presence of phosphorylated ELK-1 as an indicator of ERK/MAPK pathway activation. Upon depletion of IQGAP1 with shRNAs, pathway activity is diminished compared to control (FIG. 18D). Collectively, this data demonstrate that IQGAP1 mediates its tumor inhibitory functions through depletion of phosphorylated ERK similar to the MEK inhibitor UO126.

Figure 20:
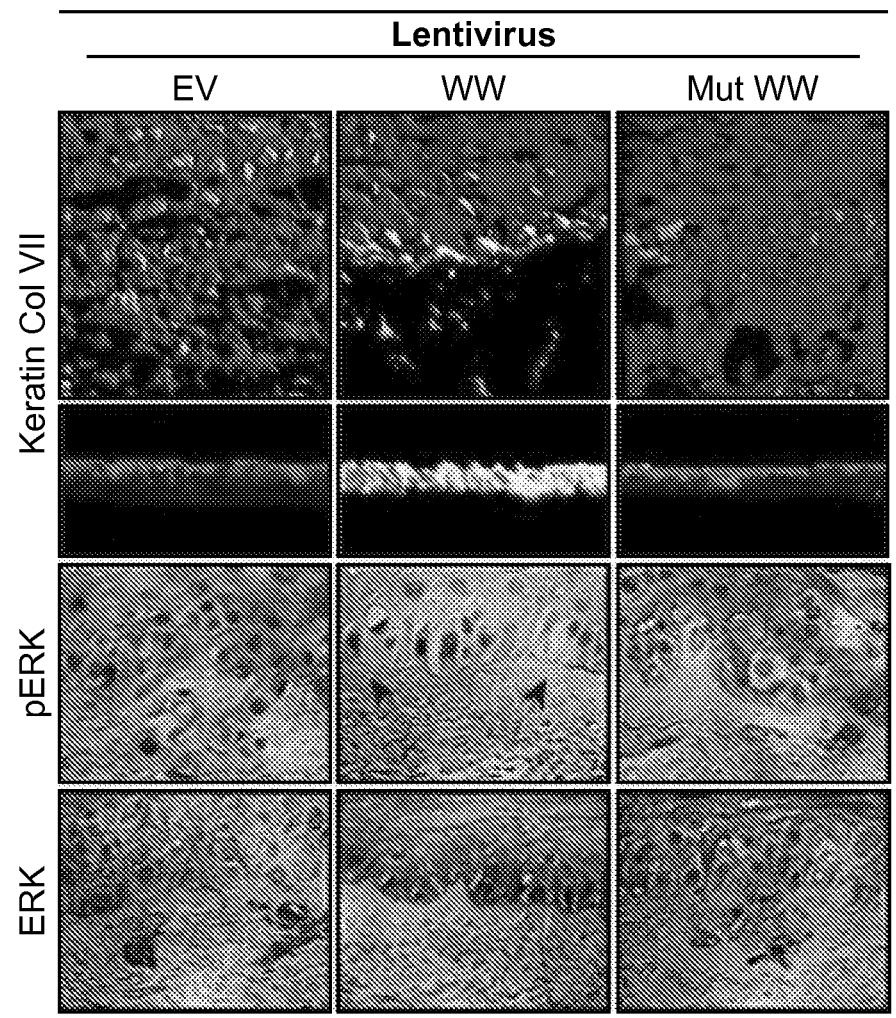
FIG. 20 demonstrates that the thirty-two amino acid WW domain of IQGAP1 is sufficient to recapitulate the phenotypic consequence of IQGAP1 depletion. (A) Confocal stack images showing the expression of keratin (in red), BMZ protein type-VII collagen (in green), and nuclei of keratinocytes and fibroblasts (in blue) of Ras-driven organotypic human epidermal neoplasia, treated with lentivirus corresponding to empty vector control (EV), IQGAP1 WW domain (WW), or mutant WW domain (mutant WW).) (B) Immunoblots myc-tag, pErk1/2, and total Erk1/2 levels on cells as in (A). (C) Cells as in (A) were lysed, immunoprecipitated with antibodies to phosphorylated ERK, and subjected to an in vitro kinase assay using ELK-1 protein as a substrate. Immunoblots were performed to detect levels of phosphorylated-ELK-1, levels of myc, and levels of actin as a loading control. All stains and immunoblots are representative images for at least 3 independent experiments.

The WW domain mediates IQGAP1 pro-tumor scaffolding. We hypothesized that overexpressing the WW domain of IQGAP1, which is responsible for binding ERK, might sequester ERK away from the full-length scaffold and thereby inhibit signal transduction. To test this hypothesis, we cloned the IQGAP1 WW domain into a selectable lentivirus expression vector, infected keratinocytes, and assayed effects in our regenerated human tissue model system. Overexpression of the IQGAP1 WW domain was sufficient to recapitulate the non-invasive tissue observed with knockdown of the IQGAP1 scaffold (FIG. 20A). Furthermore, the WW domain prevented characteristic degradation of the BMZ. Since there are currently no antibodies directed against the WW domain of IQGAP1, it was cloned with a 5' myc tag to enable identification (FIG. 20B). WW domain expressing tissue also showed diminished phosphorylated ERK without an effect on total ERK levels (FIGS. 20A and 20B). Furthermore, immunoprecipitation of pERK from cell lysates expressing the WW domain followed by in vitro kinase assays revealed diminished downstream pELK1 levels as compared to control treated cells.

The WW domain of IQGAP1 inhibits RAS-driven tumorigenesis. Having identified a role for the WW domain of IQGAP1 in a RAS-mediated model of SCCs, we next sought to determine if the WW domain would function similarly in RAS- and non-RAS-driven melanoma. We identified three melanoma lines that had either a BRAF V600E mutation, an NRAS Q61L mutation, or no RAS/RAF mutations. As expected, lines with constitutive activating mutations showed increased levels of phosphorylated ERK compared to primary normal human melanocytes (FIG. 21A). The melanoma cell line without RAS or RAF mutations did not have increased pERK signaling.

To further characterize the effects of the IQGAP1 WW domain sequence in a variety of cancers, we assayed effects on cell growth of human cancer cell lines in a cell viability assay. Lentiviral-driven WW domain delivery significantly impaired proliferation of skin (squamous ell carcinoma and melanoma), breast, prostate, colorectal, and lung tumor cells characterized by EGFR over-expression, KRAS mutation, or BRAF mutation without affecting growth of normal epithelial cells (FIG. 21a). Furthermore, normal human primary epithelial cells did not differ significantly in growth following lentiviral IQGAP1 WW domain infection (FIG. 21b). This data highlights the fact that the IQGAP1 SKIB could be effective in a variety of cancers characterized by pathological MAPK signaling. To further explore the suppressed proliferation due to the WW domain, we next employed melanoma cancer cell lines previously characterized to have either BRAF V600E or NRAS Q61 L mutations as well as a control melanoma line with wild-type BRAF and NRAS genes (Davies, H., et al. Mutations of the BRAF gene in human cancer. Nature 417, 949-954 (2002); Pavey, S., et al. Microarray expression profiling in melanoma reveals a BRAF mutation signature. Oncogene 23, 4060-4067 (2004)). IQGAP1 WW domain delivery via lentiviral transduction impaired tumorigenesis in BRAF and NRAS mutant, but not wild-type, tumor cells (FIG. 21c-f). Macroscopic inspection of tumors derived from cell lines expressing a BRAF V600E mutation, an NRAS Q61L mutation, or no mutations in RAS/RAF convincingly demonstrate the diminished tumor formation in WW domain expressing, RAS-mediated melanoma cells compared to control (FIG. 21d). Together these data suggest a preferential inhibitory effect by the IQGAP1SKIB on neoplasias characterized by mutations upstream of Erk1/2.

Figure 19:
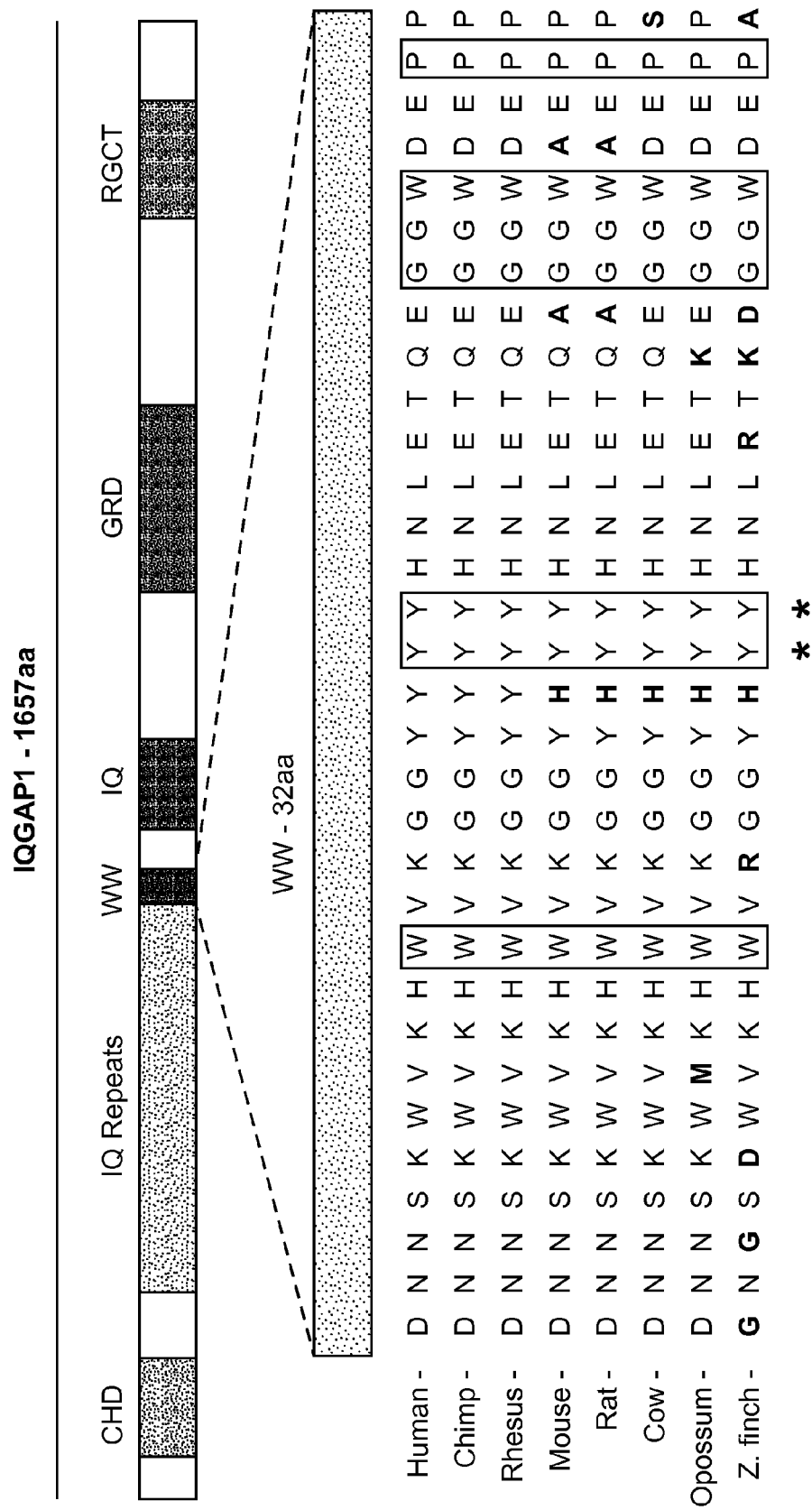
FIG. 19 illustrates that the WW domain of IQGAP1 is highly conserved. Diagram of conservation of IQGAP1 WW domain with amino acid sequence for various species indicated (human: SEQ ID NO:1; chimp: SEQ ID NO:2; rhesus: SEQ ID NO:3; mouse: SEQ ID NO:4; rat: SEQ ID NO:5; cow: SEQ ID NO:6; opossum: SEQ ID NO:7; zebra finch: SEQ ID NO:8). Divergent amino acids appear in red. Gray shading indicated highly conserved residues across WW domains from multiple proteins (50). The two highlighted tyrosine (Y) residues in the center of the WW domain were mutated to alanine (A) residues to make the WW mutant indicated in previous figures.
Figure 22:
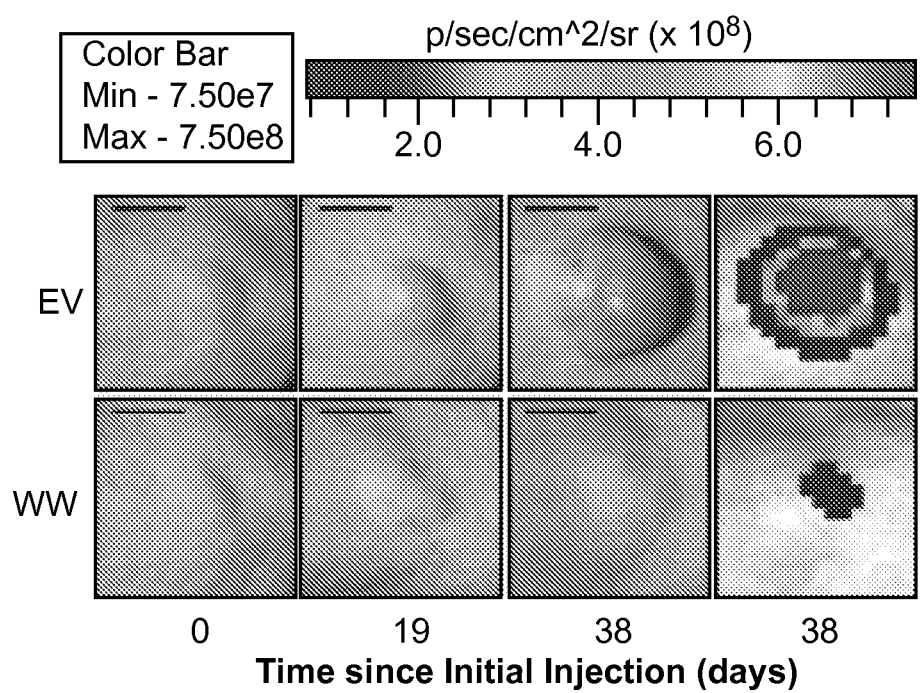
FIG. 22 depicts diminished tumorigenesis in vivo in RAS-driven cancer expressing the thirty-two amino acid WW domain of IQGAP1 (A) Established xenograft tumors derived from BRAFV600E mutant SK-MeI-28 melanoma cancer cells intratumorally injected with EV or WW lentivirus with tumor growth quantified by mean average radiance (n=5 mice per group). (B) Tumor growth following treatment as in (A) as quantified by tumor volume. (C) Representative images of mice as in (A) at times as indicated. Scale bar: 5 mm.
Figure 23:
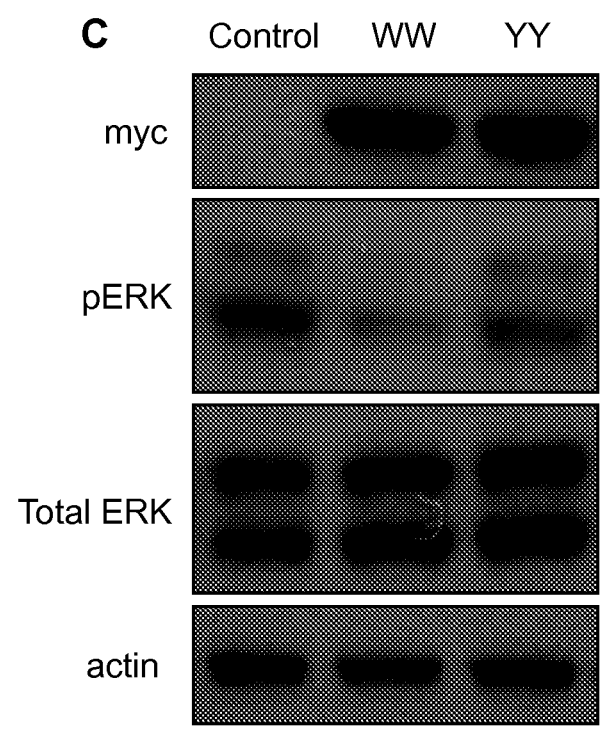
FIG. 23 demonstrates that the thirty-two amino acid WW domain of IQGAP1 inhibits growth of established RAS-driven tumors in vivo. (A) Established xenograft tumors derived from EGFR-overexpressing breast cancer line MDA-MB-468 intratumorally injected with lentivirus corresponding to empty vector (EV), WW domain (WW), or mutant WW domain (Mutant WW) (n=2 mice per group; tumor volumes±SD). (B) Representative images of mice as in (a). Scale bar=5 mm. (C) Immunoblots of oncogenic Ras expressing keratinocytes infected as in (A). Cell lysates were probed for presence of myc as well as pERK and total ERK levels. All immunoblots are representative of 3 experiments.

The WW domain as a novel oncotherapeutic. Taken together these data indicate that the WW domain of IQGAP1 represents an as yet unidentified selectable tumor therapeutic for the treatment of RAS-driven cancers. In order to be a successful cancer therapy, however, the WW domain must also slow or diminish growth of established tumors. To precisely investigate the ability of the WW domain of IQGAP1 to inhibit growth of tumors, melanoma or breast cancer cell were injected into the subcutaneous space of hairless SCID mice and allowed to grow normally for 3-4 weeks. For dosing in this initial experiment, we elected to use five separate intratumoral injections of lentivirus corresponding to the WW domain of IQGAP1, empty vector, or mutant WW over the course of two weeks. Tumor growth was assessed by tumor volume and bioluminescence. On the day of the first injection, all tumors were ~200 mm$^3$. In both tumor types, control treated tumors whereas WW domain treated tumors either exhibited tumor stasis (FIG. 22A-C) or decreased in size by nearly 50% (FIG. 23A-B). At 38 days post initial injection, WW domain treated melanoma tumor xenografts were nearly 3.5 fold smaller than control tumors. Even more interestingly, sixty days after the initial injection, WW domain treated breast tumors were nearly 5 fold smaller than control treated tumors (FIG. 23A). As an additional control, we also injected tumors with a mutant form of the WW domain of IQGAP1 in which two highly conserved tyrosine (Y) residues were mutated to alanine (FIG. 19). Primary normal human keratinocytes infected with this WW domain mutant had normal levels of phosphorylated ERK suggesting that these two center tyrosine residues were crucial in the ability of the WW domain to bind ERK (FIG. 23C). Furthermore, tumors that received this mutant-WW injection were much more similar to control (FIG. 23A). Taken together, our data demonstrate that ectopic expression of the wildtype WW domain of IQGAP1 inhibits ERK/MAPK signaling through binding of ERK and thus is capable of inhibiting growth of established tumors irrespective of tissue type.

Figure 25:
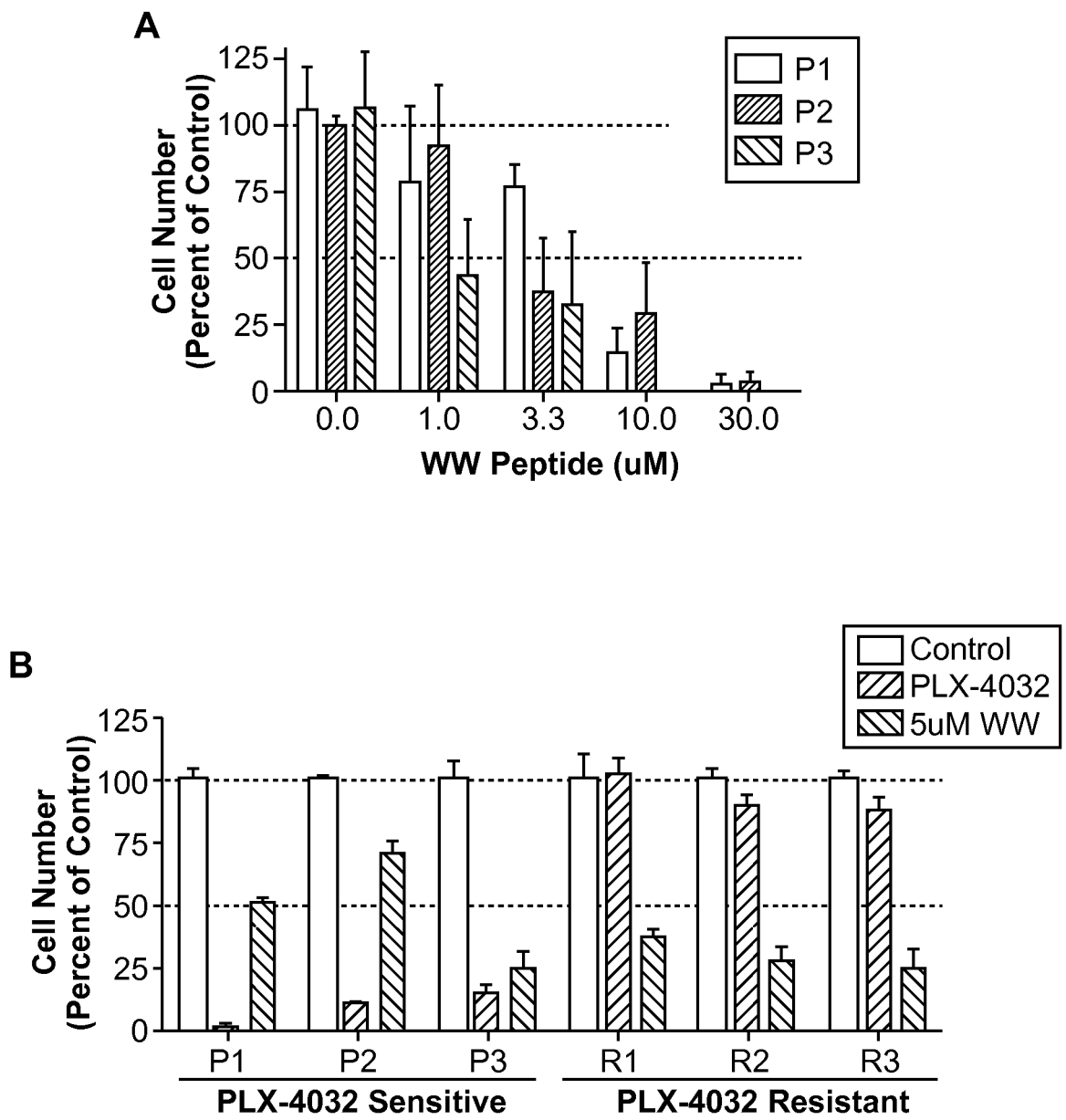
FIG. 25 demonstrates that exogenous WW peptide bypasses resistance to B-Raf inhibitors in melanoma. (A) Proliferation of PLX-4032 sensitive BRAFV600E melanoma cell lines (P1, SK-MeI-28; P2, A375; and P3, SK-MeI-5) at increasing doses of R8-myc-tagged WW peptide. (B) Proliferation assays of PLX-4032 resistant lines (R1, SK-MeI-28; R2, A375; and R3, SK-MeI-5) treated with 5 μM R8-myc-tagged SCR peptide and DMSO (control), 5 μM SCR peptide and 5 μM PLX-4032 (PLX-4032), or 5 μM R8-myc-tagged WW peptide and DMSO (5 μM WW).

Having identified a novel target and a subset of tumors that will be affected by the proposed therapy and after demonstrating a therapeutic effect in a variety of models, we next wanted to explore our ability to convert this WW domain target into a robust drug. To test whether exogenous delivery of the WW domain may have potential therapeutic applications, we generated a 32 amino acid WW peptide that was rendered cell and tissue penetrating by adding eight arginine residues using an approach shown previously to mimic HIV TAT sequence function (Rothbard, J. B., et al. Conjugation of arginine oligomers to cyclosporin A facilitates topical delivery and inhibition of inflammation. Nature Medicine 6, 1253-1257 (2000)). WW peptide was added directly to the media of Ras-driven organotypic epidermal neoplasia and, in contrast to control peptide, IQGAP1 WW peptide abolished neoplastic invasion, abrogated BMZ degradation, and diminished pErk1/2 levels (FIGS. 24A and B). Delivery of WW peptide also inhibited proliferation of BRAF mutant melanoma cells in a dose-dependent manner (FIG. 25A). Exogenous IQGAP1 WW peptide thus exerts anti-neoplastic effects in a similar manner to WW sequence genetically delivered via virus.

Example 4

Results

Figure 26:
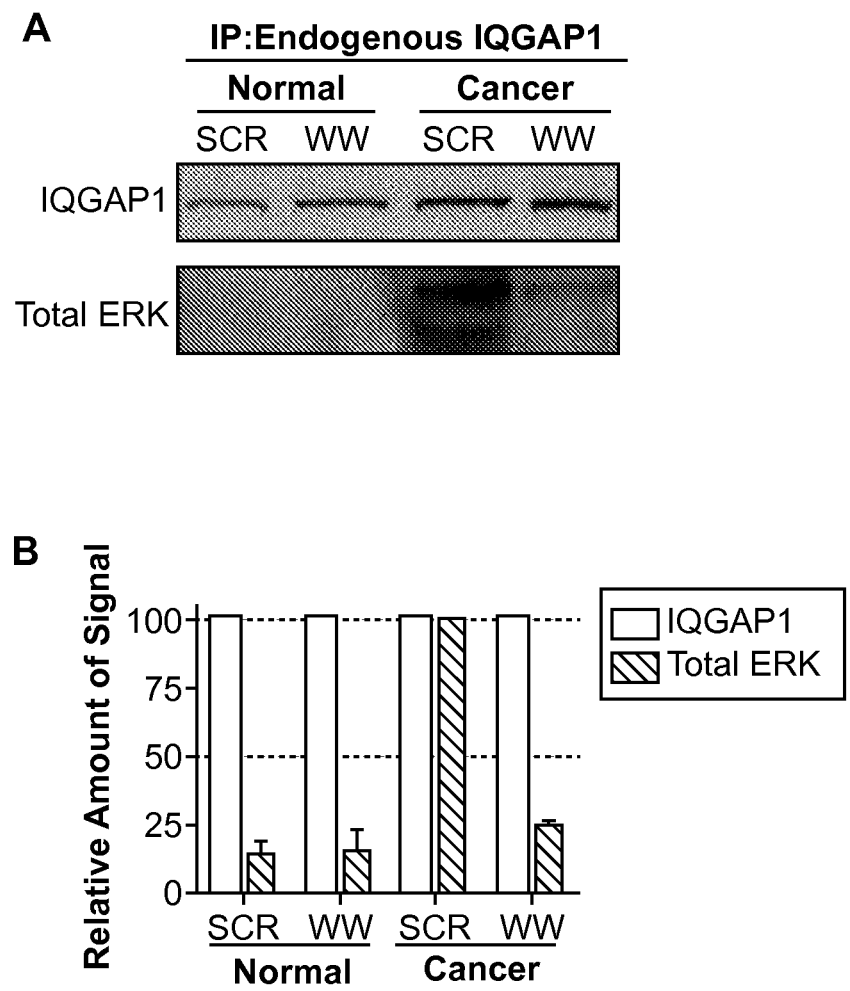
FIG. 26 demonstrates that exogenous WW peptide acts by Scaffold Kinase Interaction Blockade (SKIB). (A) Immunoprecipitation of endogenous IQGAP1 protein and associated Erk from primary human cells (normal) or BRAFV600E mutant SK-MeI-28 melanoma cells (cancer) following daily treatment with 10 μM R8-myc-tagged SCR or WW peptide for six days. (B) Relative Erk levels as a function of immunoprecipitated IQGAP1 as in (d). n=3, ±SD.

The newly available kinase inhibitor Vemurafenib (PLX-4032) targeting mutant BRAFV600E MAPK kinase kinase in melanoma has been hindered by acquired resistance via bypass mechanisms that restore Erk1/2 activation. If the WW domain acts in a mechanistically distinct fashion from direct kinase inhibition, WW peptide effects should be unaltered by acquired resistance to B-Raf inhibition. To test this, three WW-sensitive BRAFV600E-expressing human melanoma cell lines (FIG. 25A) were rendered resistant to the PLX-4032 inhibitor of BRAFV600E kinase activity by long-term continual growth in PLX-4032, with resistance confirmed by insensitivity to PLX-4032-mediated growth inhibition (FIG. 26B). WW inhibited growth of PLX-4032-resistant melanoma cells similarly to PLX-4032-sensitive parental cells (FIG. 26B), indicating that WW domain acts in a manner that is non-redundant with direct kinase inhibition.

Example 5

Results

To explore the mechanism of WW peptide action, we characterized effects on IQGAP1-Erk binding in normal and cancerous cells. Interestingly very little Erk1/2 is associated with endogenous IQGAP1 in normal cells, while there is much more Erk1/2 bound to IQGAP1 in cancer cells (FIG. 27A). WW peptide significantly decreased levels of total Erk1/2 bound to endogenous IQGAP1 (FIG. 27A, 27B). The 32 amino acid IQGAP1 WW sequence thus disrupts scaffold-kinase interactions between IQGAP1 and Erk1/2. We present a schematic of the resulting approach to scaffold-kinase interaction blockade (SKIB) in cancer. (FIG. 28).

Example 6

Results

To test the efficacy of systemic delivery of WW peptide in vivo, $0.5 \times 10^6$ luciferase-expressing SK-MeI-28 were injected into the subcutaneous space of hairless immunodeficient 6-8 week old SCID mice (SHO stock, Charles Rovers). Mouse xenografts were allowed to grow untreated for 1 week. Subsequently, tumors were measured and randomized two groups of similar tumor size. Each group was subcutaneously implanted with osmotic pumps (Alzet, model 2002) releasing 0.5 uL of scrambled or WW peptide per hour for 14 days. As shown in FIG. 27, systemic delivery of WW peptide in vivo diminishes tumorigenesis. These results translate the conceptual advances of the WW peptide to a new systemically deliverable therapeutic without adverse toxic effects to animals, and indicate that the WW peptide could be used therapeutically rather than embarking on the long-term and costly development of a small molecule inhibitor of IQGAP1-ERK.

Erk1/2 MAP kinase (MAPK) cascade up-regulation occurs in >30% of human cancers often via mutational activation of receptor tyrosine kinases, such as EGFR, or other upstream genes, including KRAS and BRAF.). WW peptide inhibited tumorigenesis in cells from diverse tissues, all of which were characterized by Erk1/2 MAPK pathway activation at a variety of pathway levels from upstream receptor tyrosine kinases to commonly mutated RAS and RAF genes suggesting that the scope of market for such a drug would be roughly ~30% of the 1.5 million Americans diagnosed with cancer each year. The therapeutics identified herein will be useful as an orthogonal approach to current kinase-targeted treatments and as a potential opportunity to address a substantial unmet need for currently unresponsive cancers.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method of inhibiting RAS pathway activity in a cell, the method comprising:

adding to a cell in vitro an effective amount of an IQ motif containing GTPase activating protein I (IQGAP1) scaffold-kinase interaction blockade (SKIB) agent to block the interaction of a scaffold protein and a kinase thereby inhibiting RAS pathway activity in the cell, wherein the SKIB agent is an isolated IQGAP1 WW peptide or a nucleic acid encoding an isolated IQGAP1 WW peptide, wherein the IQGAP1 WW peptide consists essentially of the WW domain of IQGAP1.

2. The method according to claim 1, wherein the cell is a cancer cell, and the cancer is a RAS pathway-driven cancer.

3. The method according to claim 2, wherein the cell is selected from the group consisting of a skin cancer cell, a breast cancer cell, a colorectal cancer cell, and a prostate cancer cell.

4. The method according to claim 2, wherein the method inhibits RAS-driven cell proliferation and/or cell metastasis.

* * * * *